US007994317B2

(12) United States Patent
Ding et al.

(10) Patent No.: US 7,994,317 B2
(45) Date of Patent: Aug. 9, 2011

(54) SEH INHIBITORS AND THEIR USE

(75) Inventors: Yun Ding, Waltham, MA (US); Joseph Paul Marino, Jr., King of Prussia, PA (US); Peng Li, King of Prussia, PA (US); Allyn T. Londregan, King of Prussia, PA (US); Barry A. Morgan, Waltham, MA (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 88 days.

(21) Appl. No.: 12/513,186

(22) PCT Filed: Nov. 2, 2007

(86) PCT No.: PCT/US2007/083449
§ 371 (c)(1),
(2), (4) Date: May 1, 2009

(87) PCT Pub. No.: WO2008/105968
PCT Pub. Date: Sep. 4, 2008

(65) Prior Publication Data
US 2010/0069391 A1  Mar. 18, 2010

Related U.S. Application Data

(60) Provisional application No. 60/864,178, filed on Nov. 3, 2006.

(51) Int. Cl.
*C07D 251/54* (2006.01)
*C07D 403/12* (2006.01)
*C07D 403/14* (2006.01)
*A61K 31/53* (2006.01)
*A61P 9/08* (2006.01)
*A61P 9/10* (2006.01)
*A61P 9/12* (2006.01)
*A61P 11/06* (2006.01)
*A61P 11/00* (2006.01)
*A61P 13/12* (2006.01)

(52) U.S. Cl. ........ 544/197; 544/198; 544/208; 544/209; 514/245

(58) Field of Classification Search .................. 544/197, 544/198, 208, 209; 514/245
See application file for complete search history.

(56) References Cited

U.S. PATENT DOCUMENTS

2004/0029902 A1   2/2004   Singh et al.

FOREIGN PATENT DOCUMENTS

| EP | 1464335 | 10/2004 |
|---|---|---|
| WO | WO2009049154 A1 | 4/2009 |
| WO | WO2009049157 A1 | 4/2009 |
| WO | WO2009049165 A1 | 4/2009 |

OTHER PUBLICATIONS

Dorrance, Phd., Et Al.: "An Epoxide Hydrolase Inhibitor, 12-(3-Adamantan-1-Yl-Ureido)Dodecanoic Acid (AUDA), Reduces Ischemic Cerebral Infact Size in Stroke-Prone Spontaneously Hypertensive Rats" Journal of Cardiovascular Pharmacology, Dec. 2005, vol. 46, No. 6, pp. 842-848.

Fornage, Et Al.: "The Soluble Epoxide Hydrolase Gene Harbors Sequence Variation Associated With Susceptibility to and Protection From Incident Ischemic Stroke" Human Molecular Genetics, 2005, vol. 14, No. 19, pp. 2829-2837.

Fretland, Et Al.: "Epoxide Hydrolases: Biochemistry and Molecular Biology", Chemico-Biological Interactions. 2000; vol. 129, pp. 41-59.

Imig, Et Al.: "Soluble Epoxide Hydrolase Inhibition Lowers Arterial Blood Pressure in Angiotensin II Hypertension" Hypertension. 2002; vol. 39 (Part 2), pp. 690-694.

Imig, Et Al.: "An Orally Active Epoxide Hydrolase Inhibitor Lowers Blood Pressure and Provides Renal Protection in Salt-Sensitive Hypertension" Hypertension. 2005; vol. 46 (Part 2): pp. 975-981.

Imig, Et Al.: "Cardiovascular Therapeutic Aspects of Soluble Epoxide Hydrolase Inhibitors" Cardiovascular Drug Reviews. 2006; vol. 24, No. 2, pp. 169-188.

Inceoglu, Et Al.: "Inhibition of Soluble Epoxide Hydrolase Reduces LPS-Induced Thermal Hyperalgesia and Mechanical Allodynia in a Rat Model of Inflammatory Pain" Life Sciences. 2006; vol. 79, pp. 2311-2319.

Jones, P.D. Et Al.: "Synthesis and SAR of Conformationally Restricted Inhibitors of Soluble Epoxide Hydrolase" Bioorganic & Medicinal Chemistry Letters, Oct. 1, 2009, vol. 16, No. 19, pp. 5212-5216.

Jung, Et Al.: "Soluble Epoxide Hydrolase is a Main Effector of Angiotensin II-Induced Hypertension" Hypertension. 2005; vol. 45 (Part 2), pp. 759-765.

Koerner, Et Al.: "Polymorphisms in the Human Soluble Epoxide Hydrolase Gene *EPHX2* Linked to Neuronal Survival After Ischemic Injury" The Journal of Neuroscience. Apr. 25, 2007; vol. 27, No. 17, pp. 4642-4649.

Krotz, Et Al.: "Membrane Potential-Dependent Inhibition of Platelet Adhesion to Endothelial Cells by Epoxyeicosatrienoic Acids" Arterioscler Thrombosis Vascular Biology. 2004; vol. 24, pp. 595-600.

Lee, Et Al.: "Genetic Variation in Soluble Epoxide Hydrolase (*EPHX2*) and Risk of Coronary Heart Disease: The Atherosclerosis Risk in Communities (ARIC) Study" Human Molecular Genetics. 2006; vol. 15, No. 10, pp. 1640-1649.

Loch, Et Al.: "Prevention of Hypertension in DOCA-Salt Rats by an Inhibitor of Soluble Epoxide Hydrolase" Cell Biochemistry and Biophysics. 2007; vol. 47, pp. 87-97.

Sato, Et Al.: "Soluble Epoxide Hydrolase Variant (Glu287Arg) Modifies Plasma Total Cholesterol and Triglyceride Phenotype in Familial Hypercholesterolemia: Intrafamilial Association Study in an Eight-Generation Hyerlipidemic Kindred" Journal of Human Genetics. 2004; vol. 49, pp. 29-34.

Sinal, Et Al.: "Targeted Disruption of Soluble Epoxide Hydrolase Reveals a Role in Blood Pressure Regulation" The Journal of Biological Chemistry. 2000; vol. 275, No. 51, pp. 40504-40510.

(Continued)

*Primary Examiner* — Venkataraman Balasubramanian
(74) *Attorney, Agent, or Firm* — Linda E. Hall; John L. Lemanowicz

(57) ABSTRACT

The invention is directed to novel sEH inhibitors and their use in the treatment of diseases mediated by the sEH enzyme.

11 Claims, No Drawings

OTHER PUBLICATIONS

Spector, Et Al.: "Epoxyeicosatrienoic Acids (Eets): Metabolism and Biochemical Function" Progress in Lipid Research. 2004; vol. 43, pp. 55-90.

Wei, Et Al.: "Sequence Variation in the Soluble Epoxide Hydrolase Gene and Subclinical Coronary Atherosclerosis: Interaction With Cigarette Smoking" Atherosclerosis. 2007; vol. 190, pp. 26-34.

Xu, Et Al.: "Prevention and Reversal of Cardiac Hypertrophy by Soluble Epoxide Hydrolase Inhibitors" Proceedings National Academy of Sciences. 2006; vol. 103, No. 49, pp. 18733-18738.

Zhao, Et Al.: "Soluble Epoxide Hydrolase Inhibition Protects the Kidney from Hypertension-Induced Damage" Journal of the American Society of Nephrology, 2004, vol. 15, pp. 1244-1253.

SEH INHIBITORS AND THEIR USE

This application is a 371 of International Application No. PCT/US2007/083449, filed 2 Nov. 2007, which claims the benefit of 60/864178, filed 3 Nov. 2006, which are incorporated herein in their entirety.

FIELD OF THE INVENTION

The invention is directed to novel sEH inhibitors and their use in the treatment of diseases mediated by the sEH enzyme.

BACKGROUND OF THE INVENTION

Epoxide functional groups may be found in drugs, xenobiotic materials, and endogenous biomolecules. Epoxide hydrolases, found in both plants and animals, are enzymes that convert epoxides to diols by hydrolysis. In mammals, soluble epoxide hydrolase ("sEH") is primarily responsible for the metabolism of arachidonic acid derivatives known as epoxyeicosatrienoic acids ("EETs"). sEH converts EETs into dihydroxyeicosatrienoic acids ("DHETs"). Several publications have described the beneficial vasodilatory, anti-inflamatory, and anti-thrombotic effects of EETs. See E.g. Spector et al., *Prog. Lipid Res.*, 43, 55-90, 2004; Imig, *Cardiovasc. Drug Rev.*, 24, 169-188, 2006. DHETs are generally inactive and thus do not exhibit the beneficial effects of EETs.

Conversely, microsomal epoxide hydrolase ("mEH") catalyzes the hydrolysis of a broad range of epoxide substrates including carcinogenic polycyclic aromatic hydrocarbons and reactive epoxides, thus it provides an important detoxification pathway. Polymorphisms in mEH may lead to differences in bioactivation of pro-carcinogens and several human epidemiological studies suggest that mEH genotype is associated with altered cancer risk. Fretland & Omiecinski, *Chemico-Biol. Int.*, 129, 41-59, 2000.

Pharmacological, knockout mouse phenotype and genetic polymorphism studies suggest that elevated EET levels are protective in numerous cardiovascular disorders including hypertension [Sinal et al., *J. Biol. Chem.*, 275, 40504-40510, 2000; Imig et al., *Hypertension*, 39, 690-694, 2002; Jung et al., *Hypertension*, 45, 759-765, 2005; Loch et al., *Cell Biochem Biophys.*, 47, 87-98, 2007], heart failure [Xu et al., *Proc. Natl. Acad. Sci. U.S.A.*, 103, 18733-18738, 2006], renal dysfunction/end organ damage [Zhao et al., *J. Am. Soc. Nephroi.*, 15, 1244-1253, 2004; Imig et al., *Hypertension*, 46, 975-981, 2005], stroke [Dorrance et al., *J. Cardiovasc. Pharmacol.*, 46, 842-848, 2005; Formage et al., *Hum. Mol. Genet.*, 14, 2829-2837, 2005; Koerner et al., *J. Neurosci.*, 27; 4642-4649, 2007], atherosclerosis and thrombosis [Sato et al., *J. Hum. Genet.*, 49, 29-34, 2004; Lee et al., *Hum Mol. Genet.*, 15, 1640-1649, 2006; Wei et al., Atherosclerosis, 190, 26-34, 2007; Krotz et al., Arterioscler. Thromb. Vasc. Biol., 24; 595-600, 2004] and inflammation [Inceoglu et al., *Life Sci.*, 79, 2311-2319, 2006].

One approach to the treatment of such conditions designed to take advantage of the beneficial effect of EETs has been to inhibit the action of sEH thereby preventing EET degradation. In light of the role sEH plays in the degradation of EETs, it is desirable to prepare compounds that inhibit its activity. Thus, there is a need to identify compounds that inhibit sEH, which can be used in the treatment of a variety of conditions mediated by the sEH enzyme.

SUMMARY OF THE INVENTION

The invention is directed to novel sEH inhibitors and their use in the treatment of diseases mediated by the sEH enzyme, such as hypertension. The invention is further directed to pharmaceutical compositions comprising a compound of the invention. The invention is still further directed to methods of inhibiting sEH and treatment of conditions associated therewith using a compound of the invention or a pharmaceutical composition comprising a compound of the invention.

DETAILED DESCRIPTION OF THE INVENTION

In describing the invention, chemical elements are identified in accordance with the Periodic Table of the Elements. Abbreviations and symbols utilized herein are in accordance with the common usage of such abbreviations and symbols by those skilled in the chemical and biological arts. For example, the following abbreviations are used herein:

"aq" is an abbreviation for aqueous

"BOP" is an abbreviation for (Benzotriazol-1-yloxy)tris(dimethylamino)phosphonium hexafluorophosphate "° C." is an abbreviation for degrees Celsius "DIEA" is an abbreviation for di-isopropylethylamine "DMAP" is an abbreviation for dimethylaminopyridine "DMF" is an abbreviation for dimethylformamide "DMSO" is an abbreviation for Dimethylsulfoxide "EDCl" is an abbreviation for N-(3-Dimethylaminopropyl)-N'-ethylcarbodiimide hydrochloride "equiv" is an abbreviation for equivalent "HOBT" is an abbreviation for 1-Hydroxybenzotriazole "HPLC" is an abbreviation for High Pressure Liquid Chromatography "g" is an abbreviation for gram or grams "L" is an abbreviation for liter or liters "LC-MS" is an abbreviation for Liquid chromatography-Mass spectrometry "mL" is an abbreviation for milliliter or milliliters "min" is an abbreviation for minute or minutes "mmol" is an abbreviation for millimole or millimolar "N" is an abbreviation for Normal and refers to the number of equivalents of reagent per liter of solution "Ph" is an abbreviation for phenyl "sat" is an abbreviation for saturated "TFA" is an abbreviation for trifluoroacetic acid "THF" is an abbreviation for tetrahydrofuran

TERMS AND DEFINITIONS

"Alkyl" refers to a monovalent saturated hydrocarbon chain having the specified number of member atoms. For example, C1-C8 alkyl refers to an alkyl group having from 1 to 8 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkylene" used alone or as suffix or prefix refers to a divalent straight or branched chain hydrocarbon radical comprising 1 to about 12 carbon atoms, which serves to links two structures together.

"Aryl" means an optionally substituted monocyclic or bicyclic ring system containing at least one aromatic ring. Examples and suitable values of the term "aryl" are phenyl, naphthyl, 1,2,3,4-tetrahydronaphthyl, indyl and indenyl.

"Aralkyl" and "heteroaralkyl" refer to a substituent that is attached via the alkyl group to an aryl, heteroaryl or cycloalkyl group.

"Cycloalkyl" refers to a monovalent saturated or unsaturated hydrocarbon ring having the specified number of member atoms. For example, C3-C6 cycloalkyl refers to a cycloalkyl group having from 3 to 6 member atoms. Unsaturated Cycloalkyl groups have one or more carbon-carbon double bonds within the ring. Cycloalkyl groups are not aromatic. C3-C7 cycloalkyl refers to cyclopropyl, cyclopropenyl, cyclobutyl, cyclobutenyl, cyclopentyl, cyclopentenyl, cyclohexyl, cyclohexenyl, cycloheptanyl, and cycloheptenyl. Cycloalkyl groups having more than 7 member atoms may be monocyclic, bridged or fused bicyclic ring systems. Cycloalkyl groups may be optionally substituted with one or more substituents as defined herein.

"($C_1$-$C_6$alkyl)O—" means an alkyl ether. Examples include methoxy, ethoxy, vinyloxy, allyloxy, ethynyloxyy, and 2-propynyloxy.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct specie in vitro or in vivo.

"Halo" refers to the halogen radical fluoro, chloro, bromo, or iodo.

"Haloalkyl" refers to an alkyl group that is substituted with one or more halo substituents. Haloalkyl includes trifluoromethyl.

"Heteroaryl" refers to a monovalent aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Unless otherwise specificed, heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, and napthyridinyl.

"Heteroatom" refers to a nitrogen, sulphur, or oxygen atom.

"Heterocycloalkyl" refers to a saturated or unsaturated ring having from 3 to about 20 member atoms and containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Heterocycloalkyl groups may contain more than one ring. Unless otherwise specified, heterocycloalkyl groups are monocyclic, bridged, or fused ring systems. Monocyclic heterocycloalkyl rings have from 4 to 7 member atoms. Bridged or bicyclic heterocycloalkyl rings have from 7 to 11 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,4-dioxanyl, 1,3-oxathiolanyl, 1,3-oxathianyl, 1,3-dithianyl, azetidinyl, azabicylo[3.2.1]octyl, azabicylo[3.3.1]nonyl, azabicylo[4.3.0]nonyl, oxabicylo[2.2.1]heptyl, and pthalimidyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. When the substituted group is C=O, then 2 hydrogens on the carbon atom in question have been replaced. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Therapeutically effective amount" is intended to include an amount of a compound of the present invention or an amount of the combination of compounds claimed effective to inhibit sEH in a host.

Unless otherwise stated, a "5- or 6-membered ring" refers to aromatic and heteroaromatic rings, as well as carbocyclic and heterocyclic rings, which may be partially or fully saturated. Examples of such rings include, but are not limited to furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl, cyclopentyl and cyclohexenyl.

Compounds

In one embodiment the invention is directed to compounds according to Formula A:

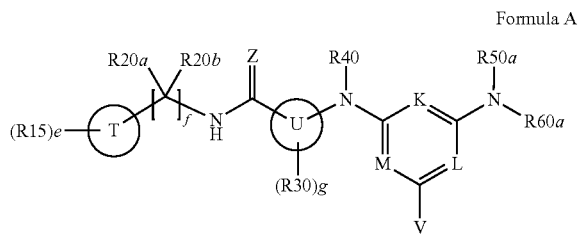

Formula A wherein.

T is phenyl, monocyclic heteroaryl, or C5-C6 cycloalkyl;

when T is phenyl or monocyclic heteroaryl each R15 is independently selected from the group consisting of: halo, —CN, Ra, Rl, Rm, —ORc, —C(O)ORd, —C(O)NRdRd, —NReRe, —NRdC(O)Rc, —NRdS(O$_2$)Ra, —SRc, —S(O$_2$)Ra, and —S(O$_2$)NRdRd;

when T is C5-C6 cycloalkyl each $R_{15}$ is independently selected from the group consisting of: Ra, —ORc, —C(O)ORd, —C(O)NRdRd, —NRdRd, and —NRdC(O)Rc;

e is an integer from 0 to 5;

each R20a is independently H or C1-C3 alkyl;

each R20b is independently H or C1-C3 alkyl;

f is 0, 1 or 2;

Z is O or S;

U is C3-C10 cycloalkyl;

each R30 is independently halo, C1-C6 alkyl, —ORc, or —SRc;

g is an integer from 0 to 6;

R40 is H, R41, or R42;

R41 is C1-C6 alkyl optionally substituted with one or more substituents selected from the group consisting of: CF$_3$, —ORc, —SRc, —NReRe, —C(O)ORd, —C(O)NRdRd, C3-C6 cycloalkyl, Rl, and Rm;

R42 is C3-C6 cycloalkyl optionally substituted with one or more substituents selected from the group consisting of: —ORc, —SRc, —NReRe, C1-C3 alkyl, and C1-C3 haloalkyl;

K, L, and M are each independently N or CR70 provided that at least one of K, L, and M is N;

V is H, halo, —OR80, or NR50bR60b;

R50a and R50b are each independently H, R51, R52, R53, R54, R55, —C(O)Rc, —C(O)NRdRd, —S(O$_2$)Ra, or —S(O$_2$)NRdRd;

each R51 is C1-C6 alkyl optionally substituted with one or more substituents selected from the group consisting of: halo, —ORa, —ORi, —ORj, —ORk, —SRa, —SRi, —SRj, —SRk, —C(O)ORd, —C(O)NReRe, —NReRe, Rg, Rh, Ri, and Rj;

each R52 is C3-C6 cycloalkyl optionally substituted with one or more substituents selected from the group consisting of: halo, —ORc, —SRc, —C(O)ORc, —C(O)NReRe, —NReRe, C1-C3 alkyl, and C1-C3 haloalkyl;

R53 is monocyclic heterocycloalkyl optionally substituted with one or more C1-C3 alkyl;

R54 is phenyl optionally substituted with one or more substituents selected from the group consisting of: halo, CN, Ra, —ORc, —C(O)ORd, —C(O)NRdRd, —NRdRd, —NRcC(O)Rc, —NRdS(O$_2$)Ra, —SRc, —S(O$_2$)Ra, and —S(O$_2$)NReRe;

R55 is monocyclic heteroaryl optionally substituted with one or more substituents selected from the group consisting of: halo, —CN, C1-C3 alkyl, C1-C3 haloalkyl, ORc, —SRc, —S(O$_2$)Ra, —S(O$_2$)NReRe, and NRdRd;

R60a and R60b are each independently H, R51, or R52; or

R50a and R60a and/or R50b and R60b, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, ORc, and NRfRf;

R70 is H, R71, or —ORb71;

R71 is C1-C6 alkyl optionally substituted with one or more substituents selected from the group consisting of: halo, —ORc, —SRc, —C(O)ORd, and —NReRe;

R80 is H or C1-C8 alkyl optionally substituted with one or more substituents selected from the group consisting of: halo, —ORc, —SRc, —NReRe, C3-C6 cycloalkyl, Rl, and Rj;

each Ra is independently C1-C6 alkyl optionally substituted with one or more substituents selected from the group consisting of: halo, —ORc, —SRc, —C(O)ORd, —C(O)NReRe, —NReRe, Rg, Rh, Ri, Rj;

each Rc is independently H, C1-C6 alkyl or C1-C6 haloalkyl;

each Rd is independently H or C1-C6 alkyl;

each Re is independently H, C1-C6 alkyl, CH$_2$—CF$_3$; or both Re groups, independently in each instance, taken together with the nitrogen atom to which they are attached form a saturated monocyclic ring having from 5 to 7 member atoms wherein said ring optionally contains one additional heteroatom as a member atom and wherein said ring is optionally substituted with one or more substituents selected from the group consisting of: C1-C3 alkyl, —ORd, and —NRfRf;

each Rf is independently H or C1-C3 alkyl;

each Rg is C3-C6 cycloalkyl optionally substituted with one or more substituents selected from the group consisting of: halo, —ORc, —SRc, —C(O)ORd, —C(O)NReRe, —NReRe, and C1-C3 alkyl;

each Rh is monocyclic heterocycloalkyl optionally substituted with one or more C1-C3 alkyl;

each Rl is phenyl optionally substituted with one or more substituents selected from the group consisting of: halo, —CN, C1-C3 alkyl, C1-C3 haloalkyl, —ORc, and —NReRe;

each Rj is monocyclic heteroaryl optionally substituted with one or more substituents selected from the group consisting of: halo, —CN, C1-C3 alkyl, C1-C3 haloalkyl, —ORc, and —NReRe;

each Rk is independently —CH$_2$—Rl or —CH$_2$—Rj;

each Rl is phenyl optionally substituted with one or more substituents selected from the group consisting of: halo, —CN, C1-C3 alkyl, C1-C3 haloalkyl, —ORc, —C(O)ORd, and —NRfRf; and each Rm is monocyclic heteroaryl optionally substituted with one or more substituents selected from the group consisting of: halo, —CN, C1-C3 alkyl, C1-C3 haloalkyl, —ORc, —C(O)ORd, and —NRfRf.

In another embodiment the invention is directed to compounds according to Formula I:

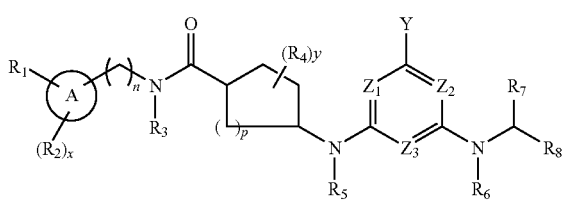

Formula I or a pharmaceutically acceptable salt thereof, wherein:

is a 6-membered aryl or heteroaryl ring;

$R_1$ is hydrogen, $CO_2H$, $CO_2(C_1-C_6)$alkyl, $CONR'R''$ wherein R' and R'' are each independently hydrogen or $(C_1-C_6)$alkyl, araalkyl, heteroaralkyl, $—(C_2-C_{10})$alkylene-NR'R'', $—(C_2-C_{10})$alkylene-OR', and $—O—(C_1-C_6)$alkyl, $—S—(C_1-C_6)$alkyl, any of which may be optionally substituted on carbon with 1, 2, or 3 halo;

each $R_2$ is if present independently halo, $(C_1-C_6)$alkyl, $—O—(C_1-C_6)$alkyl, $—S—(C_1-C_6)$alkyl, any of which may be optionally substituted on carbon with 1, 2, or 3 halo;

n is 0 or 1;

x is 0, 1, or 2;

$R_3$ is hydrogen or $(C_1-C_6)$alkyl;

p is 0, 1, 2, or 3;

each $R_4$ if present is independently halo, $(C_1-C_6)$alkyl, or $—O—(C_1-C_6)$alkyl, $—S—(C_1-C_6)$alkyl, any of which may be optionally substituted on carbon with 1, 2, or 3 halo, or taken together with the attached carbon forms C=O;

y is 0, 1, or 2;

$R_5$ is hydrogen or $(C_1-C_6)$alkyl;

$R_6$ is hydrogen or $(C_1-C_6)$alkyl;

$R_7$ is hydrogen, halo, or $(C_1-C_6)$alkyl; or $R_6$ and $R_7$ together with the atoms to which they are attached, form a 3-10 membered ring, optionally substituted on carbon with 1, 2, or 3 groups selected from halo, $(C_1-C_6)$alkyl, and $—O—(C_1-C_6)$alkyl, $—S—(C_1-C_6)$alkyl, any of which may be optionally substituted on carbon with 1, 2, or 3 halo, or taken together with the attached carbon forms C=O;

$R_8$ is hydrogen, halo, or $(C_1-C_6)$alkyl, or is

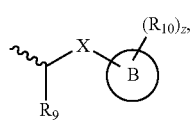

wherein " $\sim$ " indicates the point of attachment and wherein $R_9$ is hydrogen, halo, or $(C_1-C_6)$alkyl;

X is absent or is O, $S(O)_m$ wherein m is 0, 1, or 2, $—CH_2—S—$, $—CH_2—O—$, $—CH_2—NH—$, or $—CH_2—N(C_1-C_6)$alkyl-;

is $(C_3-C_6)$cycloalkyl, $(C_3-C_6)$heterocycloalkyl, aryl, or heteroaryl;

each $R_{10}$ if present is independently halo, $(C_1-C_6)$alkyl, $—O—(C_1-C_6)$alkyl, $—S—(C_1-C_6)$alkyl, any of which may be optionally substituted on carbon with 1, 2, or 3 halo, or taken together with the attached carbon forms C=O;

z is 0, 1, or 2;

at least one of $Z_1$, $Z_2$, and $Z_3$ are N and the others are $C—R_b$, wherein $R_b$ is hydrogen, halogen, $(C_1-C_6)$alkyl, or $(C_1-C_6)$alkoxy;

Y is H, halo, $OR_{11}$, or $NR_{11}R_{12}$;

$R_{11}$ is hydrogen or $(C_1-C_6)$alkyl; and $R_{12}$ is hydrogen, $(C_1-C_6)$alkyl, aryl, aralkyl, $(C_3-C_6)$cycloalkyl, -alkylene-$(C_3-C_6)$cycloalkyl, $(C_3-C_6)$heterocycloalkyl, -alkylene-$(C_3-C_6)$heterocycloalkyl, heteroaryl, heteroaralkyl, any of which may be optionally substituted on carbon with 1 or 2 groups selected from halo, $(C_1-C_6)$alkyl, $—O—(C_1-C_6)$alkyl, $—S—(C_1-C_6)$alkyl.

In another embodiment, the invention is directed to compounds according to Formula II:

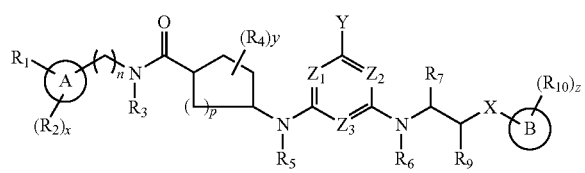

Formula II or a pharmaceutically acceptable salt thereof, wherein:

is a 6-membered aryl or heteroaryl ring;

$R_1$ is hydrogen, $CO_2H$, $CO_2(C_1-C_6)$alkyl, $CONR'R''$ wherein R' and R'' are each independently hydrogen or $(C_1-C_6)$alkyl, araalkyl, heteroaralkyl, $—(C_2-C_{10})$alkylene-NR'R'', $—(C_2-C_{10})$alkylene-OR', and $—O—(C_1-C_6)$alkyl, $—S—(C_1-C_6)$alkyl, any of which may be optionally substituted on carbon with 1, 2, or 3 halo;

each $R_2$ is if present independently halo, $(C_1-C_6)$alkyl, $—O—(C_1-C_6)$alkyl, $—S—(C_1-C_6)$alkyl, any of which may be optionally substituted on carbon with 1, 2, or 3 halo;

n is 0 or 1;

x is 0, 1, or 2;

$R_3$ is hydrogen or $(C_1-C_6)$alkyl;

p is 0, 1, 2, or 3;

each $R_4$ if present is independently halo, $(C_1-C_6)$alkyl, or $—O—(C_1-C_6)$alkyl, $—S—(C_1-C_6)$alkyl, any of which may be optionally substituted on carbon with 1, 2, or 3 halo, or taken together with the attached carbon forms C=O;

y is 0, 1, or 2;

$R_5$ is hydrogen or $(C_1-C_6)$alkyl;

$R_6$ is hydrogen or $(C_1-C_6)$alkyl;

$R_7$ is hydrogen, halo, or $(C_1-C_6)$alkyl;

$R_9$ is hydrogen, halo, or $(C_1-C_6)$alkyl;

X is absent or is O, S(O)$_m$ wherein m is 0, 1, or 2, —CH$_2$—S—, —CH$_2$—O—, —CH$_2$—NH—, or —CH$_2$—N(C$_1$-C$_6$)alkyl-;

$$\text{\textcircled{B}}$$

is (C$_3$-C$_6$)cycloalkyl, (C$_3$-C$_6$)heterocycloalkyl, aryl, or heteroaryl;

each R$_{10}$ if present is independently halo, (C$_1$-C$_6$)alkyl, —O—(C$_1$-C$_6$)alkyl, —S—(C$_1$-C$_6$)alkyl, any of which may be optionally substituted on carbon with 1, 2, or 3 halo, or taken together with the attached carbon forms C=O;

z is 0, 1, or 2;

at least one of Z$_1$, Z$_2$, and Z$_3$ are N and the others are C—R$_b$, wherein R$_b$ is hydrogen, halogen, (C$_1$-C$_6$)alkyl, or (C$_1$-C$_6$)alkoxy;

Y is H, halo, OR$_{11}$, or NR$_{11}$R$_{12}$;

R$_{11}$ is hydrogen or (C$_1$-C$_6$)alkyl; and

R$_{12}$ is hydrogen, (C$_1$-C$_6$)alkyl, aryl, aralkyl, (C$_3$-C$_6$)cycloalkyl, -alkylene-(C$_3$-C$_6$)cycloalkyl, (C$_3$-C$_6$)heterocycloalkyl, -alkylene-(C$_3$-C$_6$)heterocycloalkyl, heteroaryl, heteroaralkyl, any of which may be optionally substituted on carbon with 1 or 2 groups selected from halo, (C$_1$-C$_6$)alkyl, —O—(C$_1$-C$_6$)alkyl, —S—(C$_1$-C$_6$)alkyl.

In another embodiment, the invention is directed to compounds according to Formula III:

Formula III or a pharmaceutically acceptable salt thereof, wherein:

$$\text{\textcircled{A}}$$

is a 6-membered aryl or heteroaryl ring;

R$_1$ is hydrogen, CO$_2$H, CO$_2$(C$_1$-C$_6$)alkyl, CONR'R" wherein R' and R" are each independently hydrogen or (C$_1$-C$_6$)alkyl, araalkyl, heteroaralkyl, —(C$_2$-C$_{10}$)alkylene-NR'R", —(C$_2$-C$_{10}$)alkylene-OR', and —O—(C$_1$-C$_6$)alkyl, —S—(C$_1$-C$_6$)alkyl, any of which may be optionally substituted on carbon with 1, 2, or 3 halo;

each R$_2$ is if present independently halo, (C$_1$-C$_6$)alkyl, —O—(C$_1$-C$_6$)alkyl, —S—(C$_1$-C$_6$)alkyl, any of which may be optionally substituted on carbon with 1, 2, or 3 halo;

n is 0 or 1;

x is 0, 1, or 2;

R$_3$ is hydrogen or (C$_1$-C$_6$)alkyl;

p is 0, 1, 2, or 3;

each R$_4$ if present is independently halo, (C$_1$-C$_6$)alkyl, or —O—(C$_1$-C$_6$)alkyl, —S—(C$_1$-C$_6$)alkyl, any of which may be optionally substituted on carbon with 1, 2, or 3 halo, or taken together with the attached carbon forms C=O;

y is 0, 1, or 2;

R$_5$ is hydrogen or (C$_1$-C$_6$)alkyl;

$$\text{\textcircled{C}}$$

is a 3-10 membered ring, optionally containing 1 additional heteroatom selected from O, S(O)$_m$ wherein m is 0, 1, or 2, or NR", wherein R" is hydrogen or (C$_1$-C$_6$)alkyl, and wherein " $\sim\sim\sim$ " indicate points of attachment;

each R$_{13}$ if present is independently halo, (C$_1$-C$_6$)alkyl, or —O—(C$_1$-C$_6$)alkyl, —S—(C$_1$-C$_6$)alkyl, any of which may be optionally substituted on carbon with 1, 2, or 3 halo, or taken together with the attached carbon forms C=O;

w is 0, 1, or 2;

Y is H, halo, OR$_{11}$, or NR$_{11}$R$_{12}$;

R$_{11}$ is hydrogen or (C$_1$-C$_6$)alkyl; and

R$_{12}$ is hydrogen, (C$_1$-C$_6$)alkyl, aryl, aralkyl, (C$_3$-C$_6$)cycloalkyl, alkylene-(C$_3$-C$_6$)cycloalkyl, (C$_3$-C$_6$)heterocycloalkyl, alkylene-(C$_3$-C$_6$)heterocycloalkyl, heteroaryl, heteroaralkyl, any of which may be optionally substituted on carbon with 1 or 2 groups selected from halo, (C$_1$-C$_6$)alkyl, —O—(C$_1$-C$_6$)alkyl, —S—(C$_1$-C$_6$)alkyl.

In another embodiment, the invention is directed to a compound of Formula I, II, or III, which is:

-continued
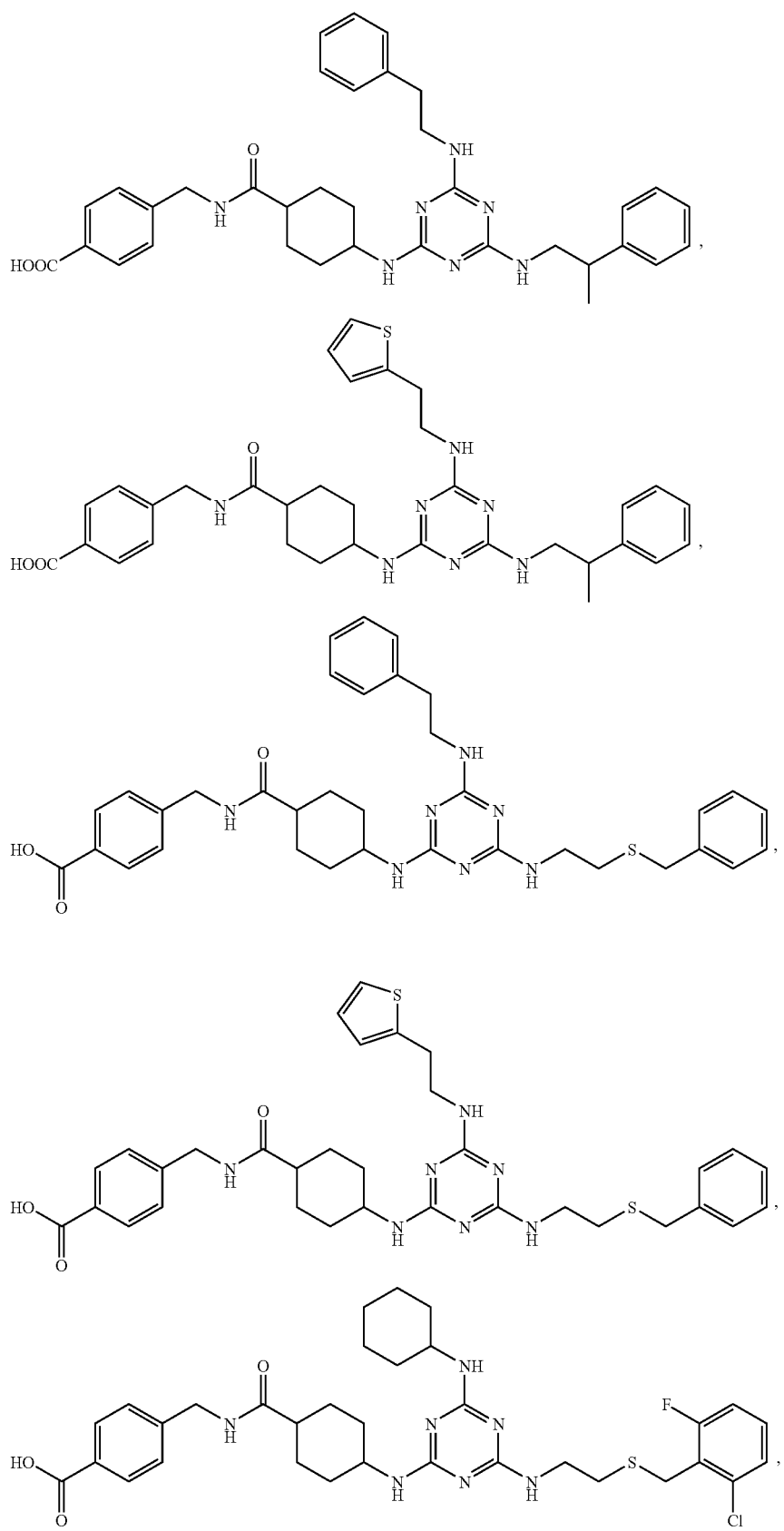

-continued
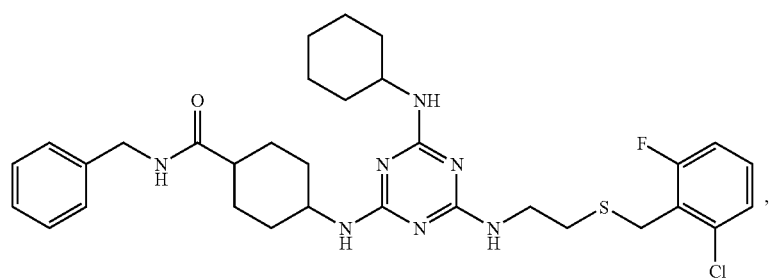
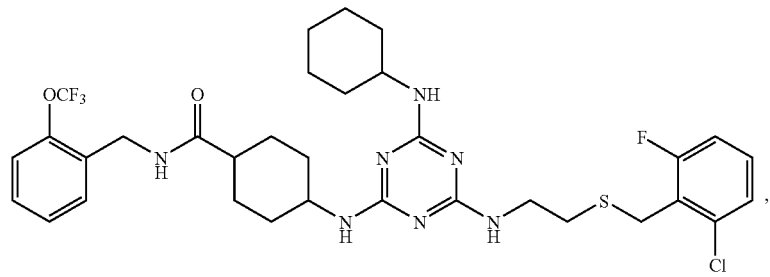
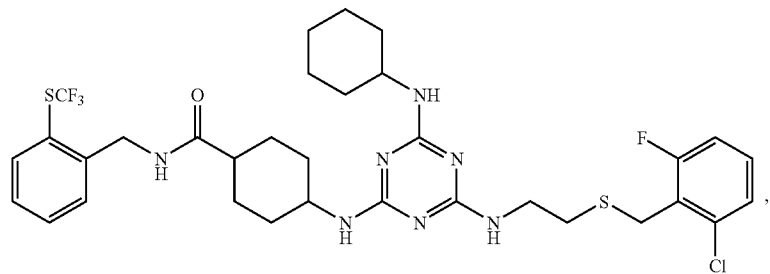
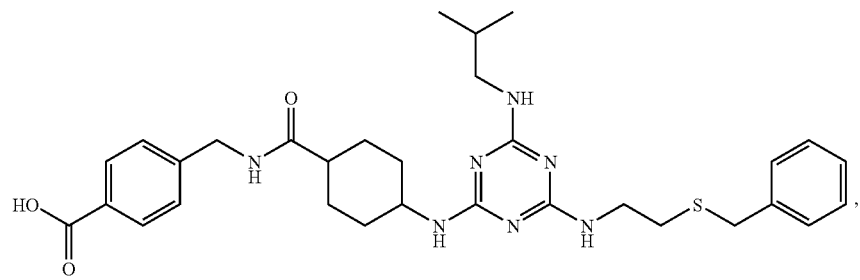
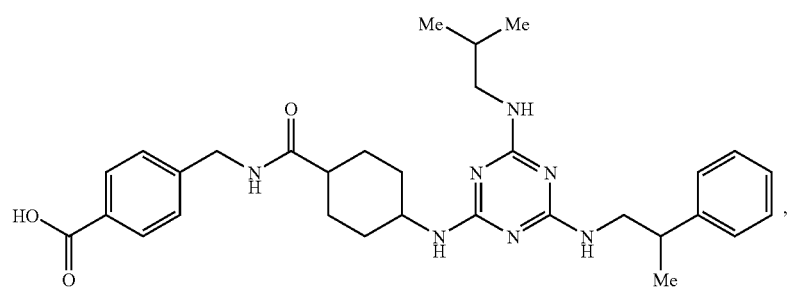
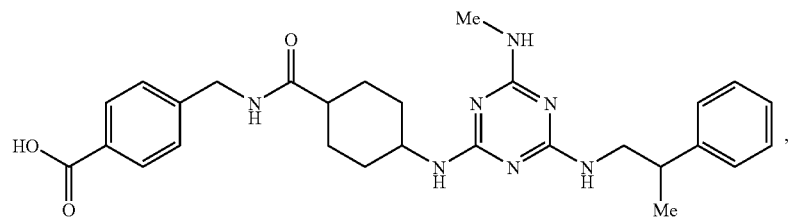

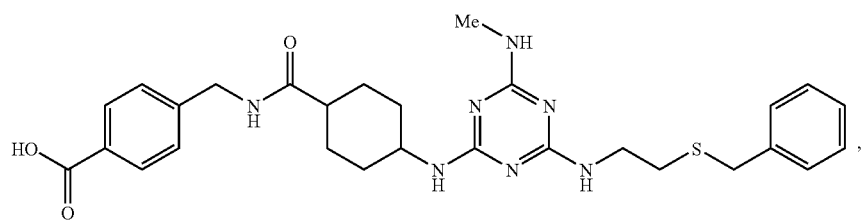,
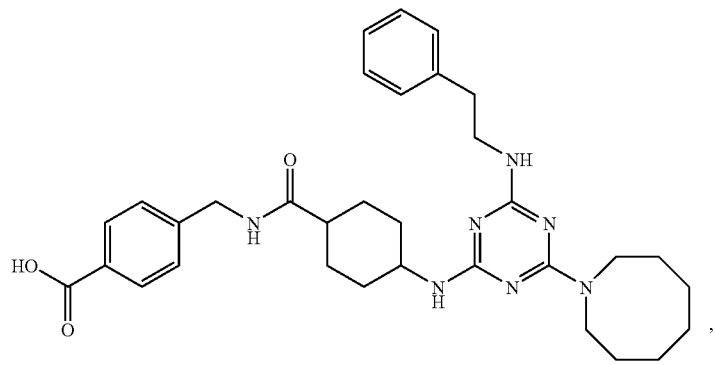,
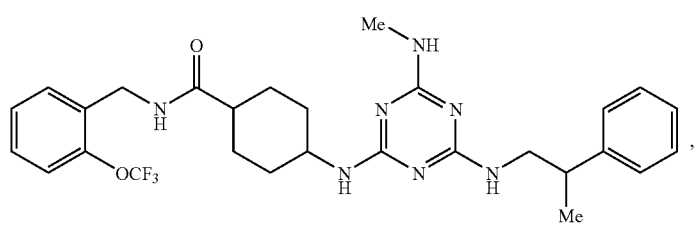,
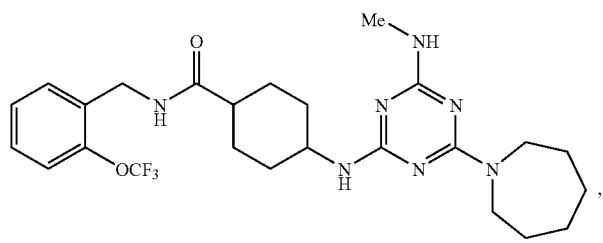,
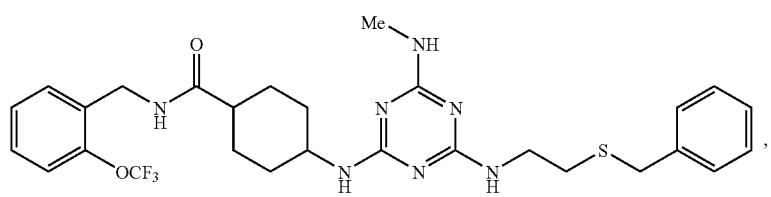,
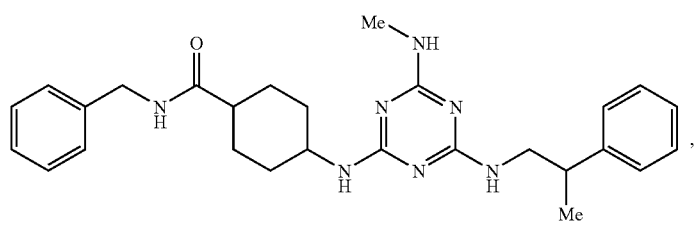,
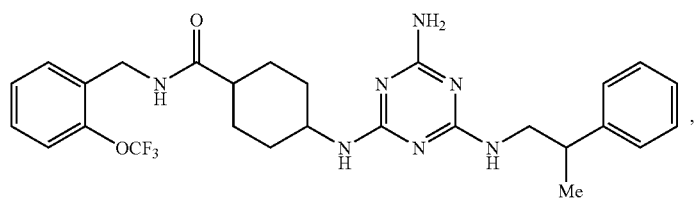,

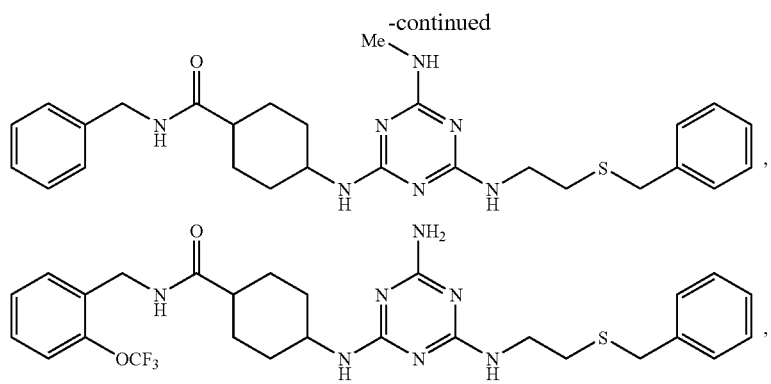

or a pharmaceutically acceptable salt thereof.

In another embodiment, the invention is directed to a pharmaceutical composition, comprising a pharmaceutically acceptable carrier and a therapeutically effective amount of a compound of Formula I or a pharmaceutically acceptable salt thereof.

In another embodiment, the invention is directed to a method for treating hypertension disorder, comprising: administering to a patient in need thereof a therapeutically effective amount of a compound of Formula I or a pharmaceutically acceptable salt form thereof.

In another embodiment, the invention is directed to a method for treating an inflammatory disorder, comprising: administering to a patient in need thereof a therapeutically effective amount of a compound of Formula I or a pharmaceutically acceptable salt form thereof.

In another embodiment, the invention is directed to a method of treating a condition or disease mediated by sEH in a mammal, comprising: administering to the mammal in need of such treatment a therapeutically effective amount of a compound of Formula I or a pharmaceutically acceptable salt form thereof.

In another embodiment, the invention is directed to a process for making a compound of Formula I comprising the steps outlined in Schemes 1-3 infra.

We turn now to a compound of formula I.

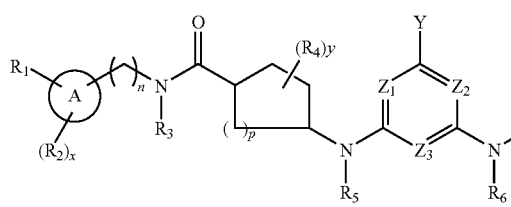

A specific value for (A)

is phenyl. Another specific value for (A)

is pyridyl.

A specific value for $R_1$ is hydrogen. Another specific value for $R_1$ is $CO_2H$. Another specific value for $R_1$ is $CO_2Me$. Another specific value for $R_1$ is methoxy. Another specific value for $R_1$ is ethoxy. Another specific value for $R_1$ is $SCF_3$. Another specific value for $R_1$ is $OCF_3$. Another specific value for $R_1$ is $CF_3$.

A specific value for each $R_2$ (if present) is, independently, chloro. Another specific value for $R_2$ is fluoro. Another specific value for $R_2$ is methyl. Another specific value for $R_2$ is ethyl. Another specific value for $R_2$ is methoxy. Another specific value for $R_2$ is ethoxy. Another specific value for $R_2$ is thiomethyl. Another specific value for $R_2$ is trifluoromethyl. Another specific value for $R_2$ is trifluoromethoxy.

A specific value for x is 0. Other specific values for x are 1 or 2.

A specific value for n is 0. Another specific value for n is 1.

A specific value for $R_3$ is hydrogen. Another specific value for $R_3$ is methyl.

A specific value for p is 0. Other specific values for p include 1, 2, and 3.

A specific value for each $R_4$ (if present) is, independently, chloro. Another specific value for $R_4$ is fluoro. Another specific value for $R_4$ is methyl. Another specific value for $R_4$ is ethyl. Another specific value for $R_4$ is methoxy. Another specific value for $R_4$ is ethoxy. Another specific value for $R_4$ is thiomethyl. Another specific value for $R_4$ is trifluoromethyl. Another specific value for $R_4$ is trifluoromethoxy.

A specific value for y is 0. Other specific values for y are 1 or 2.

A specific value for $R_5$ is hydrogen. Another specific value for $R_5$ is methyl.

A specific value for $R_6$ is hydrogen. Another specific value for $R_6$ is methyl.

A specific value for $R_7$ is hydrogen. Another specific value for $R_7$ is chloro, fluoro, bromo, or iodo. Another specific value for $R_7$ is methyl.

Alternatively, $R_6$ and $R_7$ may be taken together with the atoms to which they are attached to form a 3-10 membered ring

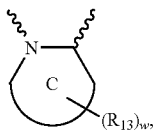

optionally containing 1 additional heteroatom selected from O, S(O)$_m$ wherein m is 0, 1, or 2, or NR''', wherein R''' is hydrogen or (C$_1$-C$_6$)alkyl, and optionally substituted on carbon with halo, (C$_1$-C$_6$)alkyl, —O—(C$_1$-C$_6$)alkyl or —S—(C$_1$-C$_6$)alkyl, any of which may be optionally substituted on carbon with 1, 2, or 3 halo, or taken together with the attached carbon forms C=O. Thus, a specific value for

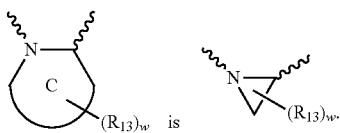

Other specific values for

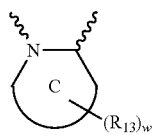

include

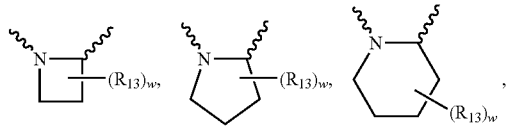

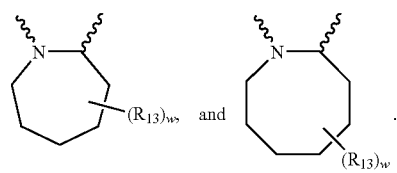

These specific values for

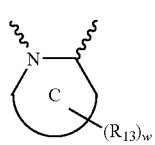

may be optionally substituted on carbon with 1, 2, or 3 groups selected from chloro, fluoro, methyl, trifluoromethyl, methoxy, and trifluoromethoxy.

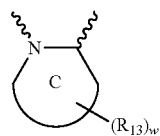

In the structures for above, a specific value for each R$_{13}$ (if present) is, independently, chloro. Another specific value for R$_{13}$ is fluoro. Another specific value for R$_{13}$ is methyl. Another specific value for R$_{13}$ is ethyl. Another specific value for R$_{13}$ is methoxy. Another specific value for R$_{13}$ is ethoxy. Another specific value for R$_{13}$ is thiomethyl. Another specific value for R$_{13}$ is trifluoromethyl. Another specific value for R$_{13}$ is trifluoromethoxy. Another specific value for R$_{13}$ is trifluorothiomethyl.

A specific value for w is 0. Other specific values for w are 1 or 2.

A specific value for R$_8$ is hydrogen. Another specific value for R$_8$ is chloro. Another specific value for R$_8$ is fluoro. Another specific value for R$_8$ is methyl. Another specific value for R$_8$ is trifluoromethyl. Another specific value for R$_8$ is methoxy. Another specific value for R$_8$ is trifluoromethoxy. Another specific value for R$_8$ is trifluorothiomethyl.

Another specific value for R$_8$ is

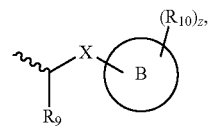

wherein "∼" indicates the point of attachment. Thus, when R$_8$ is

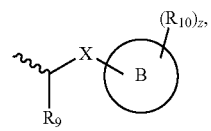

a specific value for R$_9$ is hydrogen. Another specific value for R$_9$ is methyl.

When R$_8$ is

X may be absent. Alternatively, a specific value for X is O. Another specific value for X is S, SO, or SO$_2$. Other specific values for X include —CH$_2$—S—, CH$_2$—O—, CH$_2$—NH—, or CH$_2$—NMe. When X is —CH$_2$—S—, CH$_2$—O—, CH$_2$—NH—, or —CH$_2$—NMe, X may be attached to

in either orientation (that is, as depicted for —CH$_2$—S—, as

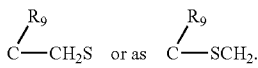

When R$_8$ is

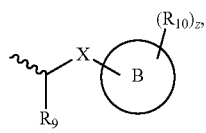

specific value for

is phenyl. Another a specific value for

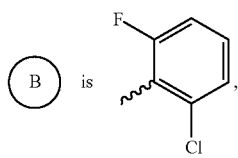

wherein " ~ " indicates the point of attachment.

Another specific value for

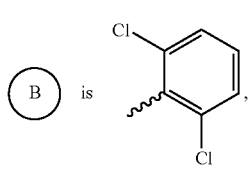

wherein " ~ " indicates the point of attachment.

When R$_8$ is

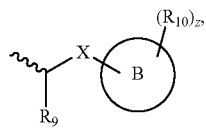

a specific value for each R$_{10}$ (if present) independently is chloro. Another specific value for R$_{10}$ is fluoro. Another specific value for R$_{10}$ is methyl. Another specific value for R$_{10}$ is ethyl. Another specific value for R$_{10}$ is methoxy. Another specific value for R$_{10}$ is ethoxy. Another specific value for R$_{10}$ is thiomethyl. Another specific value for R$_{10}$ is trifluoromethyl. Another specific value for R$_{10}$ is trifluoromethoxy. Another specific value for R$_{10}$ is trifluorothiomethyl.

When R$_8$ is

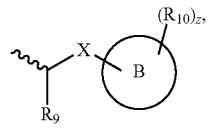

a specific value for z is 0. Other specific values for z include 1 and 2.

As indicated previously, in

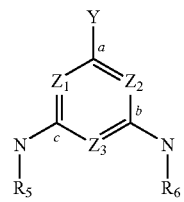

at least one of Z$_1$, Z$_2$, and Z$_3$ in

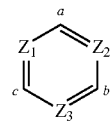

are N and the others are C—R$_b$, wherein R$_b$ is hydrogen, halogen, (C$_1$-C$_6$)alkyl, (C$_1$-C$_6$)alkoxy, or NR'R", wherein R' and R" are each independently hydrogen or (C$_1$-C$_6$)alkyl. Thus specific values for

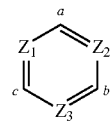

include

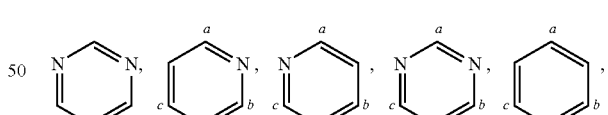

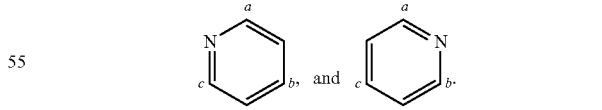

A specific value for Y is hydrogen. Other specific values for Y are chloro and fluoro. Other specific values for Y is OR$_{11}$ and NR$_{11}$R$_{12}$.

A specific value for R$_{11}$ is hydrogen. Another specific value for R$_{11}$ is methyl.

A specific value for R$_{12}$ is hydrogen. Other specific values for R$_{12}$ include (C$_1$-C$_6$)alkyl, aryl, aralkyl, (C$_3$-C$_6$)cycloalkyl, alkylene-(C$_3$-C$_6$)cycloalkyl, (C$_3$-C$_6$)heterocycloalkyl, alkylene-(C$_3$-C$_6$)heterocycloalkyl, heteroaryl, heteroaralkyl, any of which may be optionally substituted on carbon with 1 or 2 groups selected from halo, $(C_1-C_6)$alkyl, —O—$(C_1-C_6)$alkyl, —S—$(C_1-C_6)$alkyl. Thus, specific values for $R_{12}$ include methyl, ethyl, propyl, isopropyl, butyl, isobutyl, secbutyl, cyclohexyl, —CH$_2$CH$_2$-phenyl, —CH$_2$CH$_2$-phenyl substituted on the phenyl ring with 1 or 2 groups independently selected from the group consisting of chlorine, fluorine, and bromine, —CH$_2$CH$_2$-thiophene, and —CH$_2$CH$_2$-thiophene substituted on the thiophene ring with 1 or 2 groups independently selected from the group consisting of chlorine, fluorine, and bromine.

A specific group of compounds of the invention are compounds of Formula I-A

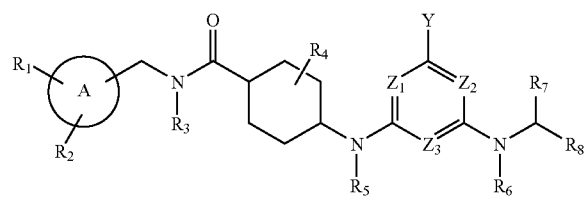

I-A or a pharmaceutically acceptable salt thereof.

A specific group of compounds of the invention are compounds of Formula I-B

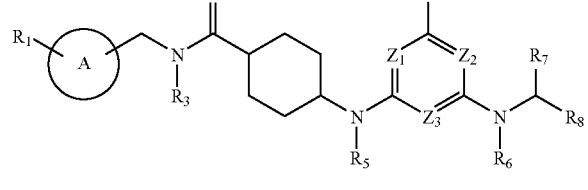

I-B or a pharmaceutically acceptable salt thereof.

A specific group of compounds of the invention are compounds of Formula I-C

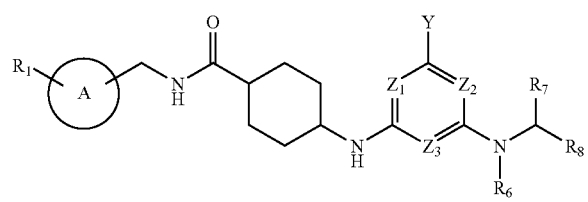

I-C

A specific group of compounds of the invention are compounds of Formula I-D

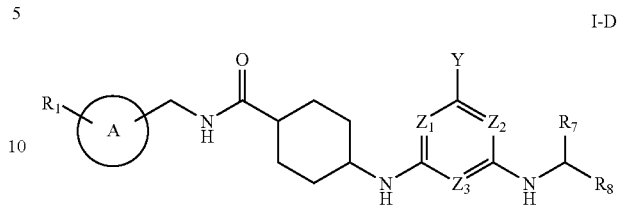

I-D or a pharmaceutically acceptable salt thereof.

A specific group of compounds of the invention are compounds of Formula II-A

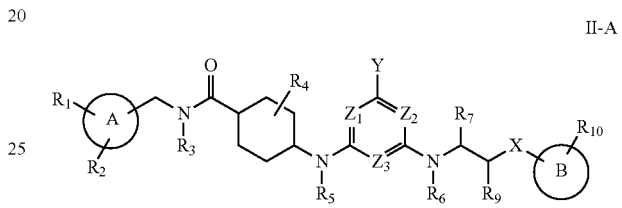

II-A or a pharmaceutically acceptable salt thereof.

A specific group of compounds of the invention are compounds of Formula II-B

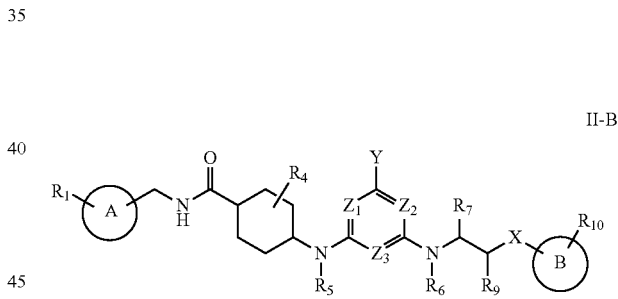

II-B or a pharmaceutically acceptable salt thereof.

A specific group of compounds of the invention are compounds of Formula II-C

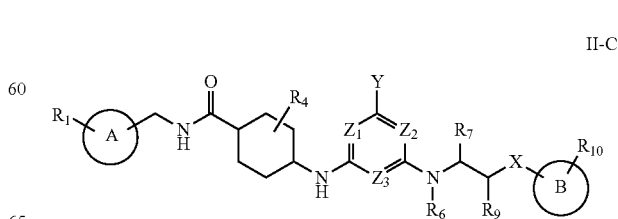

II-C

A specific group of compounds of the invention are compounds of Formula II-D

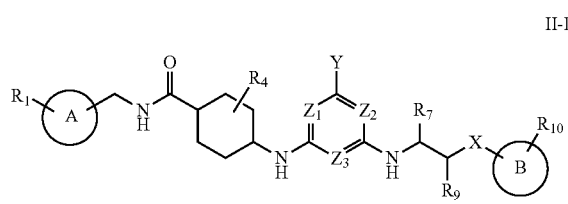

II-D or a pharmaceutically acceptable salt thereof.

A specific group of compounds of the invention are compounds of Formula II-E

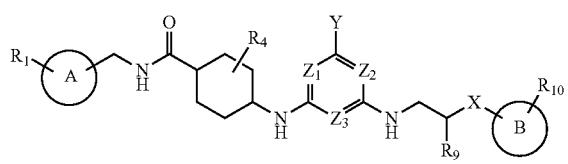

II-E or a pharmaceutically acceptable salt thereof.

A specific group of compounds of the invention are compounds of Formula III-A

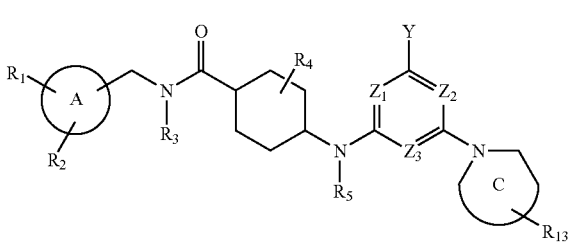

III-A or a pharmaceutically acceptable salt thereof.

A specific group of compounds of the invention are compounds of Formula III-B

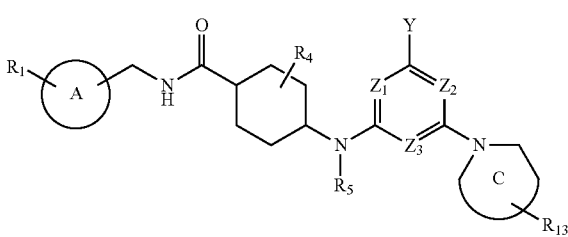

III-B or a pharmaceutically acceptable salt thereof.

A specific group of compounds of the invention are compounds of Formula III-C

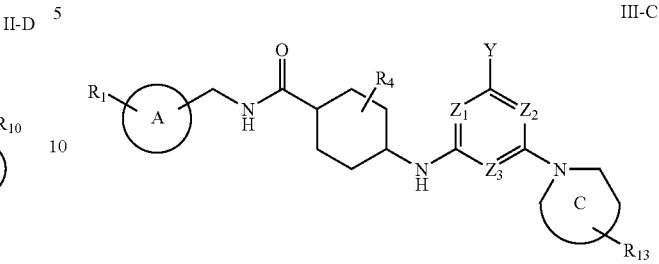

III-C or a pharmaceutically acceptable salt thereof.

The meaning of any functional group or substituent thereon at any one occurrence in any Formula herein, or any subformula thereof, is independent of its meaning, or any other functional group's or substituent's meaning, at any other occurrence, unless stated otherwise.

When a bond to a substituent is shown to cross a bond connecting two atoms in a ring, that substituent may be bonded to any atom on the ring. When a substituent is listed without indicating the atom to which such substituent is bonded to the rest of the compound of a given Formula, that substituent may be bonded to any atom of that substituent. Combinations of substituents and/or variables are permissible only if such combinations result in stable compounds.

The compounds according to any Formula herein may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a Formula, or in any chemical structure illustrated herein, is not specified the Formula/structure is intended to encompass any stereoisomer and all mixtures thereof. Thus, compounds according to any Formula herein containing one or more chiral center may be used as racemic mixtures, enantiomerically enriched mixtures, or as enantiomerically pure individual stereoisomers.

Individual stereoisomers of a compound according to any Formula herein which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzamatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to any Formula herein may also contain double bonds or other centers of geometric asymmetry. Where the stereochemistry of a center of geometric asymmetry present in a Formula, or in any chemical structure illustrated herein, is not specified, the Formula/structure is intended to encompass the trans (E) geometric isomer, the cis (Z) geometric isomer, and all mixtures thereof. Likewise, all tautomeric forms are also included in a Formula/structure whether such tautomers exist in equilibrium or predominately in one form.

In certain embodiments, compounds according to any Formula herein may contain an acidic functional group and are therefore capable of forming pharmaceutically-acceptable base addition salts by treatment with a suitable base. In certain other embodiments, compounds according to any Formula herein may contain a basic functional group and are therefore capable of forming pharmaceutically-acceptable acid addition salts by treatment with a suitable acid. Thus, the skilled artisan will appreciate that pharmaceutically-acceptable salts of the compounds according to any Formula herein may be prepared. Indeed, in certain embodiments of the invention, pharmaceutically-acceptable salts of the compounds according to any Formula herein may be preferred over the respective free base or free acid because such salts impart greater stability or solubility to the molecule thereby facilitating formulation into a dosage form. Accordingly, the invention is further directed to pharmaceutically-acceptable salts of the compounds according to any Formula herein.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, the term "compounds of the invention" means both the compounds according to any Formula herein and the pharmaceutically-acceptable salts thereof. The term "a compound of the invention" also appears herein and refers to both a compound according to any Formula herein and its pharmaceutically-acceptable salts.

In the solid state, compounds of the invention can exist in crystalline, semi-crystalline and amorphous forms, as well as mixtures thereof. The skilled artisan will appreciate that pharmaceutically-acceptable solvates of a compound of the invention may be formed wherein solvent molecules are incorporated into the solid-state structure during crystallization. Solvates may involve water or nonaqueous solvents, or mixtures thereof. In addition, the solvent content of such solvates can vary in response to environment and upon storage. For example, water may displace another solvent over time depending on relative humidity and temperature.

Solvates wherein water is the solvent that is incorporated into the solid-state structure are typically referred to as "hydrates." Solvates wherein more than one solvent is incorporated into the solid-state structure are typically referred to as "mixed solvates". Solvates include "stoichiometric solvates" as well as compositions containing variable amounts of solvent (referred to as "non-stoichiometric solvates"). Stoichiometric solvates wherein water is the solvent that is incorporated into the solid-state structure are typically referred to as "stoichiometric hydrates", and non-stoichiometric solvates wherein water is the solvent that is incorporated into the solid-state structure are typically referred to as "non-stoichiometric hydrates". The invention includes both stoichiometric and non-stoichiometric solvates.

In addition, crystalline forms of a compound of the invention, including solvates thereof, may contain solvent molecules, which are not incorporated into the solid-state structure. For example, solvent molecules may become trapped in the crystals upon isolation. In addition, solvent molecules may be retained on the surface of the crystals. The invention includes such forms.

The skilled artisan will further appreciate that compounds of the invention, including solvates thereof, may exhibit polymorphism (i.e. the capacity to occur in different crystalline packing arrangements). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different IR spectra and X-ray powder diffraction patterns, which may be used for identification. Polymorphs may also exhibit different melting points, which may be used for identification. The skilled artisan will appreciate that different polymorphs may be produced, for example, by changing or adjusting the reaction conditions or reagents, used in making the compound. For example, changes in temperature, pressure, or solvent may result in the production of different polymorphs. In addition, one polymorph may spontaneously convert to another polymorph under certain conditions.

COMPOUND PREPARATION AND EXAMPLES

The compounds of the invention may be prepared using conventional organic syntheses. Suitable synthetic routes are depicted below in the following general reaction schemes. All functional groups are as defined above unless otherwise defined. Starting materials and reagents depicted below in the general reaction schemes are commercially available or can be made from commercially available starting materials using methods known by those skilled in the art.

The skilled artisan will appreciate that in certain instances the order of reactions depicted below in the general reaction schemes may be changed. The skilled artisan will further appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Example compounds illustrating the invention are also provided below. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Scheme i

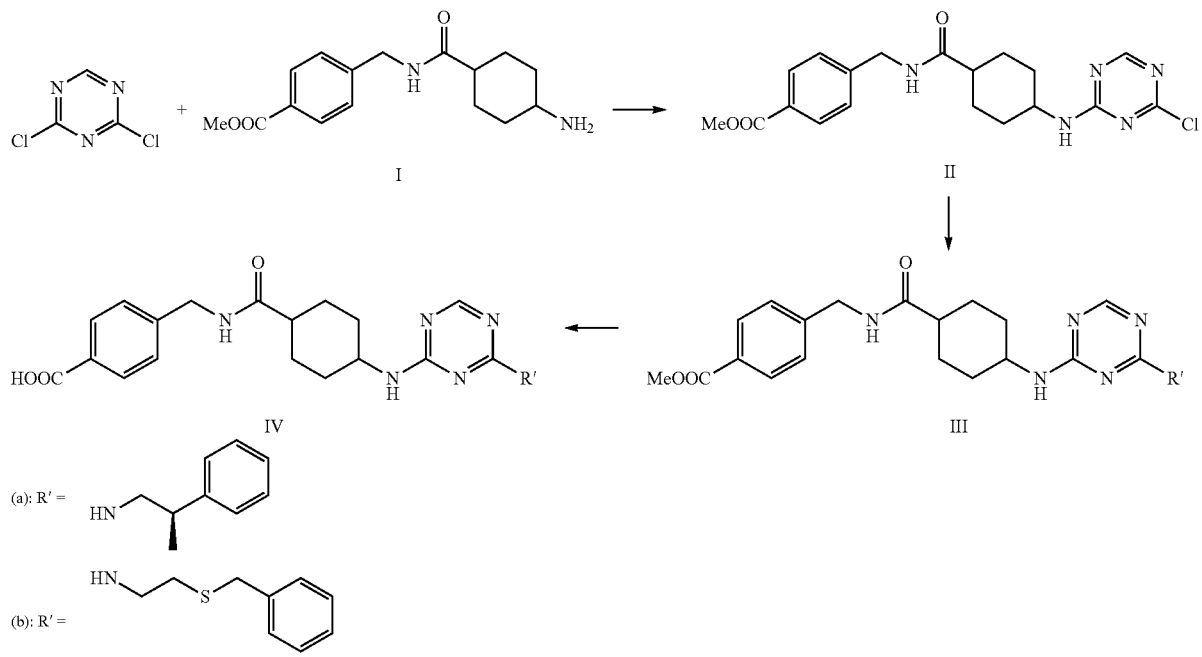

Preparation of Compound I

A solution of 4-(Boc-amino)cyclohexanecarboxylic acid (2.0 g, 8.22 mmol, 1 equivalent), methyl 4-(aminomethyl)benzoate hydrochloride (1.89 g, 9.37 mmol, 1.14 equivalents) and DMAP (200.8 mg, 1.644 mmol, 0.2 equivalent) in methylene chloride (50 mL) was cooled with stirring in an ice bath. DIEA (1.79 mL, 10.275 mmol, 1.25 equivalents) was added, followed by addition of EDCl (1.97 g, 10.275 mmol, 1.25 equivalents). The reaction mixture was stirred at 0° C. for 2 hours and at room temperature for 3 hours. The solution was diluted with methylene chloride (50 mL), which was further washed with saturated sodium bicarbonate, water, salt and dried over $Mg_2SO_4$. The solvent was removed in vacuo to give the crude compound which was further purified by silica chromatography (60%-70% EtOAc in Hexane) to give the desired product (2.97 g, 92.5%). This compound (2.97 g) was treated with 50% TFA in dichloromethane (80 ml) at room temperature for 25 minutes. The reaction mixture was condensed to give the desired compound as the TFA salt as a light yellow oil. MS: calculated for $C16H22N2O3+H^+291.16$, found 291.11.

Preparation of Compound II 2,4-Dichlorotriazine (96.6 mg, 0.612 mmol, 1 eq) was mixed with $CH_3CN/H_2O$ (1/1, 6 mL) in an ice bath. Compound I as the TFA salt (272 mg, 0.673 mmol, 1.1 equivalents) was added. The pH of the reaction mixture was adjusted to about 9 by adding dropwise 1N NaOH. After the addition, the reaction mixture was determined to be complete based on LC-MS monitoring. The crude product was used directly in the next step in the same reaction vessel.

General Procedure for the Preparation of Compound III

To the reaction mixture from the preparation of compound II (1 ml, approximately 0.1 mmol) was added a primary or secondary amine (5 equivalents). The reaction mixture was heated at 80° C. and was monitored by LC-MS. After 2 to 3 hours, the reaction was completed. The organic solvent was evaporated and the crude compound was acidified and purified with RP-HPLC.

Preparation of Compound III (a)

Crude compound II (approximately 0.1 mmol) in $CH_3CN/H_2O$ (1/1, 1 ml) was treated with (R)-(+)-beta-methylphenethylamine (67.7 mg, 0.5 mmol, 5 equivalents) at 80° C. for 2 hours. The crude was purified with RP-HPLC (Luna 5μ, C8(2), 100×21 mm, 20-65% $CH_3CN/H_2O$, 0.1% TFA, 17 min) to give the desired product (2.2 mg). MS: calculated for $C28H34N6O3+H^+503.27$, found 503.39.

Preparation of Compound III (b)

To crude compound II (~0.1 mmol) in $CH_3CN/H_2O$ (1/1, 1 ml) was added S-benzylcysteamine hydrochloride (101.9 mg, 0.5 mmol, 5 equivalents) and $Et_3N$ (84 μl, 0.6 mmol, 6 equivalents). The reaction mixture was heated at 80° C. for 2 hours. The crude was purified with RP-HPLC (Luna 5μ C8(2), 100×21 mm, 20-65% $CH_3CN/H_2O$, 0.1% TFA, 17 min) to give the desired product (4 mg). MS: calculated for $C28H34N6O3S+H^+535.24$, found 535.33.

General Procedure for the Preparation of Compound IV

To a solution of compound III (0.044 mmol, 1 equivalent) in MeOH (0.4 mL) was added 1N NaOH (0.2 mL). The reaction mixture was stirred at room temperature for 2 to 3 hours. The reaction was monitored with LC-MS. The solution was neutralized with 1N HCl and the crude product was purified with RP-HPLC.

Preparation of Compound IV (a)

Compound III(a) (approximately 2.2 mg) in MeOH (0.4 mL) was treated with 1N NaOH (0.2 mL) to give compound IV(a) (2 mg). The product was purified with RP-HPLC (Luna 5μ, C8(2), 100×21 mm, 10-65% $CH_3CN/H_2O$, 0.1% TFA, 20 min). MS: calculated for $C27H32N6O3+H^+489.25$, found 489.4.

Preparation of Compound IV (b)

Compound III(b) (approximately 4 mg) in MeOH (0.4 mL) was treated with 1N NaOH (0.2 mL) to give compound IV(b) (3.4 mg, 87% yield). The product was purified with RP-HPLC (Luna 5μ, C8(2), 100×21 mm, 10-65% $CH_3CN/H_2O$, 0.1% TFA, 20 min). MS: calculated for $C_{27}H_{32}N_6O_3S+H^+$ 521.23, found 521.3.

General Procedure for the Preparation of Compound V

A mixture of cyanuric chloride (1.22 mmol, 1 equivalent) in $CH_3CN/H_2O$ (1/1, 2 mL) was cooled to 0° C. A primary or secondary amine (1 equivalent) was added. The reaction mixture was adjusted to a pH of about 9-10 using 1N NaOH. The pH was kept at about 9-10 for 30 minutes. LC-MS was used to monitor the reaction. The crude product was used for the next amine addition in the same reaction vessel.

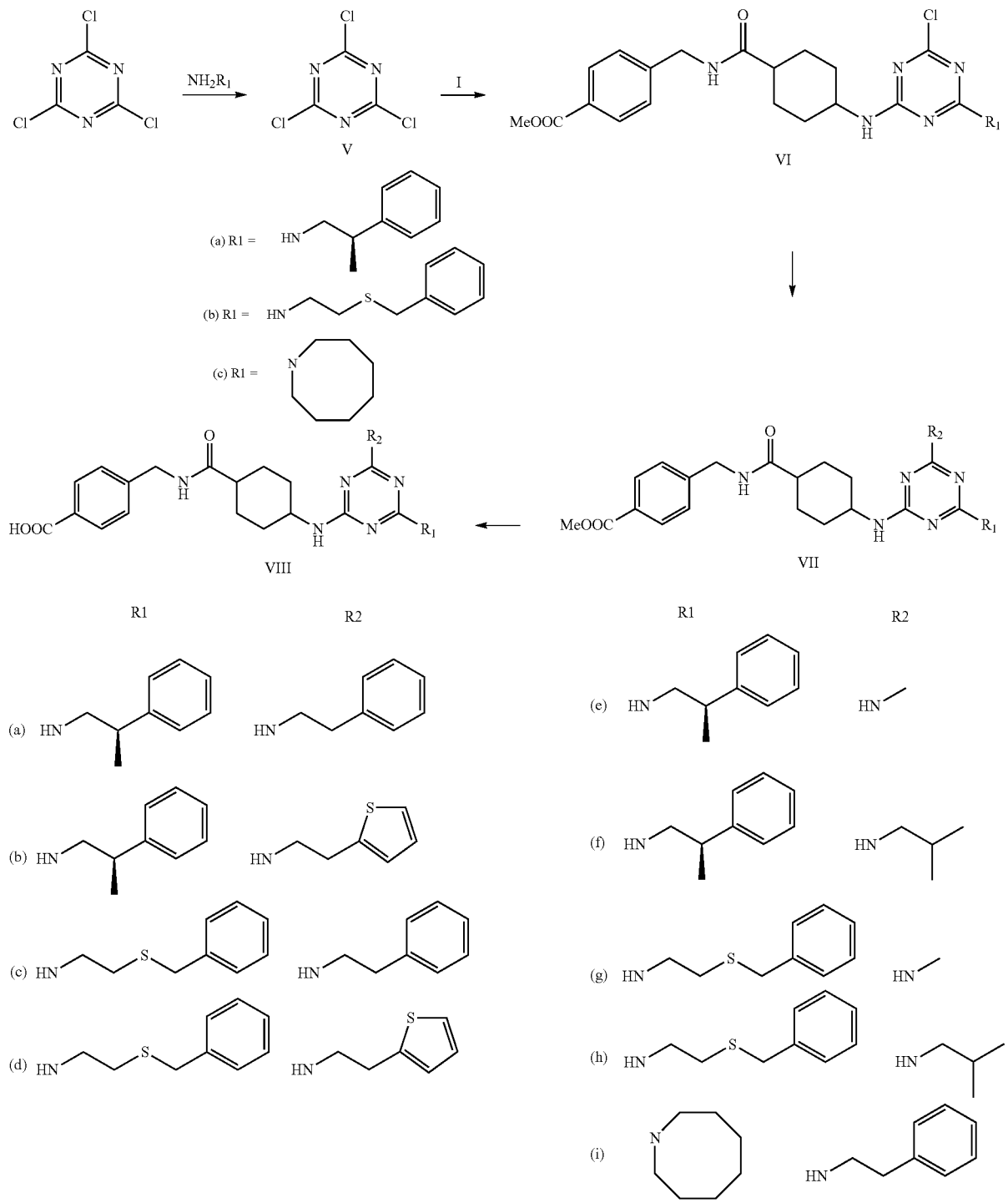

Preparation of Compound V(a)

Following the above general procedure, cyanuric chloride (50 mg, 0.27 mmol) was allowed to undergo reaction with (R)-(+)-beta-methylphenethylamine (36.7 mg, 0.27 mmol, 1 equivalent). MS: calculated for C12H12C12N4+H$^+$283.04, found 283.12.

Preparation of Compound V(b)

Following the above general procedure, cyanuric chloride (50 mg, 0.27 mmol) was allowed to undergo reaction with S-benzylcysteamine hydrochloride (55.2 mg, 0.27 mmol, 1 equivalent). MS: calculated for C12H12C12N4S+H$^+$315.02, found 315.01.

Preparation of Compound V(c)

Following the above general procedure, cyanuric chloride (50 mg, 0.27 mmol) was allowed to undergo reaction with heptamethyleneimine (30.7 mg, 0.27 mmol, 1 equivalent). MS: calculated for C10H14Cl$_2$N4+H$^+$260.06, found 261.17.

General Procedure for the Preparation of Compound VI

To crude compound V (0.27 mmol, 1 equivalent) in CH$_3$CN/H$_2$O (1/1, 2 mL) was added compound I as the TFA salt (0.27 mmol, 1 equivalent). 1N NaOH was added to the reaction to adjust the pH to about 10. The reaction mixture was stirred at room temperature for 4 hours, while the pH was retained between 9 and 10. Crude compound VI was used directly in the next step.

Preparation of Compound VI(a)

Following the above general procedure, crude compound V(a) (0.27 mmol) in CH$_3$CN/H$_2$O (1/1, 2 mL) was allowed to undergo reaction with compound I (131.42 mg, 0.32 mmol, 1.2 equivalents). MS: calculated for C28H33ClN6O3+H$^+$ 537.23, found 537.31.

Preparation of Compound VI(b)

Following the above general procedure, crude compound V(b) (0.27 mmol) in CH$_3$CN/H$_2$O (1/1, 2 mL) was allowed to undergo reaction with compound I (131.42 mg, 0.32 mmol, 1.2 equivalent). MS: calculated for C28H33ClN6O3S+H$^+$ 569.20, found 569.28.

Preparation of Compound VI(c)

Following the above general procedure, crude compound V(c) (0.27 mmol) in CH$_3$CN/H$_2$O (1/1, 2 mL) was allowed to undergo reaction with compound I (131.42 mg, 0.32 mmol, 1.2 equivalents). MS: calculated for C26H35ClN6O3+H$^+$ 515.24, found 515.31.

General Procedure for the Preparation of Compound VII

To crude compound VI (0.13 mmol, 1 equivalent) in CH$_3$CN/H$_2$O (1/1, 1 mL) was added amine (1.3 mmol, 10 equivalents). The reaction mixture was heated at 80° C. for 4-6 hours. The reaction was monitored with LC-MS. Crude compound VII was used directly in the next step.

Preparation of Compound VII(a)

Following the above general procedure, crude compound VI(a) (0.13 mmol) in CH$_3$CN/H$_2$O (1/1, 2 mL) was allowed to undergo reaction with phenethylamine (170 μl, 1.3 mmol, 10 equivalents). MS: calculated for C36H43N7O3+H$^+$ 622.34, found 622.47.

Preparation of Compound VII(b)

Following the above general procedure, crude compound VI(a) (0.13 mmol) in CH$_3$CN/H$_2$O (1/1, 2 mL) was allowed to undergo reaction with 2-thiopheneethylamine (10 equivalents). MS: calculated for C34H41N7O3S+H$^+$628.30, found 628.43.

Preparation of Compound VII(c)

Following the above general procedure, crude compound VI(b) (0.13 mmol) in CH$_3$CN/H$_2$O (1/1, 2 mL) was allowed to undergo reaction with pheneethylamine (170 μl, 1.3 mmol, 10 equivalents). MS: calculated for C36H43N7O3S+H$^+$ 654.31, found 654.43.

Preparation of Compound VII(d)

Following the above general procedure, crude compound VI(b) (0.13 mmol) in CH$_3$CN/H$_2$O (1/1, 2 mL) was allowed to undergo reaction with 2-thiopheneethylamine (10 equivalents). MS: calculated for C34H41N7O3S2+H$^+$660.27, found 660.38.

Preparation of Compound VII(e)

Following the above general procedure, crude compound VI(a) (0.1625 mmol) in CH$_3$CN/H$_2$O (1/1, 4 mL) was allowed to undergo reaction with methylamine (3.25 mmol, 20 equivalent). MS: calculated for C29H37N7O3+H$^+$532.30, found 532.36.

Preparation of Compound VII(f)

Following the above general procedure, crude compound VI(a) (0.1625 mmol) in CH$_3$CN/H$_2$O (1/1, 4 mL) was allowed to undergo reaction with isobutylamine (1.625 mmol, 10 equivalent). MS: calculated for C32H43N7O3+H$^+$ 574.34, found 574.42.

Preparation of Compound VII(g)

Following the above general procedure, crude compound VI(b) (0.1625 mmol) in CH$_3$CN/H$_2$O (1/1, 4 mL) was allowed to undergo reaction with methylamine (3.25 mmol, 20 equivalent). MS: calculated for C29H37N7O3S+H$^+$ 564.27, found 564.34.

Preparation of Compounds VII(h) and VIII (h)

Following the above general procedure, crude compound VI(b) (0.1625 mmol) in CH$_3$CN/H$_2$O (1/1, 4 mL) was allowed to undergo reaction with isobutylamine (1.625 mmol, 10 equivalents). The pH of the solution was approximately 11. After being heated at 80° C. for 2 hours, mostly demethylated product VIII(h) was produced, combined with a small amount of compound VII(h). Compound VIII(h) was purified by RP-HPLC (Luna 5μ, C8(2), 100×21 mm, 30-70% CH$_3$CN/H$_2$O, 0.1% TFA, 20 min). MS for compound VII(h): calculated for C32H43N7O3S+H$^+$606.31, found 606.39; MS for compound VIII(h): calculated for C31H41N7O3S+H$^+$ 592.30, found 592.37.

Preparation of Compound VII(i)

Following the above general procedure, crude compound VI(c) (9.4 mg, 0.018 mmol) in $CH_3CN$ (0.5 mL) was allowed to undergo reaction with phenethylamine (11 μl 0.09 mmol, 5 equivalents). MS: calculated for $C34H45N7O3+H^+$ 600.36, found 600.49.

General Procedure for the Preparation of Compound VIII

To crude compound VII (0.13 mmol, 1 equivalent) in $CH_3CN/H_2O$ (1/1, 1 mL) was added 1N NaOH (0.5-1 mL). The reaction mixture was stirred at room temperature for 3 hours to overnight. The reaction solution was neutralized with 1N HCl, which was further purified with RP-HPLC.

Preparation of Compound VIII(a)

Following the above general procedure, crude compound VII(a) (0.13 mmol) in $CH_3CN/H_2O$ (1/1, 2 mL) was allowed to undergo reaction with 1N NaOH (0.5 mL) at room temperature overnight. The product was purified with RP-HPLC (Luna 5μ, C8(2), 100×21 mm, 25-80% $CH_3CN/H_2O$, 0.1% TFA, 20 min). MS: calculated for $C35H41N7O3+H^+$ 608.33, found 608.40.

Preparation of Compound VIII(b)

Following the above general procedure, crude compound VII(b) (0.13 mmol) in $CH_3CN/H_2O$ (1/1, 2 mL) was allowed to undergo reaction with 1N NaOH (1.0 mL) at room temperature for 3 hours. The product was purified with RP-HPLC (Luna 5μ, C8(2), 100×21 mm, 25-80% $CH_3CN/H_2O$, 0.1% TFA, 20 min). MS: calculated for $C33H39N7O3S+H^+$ 614.28, found 614.36.

Preparation of Compound VIII(c)

Following the above general procedure, crude compound VII(c) (0.13 mmol) in $CH_3CN/H_2O$ (1/1, 2 mL) was allowed to undergo reaction with 1N NaOH (0.5 mL) at room temperature overnight. The product was purified with RP-HPLC (Luna 5μ, C8(2), 100×21 mm, 20-65% $CH_3CN/H_2O$, 0.1% TFA, 20 min). MS: calculated for $C35H41N7O3S+H^+$ 640.30, found 640.38.

Preparation of Compound VIII(d)

Following the above general procedure, crude compound VII(d) (0.13 mmol) in $CH_3CN/H_2O$ (1/1, 2 mL) was allowed to undergo reaction with 1N NaOH (0.5 mL) at room temperature for 3 hours. The product was purified with RP-HPLC (Luna 5μ, C8(2), 100×21 mm, 25-80% $CH_3CN/H_2O$, 0.1% TFA, 20 min). MS: calculated for $C33H39N7O3S2+H^+$ 646.26, found 646.30.

Preparation of Compound VIII(e)

Following the above general procedure, crude compound VII(e) (0.1625 mmol) in $CH_3CN/H_2O$ (1/1, 4 mL) was allowed to undergo reaction with 5N NaOH (0.5 mL) at room temperature for 14 hours. The product was purified with RP-HPLC (Luna 5μ C8(2), 100×21 mm, 25-65% $CH_3CN/H_2O$, 0.1% TFA, 20 min). MS: calculated for $C28H35N7O3+H^+$ 518.28, found 518.36.

Preparation of Compound VIII(f)

Following the above general procedure, crude compound VII(f) (0.1625 mmol) in $CH_3CN/H_2O$ (1/1, 4 mL) was allowed to undergo reaction with 5N NaOH (0.5 mL) at room temperature for 14 hours. The product was purified with RP-HPLC (Luna 5μ C8(2), 100×21 mm, 30-85% $CH_3CN/H_2O$, 0.1% TFA, 20 min). MS: calculated for $C31H41N7O3+H^+$ 560.33, found 560.41.

Preparation of Compound VIII(g)

Following the above general procedure, crude compound VII(g) (0.1625 mmol) in $CH_3CN/H_2O$ (1/1, 4 mL) was allowed to undergo reaction with 5N NaOH (0.5 mL) at room temperature for 14 hours. The product was purified with RP-HPLC (Luna 5μ C8(2), 100×21 mm, 25-70% $CH_3CN/H_2O$, 0.1% TFA, 20 min). MS: calculated for $C28H35N7O3S+H^+$ 550.25, found 550.31.

Preparation of Compound VIII(i)

Following the above general procedure, crude compound VII(i) (0.018 mmol) in $CH_3CN$ (0.5 mL) was allowed to undergo reaction with 1N NaOH (0.2 mL) at room temperature for overnight. The product was purified with RP-HPLC (Luna 5μ C8(2), 100×21 mm, 25-70% $CH_3CN/H_2O$, 0.1% TFA, 17 min). MS: calculated for $C33H43N7O3+H^+$ 586.34, found 586.43.

Scheme 3

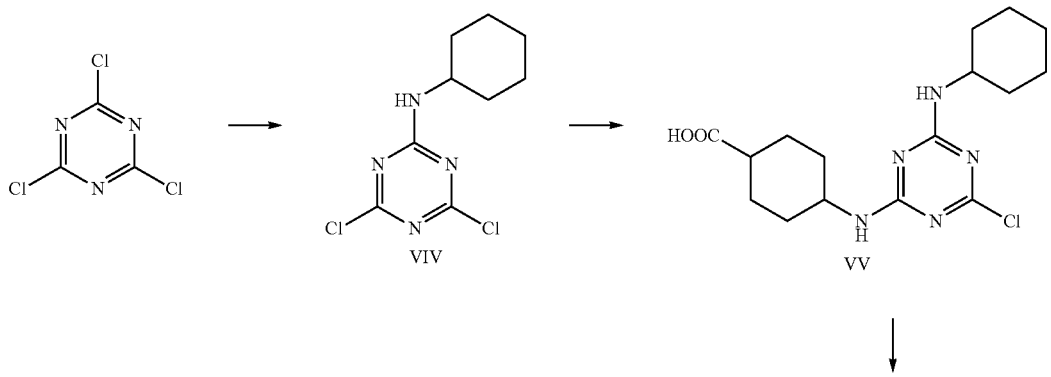

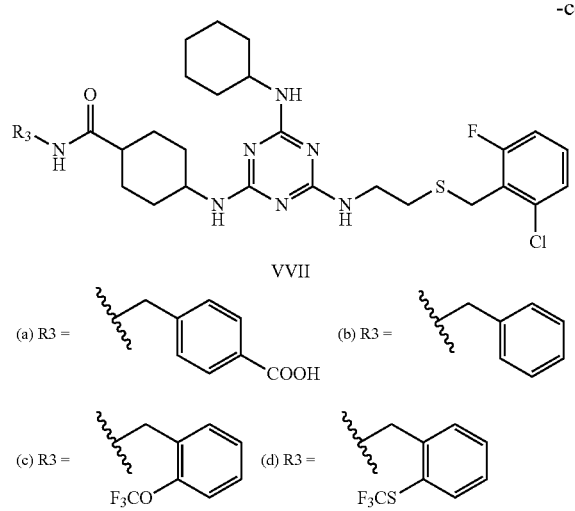

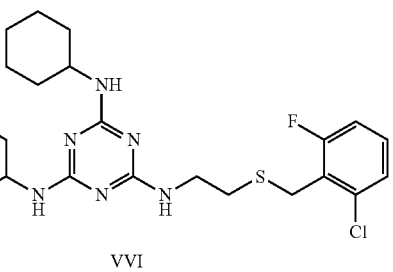

Preparation of Compound VIV

Following the general procedure for the preparation of compound V, cyanuric chloride (100 mg, 0.54 mmol) was allowed to undergo reaction with cyclohexylamine (62 μl, 0.54 mmol, 1 equivalent). LC-MS showed the starting material had been converted to desired product VIV. The crude product was used without purification in the next reaction.

Preparation of Compound VV

Following the general procedure for the preparation of compound VI, crude compound VIV (0.54 mmol) was allowed to undergo reaction with 4-aminocyclohexanecarboxylic acid (77.2 mg, 0.54 mmol, 1 equivalent). The reaction was stirred overnight at room temperature. The crude product was used without further purification. MS: calculated for $C_{16}H_{24}ClN_5O_2+H^+$ 354.16, found 354.24.

Preparation of Compound VVI

Following the general procedure for the preparation of compound VII, crude compound W (0.54 mmol) was allowed to undergo reaction with 2-(2-chloro-6-fluorobenzylthio) ethylamine (236.5 mg, 1.08 mmol, 2 equivalents). The reaction was completed after being stirred at 80° C. overnight. The solvent was evaporated and the crude compound VVI was purified by RP-HPLC (Luna 5μ C8(2), 100×21 mm, 30-77% CH$_3$CN/H$_2$O, 0.1% TFA, 17 min) to give the desired product (138.5 mg, 47.8% in 3 steps). MS: calculated for $C_{25}H_{34}ClFN_6O_2S+H^+$ 537.21, found 537.34.

General Procedure for the Preparation of Compound VVII

A solution of compound VVI (0.026 mmol, 1 equivalent), amine (0.0326 mmol, 1.25 equivalents) and DMAP (0.2 equivalent) in dichloromethane (1 mL) was cooled with stirring in an ice bath. 1-Ethyl-3-[3-(dimethylamino)propyl]carbodiimide hydrochloride (EDCl, 0.039 mmol, 1.5 equivalents) was added. The reaction mixture was stirred at 0° C. for 30 minutes and at room temperature for 2 hours. The solution was diluted with dichloromethane (1 mL), which was further washed with saturated sodium bicarbonate and water. The solvent was removed in vacuo to give the crude compound VVII which was further purified by RP-HPLC.

Preparation of Compound VVII (a)

Following the general procedure for the preparation of compound VVII, compound VVI (14 mg, 0.026 mmol, 1 equivalent) was treated with methyl 4-(aminomethyl)benzoate hydrochloride (6.6 mg, 0.0326 mmol, 1.25 equivalents), diisopropylethylamine (DIEA, 6.8 μl, 0.039 mmol, 1.5 equivalents), DMAP (0.6 mg, 0.0052 mmol, 0.2 equivalents) and EDCl (7.5 mg, 0.039 mmol, 1.5 equivalents). After workup, the solvent was removed in vacuo and the crude product was redissolved in MeOH (600 μl). 1N NaOH (700 μl) was added and the reaction mixture was stirred at room temperature for about 2 hours, followed by heating at 60° C. for 30 min. After neutralization of the reaction solution by addition of 1N HCl, the crude product was purified with RP-HPLC (Luna 5μ C8(2), 100×21 mm, 25-75% CH$_3$CN/H$_2$O, 0.1% TFA, 17 min) to produce the desired product (1.6 mg) and recovered methyl ester (10.5 mg). MS: calculated for $C_{33}H_{41}ClFN_7O_3S+H^+$ 670.27, found 670.4.

Preparation of Compound VVII (b)

Following the general procedure for the preparation of compound VVII, compound VVI (13.3 mg, 0.0247 mmol, 1 equivalent) was treated with benzylamine (3.4 μl, 0.031 mmol, 1.25 equivalents), DMAP (0.6 mg, 0.005 mmol, 0.2 equivalents) and EDCl (7.1 mg, 0.037 mmol, 1.5 equivalents) at room temperature for 2 hours. The crude product was purified with RP-HPLC (Luna 5μ, C8(2), 100×21 mm, 30-78% CH$_3$CN/H$_2$O, 0.1% TFA, 17 min) to give compound VVII(b) (6.4 mg, 41%). MS: calculated for $C_{32}H_{41}ClFN_7O_3S+H^+$ 626.28, found 626.40.

Preparation of Compound VVII (c)

Following the general procedure for the preparation of compound VVII, compound VVI (11.38 mg, 0.0212 mmol, 1 equivalent) was treated with 2-(trifluoromethyl)-benzenemethanamine (5.1 mg, 0.0265 mmol, 1.25 equivalents), DMAP (0.5 mg, 0.2 equivalents) and EDCl (6.1 mg, 0.032 mmol, 1.5 equivalents) at room temperature for 2 hrs. The crude product was purified with RP-HPLC (Luna 5μ, C8(2), 100×21 mm, 30-78%

CH₃CN/H₂O, 0.1% TFA, 17 min) to give compound VVII (c) (9.2 mg, 61%). MS: calculated for C33H40ClF4N7OS+ H⁺710.26, found 710.38.

Preparation of Compound VVII (d)

Following the general procedure for the preparation of compound VVII, compound VVI (10.78 mg, 0.02 mmol, 1 equivalent) was treated with 2-(trifluoromethyl)thio-benzenemethanamine as the TFA salt (8.2 mg, 0.033 mmol, 1.6 equivalents), DIEA (5.6 µl, 1.6 eqiv), DMAP (0.5 mg, 0.2 equivalents) and EDCl (5.8 mg, 0.03 mmol, 1.5 equivalents) at room temperature for 2 hrs. The crude product was purified with RP-HPLC (Luna 5µ, C8(2), 100×21 mm, 30-78% CH₃CN/H₂O, 0.1% TFA, 17 min) to give compound VVII(d) (12.8 mg, 88%). MS: calculated for C33H40ClF4N7OS2+H⁺ 726.24, found 726.36.

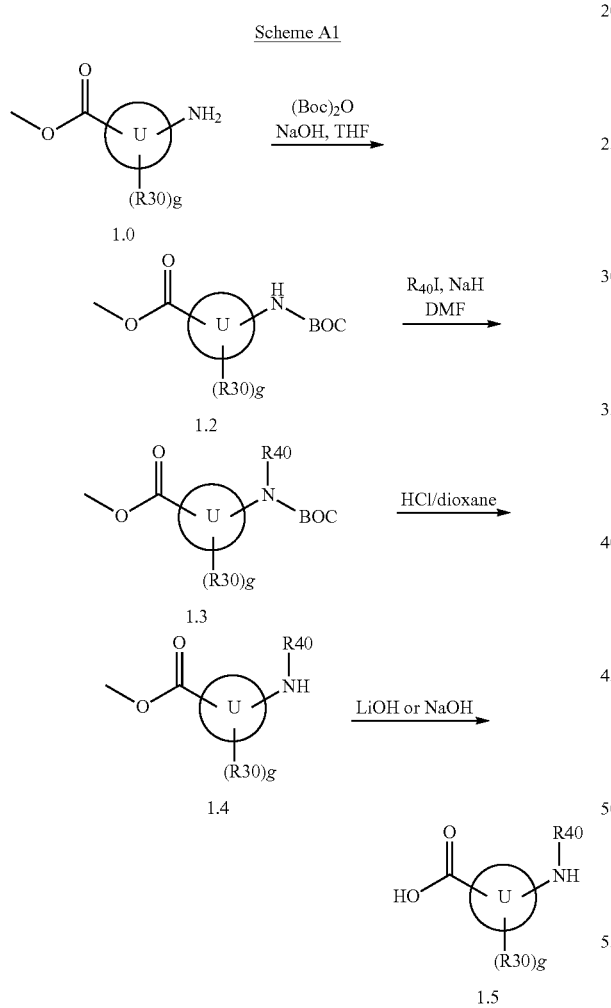

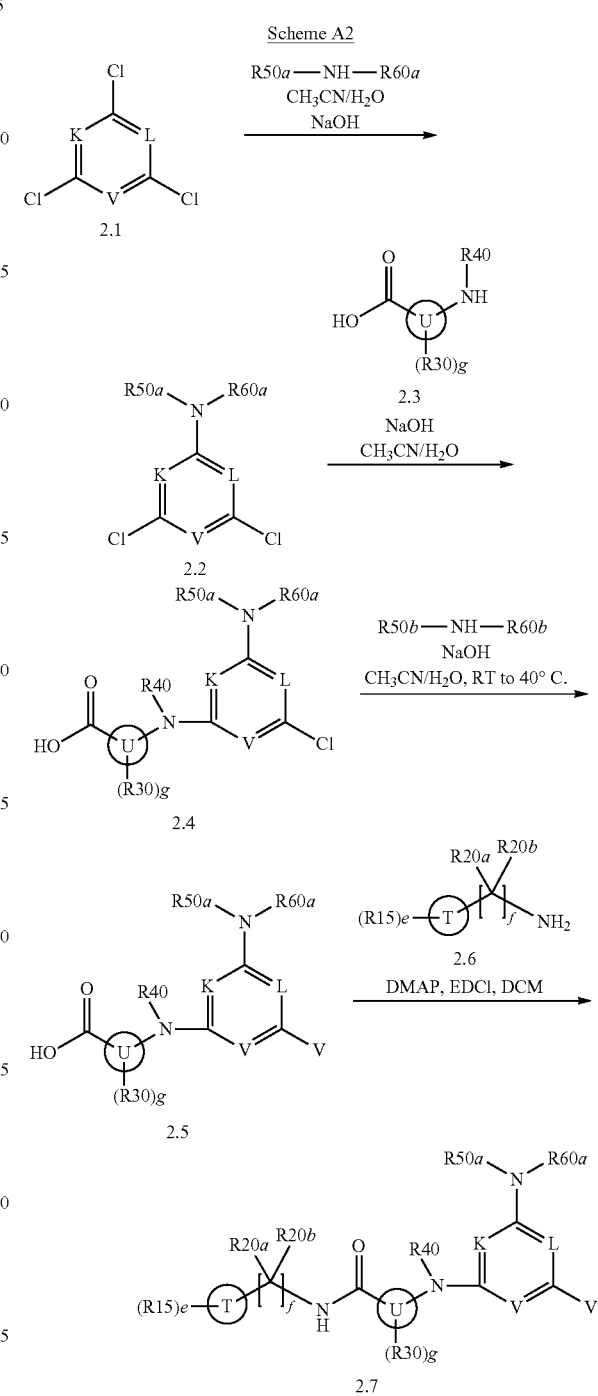

provides amine 1.4. Hydrolysis of methyl ester 1.4 with either lithium hydroxide or sodium hydroxide provides amino-acid 1.5.

Treatment of amine 1.0 (commercially available or made from commercially available starting materials using methods known to those skilled in the art) with BOC anhydride gave the corresponding carbamate 1.2. Alkylation of 1.2 with an alkyl iodide or cycloalkyl iodide (commercially available or made from commercially available starting materials using methods known to those skilled in the art) provides intermediate 1.3. Deprotection of BOC-intermediate 1.3 with HCl Treatment of 2,4,6-trichlorotriazine 2.1 (commercially available) with amine HNR50aR06a (commercially available or made from commercially available starting materials using methods known to those skilled in the art) affords aminotriazine 2.2. Reaction of chloro-triazine 2.2 with amino-carboxylic acid 2.3 (commercially available or made from commercially available starting materials using methods known to those skilled in the art) provides triazine 2.4. Treatment of chloro-triazine 2.4 with amine HNR50bR06b (commercially available or made from commercially available starting materials using methods known to those skilled in the art) provides triamino-triazine 2.5. Treatment of carboxylic acid intermediate 2.5 with amine 2.6 (commercially available or made from commercially available starting materials using methods known to those skilled in the art) and a coupling reagent (such as EDCl or BOP reagent) and a base (such as triethylamine) provides amide 2.7.

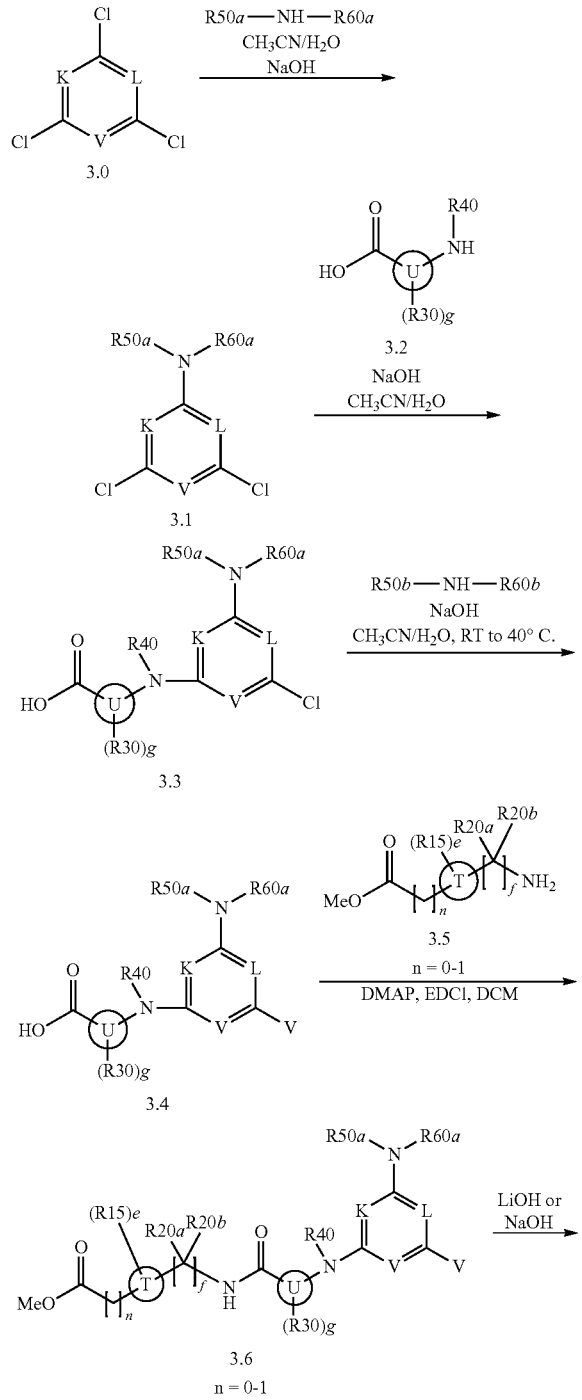

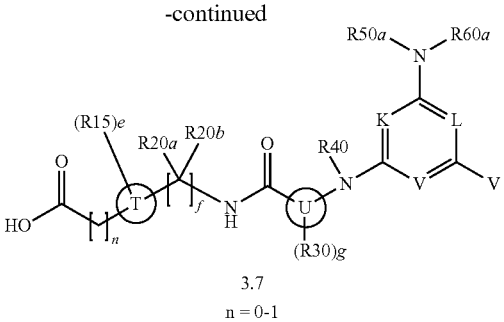

Treatment of 2,4,6-trichlorotriazine 3.0 (commercially available) with amine HNR50aR06a (commercially available or made from commercially available starting materials using methods known to those skilled in the art) affords amino-triazine 3.1. Reaction of chloro-triazine 3.1 with amino-carboxylic acid 3.2 (commercially available or made from commercially available starting materials using methods known to those skilled in the art) provides triazine 3.3. Treatment of chloro-triazine 3.3 with amine HNR50bR06b (commercially available or made from commercially available starting materials using methods known to those skilled in the art) provides triamino-triazine 3.4. Treatment of carboxylic acid intermediate 3.4 with amine 3.5 (commercially available or made from commercially available starting materials using methods known to those skilled in the art) and a coupling reagent (such as EDCl or BOP reagent) and a base (such as triethylamine) provides amide 3.6. Hydrolysis of methyl carboxylate 3.6 using either lithium hydroxide or sodium hydroxide provides target 3.7.

Compound 13 cis-N-[(2,4-dichlorophenyl)methyl]-4-{[4-(methylamino)-6-(4-methyl-1-piperazinyl)-1,3,5-triazin-2-yl]amino}cyclohexanecarboxamide

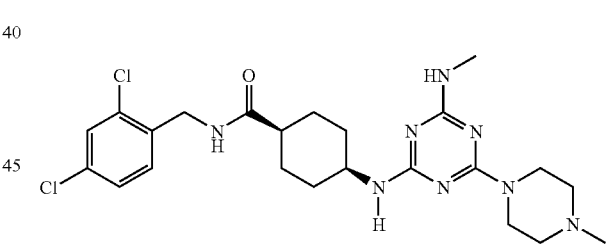

a) Preparation of 4,6-dichloro-N-methyl-1,3,5-triazin-2-amine

A mixture of 2,4,6-trichloro-1,3,5-triazine (4.27 g, 17.46 mmol) in a solution of $CH_3CN:H_2O$ (1:1, 28.6 mL) was cooled to 0° C. A solution of 30% $NH_2Me$ in $H_2O$ (17.46 mmol) was added. The reaction mixture was adjusted to pH of about 9-10 using 1N NaOH. The pH was maintained at about 9-10 for 15 minutes. LCMS analysis showed the complete consumption of the 2,4,6-trichloro-1,3,5-triazine. The crude product was used in the next step. MS (ES+): m/e 178.9 $[M+H]^+$.

b) Preparation of cis-4-{[4-chloro-6-(methylamino)-1,3,5-triazin-2-yl]amino}cyclohexanecarboxylic acid Commercially available cis-4-aminocyclohexanecarboxylic acid (17.46 mmol) was added to the above crude solution of 4,6-dichloro-N-methyl-1,3,5-triazin-2-amine in CH₃CN:H₂O (1:1, 28.6 mL). The reaction mixture was stirred at room temperature to 40° C. for 3 hours while the pH was maintained between 9 and 10 with addition of a NaOH solution. LCMS analysis showed the complete consumption of 4,6-dichloro-N-methyl-1,3,5-triazin-2-amine. The crude product was used in the next step. MS (ES+): m/e 286.0 [M+H]⁺.

c) Preparation of 4-{[4-(methylamino)-6-(4-methyl-1-piperazinyl)-1,3,5-triazin-2-yl]lamino}cyclohexanecarboxylic acid Commercially available 1-methylpiperazine (17.46 g, 174.6 mmol) was added to a mixture of crude cis-4-{[4-chloro-6-(methylamino)-1,3,5-triazin-2-yl]amino}cyclohexanecarboxylic acid (17.46 mmol) in a solution of CH₃CN:H₂O (1:1, 28.6 mL). The reaction mixture was heated to 80° C. overnight. LCMS analysis showed the complete consumption of the cis-4-{[4-chloro-6-(methylamino)-1,3,5-triazin-2-yl]amino}cyclohexanecarboxylic acid. The solvent was removed and the residue was dissolved in DMSO/MeOH and purified by HPLC to afford 6 g (92%) of the desired product. MS (ES+): m/e 350.1 [M+H]⁺.

d) Preparation of cis-N-[(2,4-dichlorophenyl)methyl]-4-{[4-(methylamino)-6-(4-methyl-1-piperazinyl)-1,3,5-triazin-2-yl]amino}cyclohexanecarboxamide A solution of 4-{[4-(methylamino)-6-(4-methyl-1-piperazinyl)-1,3,5-triazin-2-yl]amino}cyclohexanecarboxylic acid (150 mg, 0.43 mmol), [(2,4-dichlorophenyl)methyl]amine (95 mg, 0.54 mmol) and DMAP (8 mg, 0.06 mmol) in DCM was stirred at room temperature. To this was added EDCl (90.8 mg, 0.47 mmol) and the resulting mixture was allowed to stir overnight. The solution was washed with water. The organic layer was dried and purified by HPLC to afford 78 mg (36% yield) of the product as a white solid. MS (ES+): m/e 507.1 [M+H]⁺.

Compound 14 cis-N-[(2-fluorophenyl)methyl]-4-{[4-(methylamino)-6-(4-methyl-1-piperazinyl)-1,3,5-triazin-2-yl]amino}cyclohexanecarboxamide hydrochloride

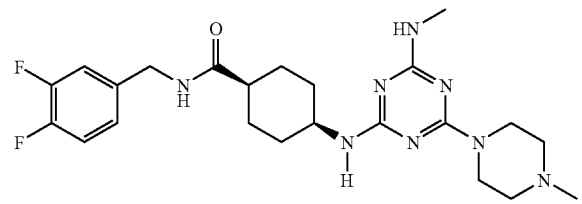

Compound 14 was prepared using the general procedure described above for Compound 13 substituting the appropriate starting materials. MS (ES+): m/e 457.2 [M+H]⁺.

Compound 15 cis-N-[(3,4-difluorophenyl)methyl]-4-{[4-(methylamino)-6-(4-methyl-1-piperazinyl)-1,3,5-triazin-2-yl]amino}cyclohexanecarboxamide hydrochloride

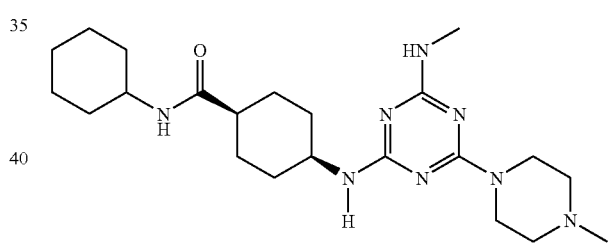

Compound 15 was prepared using the general procedure described above for Compound 13 substituting the appropriate starting materials. MS (ES+): m/e 475.2 [M+H]⁺.

Compound 16 cis-N-cyclohexyl-4-{[4-(methylamino)-6-(4-methyl-1-piperazinyl)-1,3,5-triazin-2-yl]amino}cyclohexanecarboxamide hydrochloride Compound 16 was prepared using the general procedure described above for Compound 13 substituting the appropriate starting materials. MS (ES+): m/e 431.2 [M+H]⁺.

Compound 17 cis-N-(cyclohexylmethyl)-4-{[4-(methylamino)-6-(4-methyl-1-piperazinyl)-1,3,5-triazin-2-yl]amino}cyclohexanecarboxamide hydrochloride

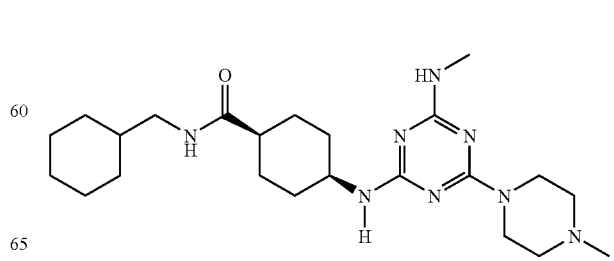

Compound 17 was prepared using the general procedure described above for Compound 13 substituting the appropriate starting materials. MS (ES+): m/e 445.2 [M+H]$^+$.

Compound 18 cis-4-{[4-(methylamino)-6-(4-methyl-1-piperazinyl)-1,3,5-triazin-2-yl]amino}-N-{[2-(trifluoromethyl)phenyl]methyl}cyclohexanecarboxamide hydrochloride

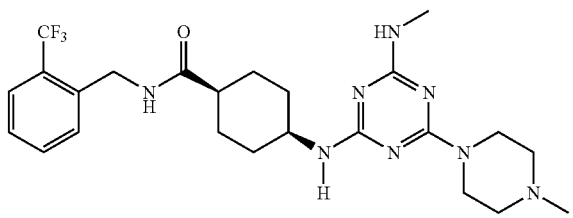

Compound 18 was prepared using the general procedure described above for Compound 13 substituting the appropriate starting materials. MS (ES+): m/e 507.2 [M+H]$^+$.

Compound 19 cis-N-[(2-chlorophenyl)methyl]-4-{[4-(methylamino)-6-(4-methyl-1-piperazinyl)-1,3,5-triazin-2-yl]amino}cyclohexanecarboxamide hydrochloride

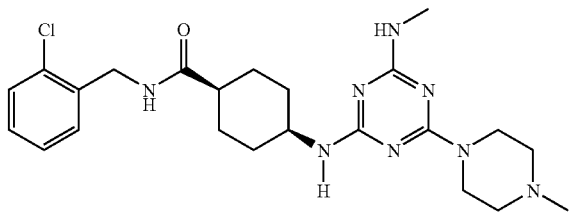

Compound 19 was prepared using the general procedure described above for Compound 13 substituting the appropriate starting materials. MS (ES+): m/e 473.1 [M+H]$^+$.

Compound 20 cis-4-{[4-(methylamino)-6-(4-methyl-1-piperazinyl)-1,3,5-triazin-2-yl]amino}-N-({2-[(trifluoromethyl)oxy]phenyl}methyl)cyclohexanecarboxamide hydrochloride

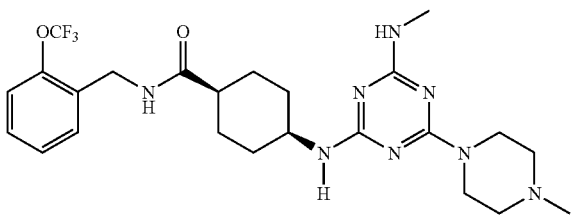

Compound 20 was prepared using the general procedure described above for Compound 13 substituting the appropriate starting materials. MS (ES+): m/e 523.2 [M+H]$^+$.

Compound 21 trans-4-{[4-(methylamino)-6-(4-methyl-1-piperazinyl)-1,3,5-triazin-2-yl]amino}-N-{[2-(trifluoromethyl)phenyl]methyl}cyclohexanecarboxamide trifluoroacetate

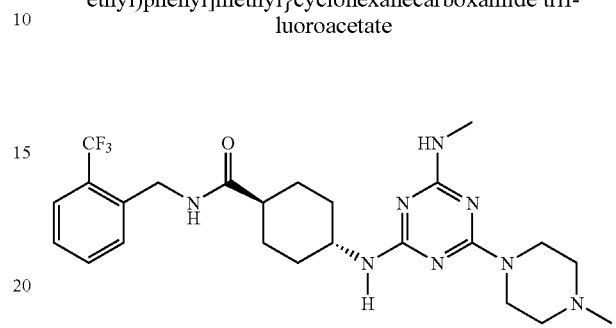

Compound 21 was prepared using the general procedure described above for Compound 13 substituting the appropriate starting materials. MS (ES+): m/e 507.1 [M+H]$^+$.

Compound 22 trans-4-{[4-(methylamino)-6-(4-methyl-1-piperazinyl)-1,3,5-triazin-2-yl]amino}-N-({2-[(trifluoromethyl)oxy]phenyl}methyl)cyclohexanecarboxamide trifluoroacetate

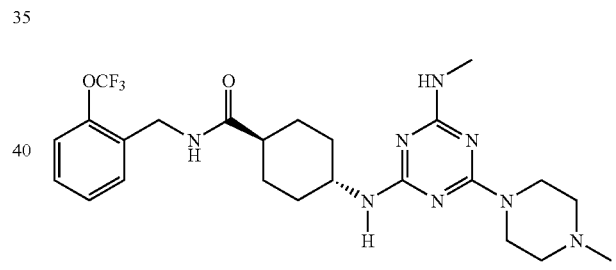

Compound 22 was prepared using the general procedure described above for Compound 13 substituting the appropriate starting materials. MS (ES+): m/e 523.2 [M+H]$^+$.

Compound 23 trans-N-[(2,4-dichlorophenyl)methyl]-4-{[4-(methylamino)-6-(4-methyl-1-piperazinyl)-1,3,5-triazin-2-yl]amino}cyclohexanecarboxamide trifluoroacetate

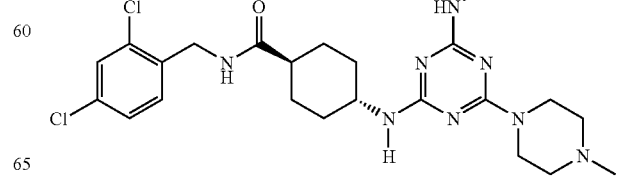

Compound 23 was prepared using the general procedure described above for Compound 13 substituting the appropriate starting materials. MS (ES+): m/e 507.1 [M+H]$^+$.

Compound 24

N-[(3,4-difluorophenyl)methyl]-3-{[4-(methylamino)-6-(4-methyl-1-piperazinyl)-1,3,5-triazin-2-yl]amino}cyclohexanecarboxamide hydrochloride

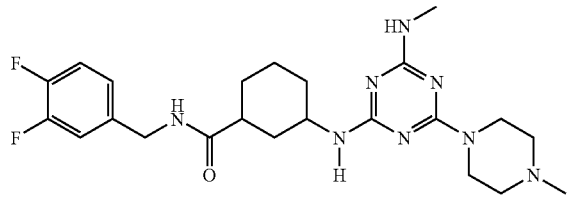

Compound 24 was prepared using the general procedure described above for Compound 13 substituting the appropriate starting materials. MS (ES+): m/e 475.1 [M+H]$^+$.

Compound 25

N-(cyclohexylmethyl)-3-{[4-(methylamino)-6-(4-methyl-1-piperazinyl)-1,3,5-triazin-2-yl]amino}cyclohexanecarboxamide hydrochloride

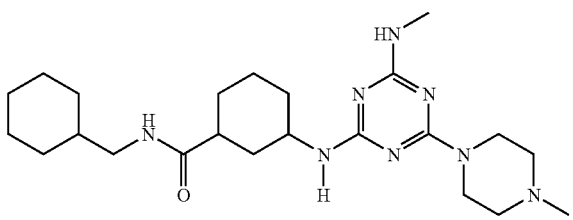

Compound 25 was prepared using the general procedure described above for Compound 13 substituting the appropriate starting materials. MS (ES+): m/e 445.2 [M+H]$^+$.

Compound 26

3-{[4-(methylamino)-6-(4-methyl-1-piperazinyl)-1,3,5-triazin-2-yl]amino}-N-{[2-(trifluoromethyl)phenyl]methyl}cyclohexanecarboxamide hydrochloride

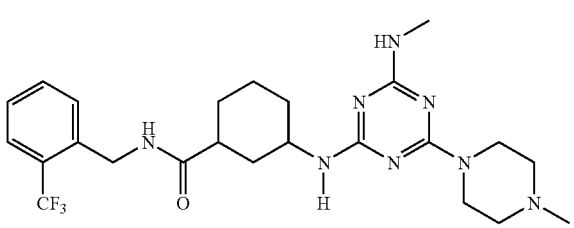

Compound 26 was prepared using the general procedure described above for Compound 13 substituting the appropriate starting materials. MS (ES+): m/e 507.1 [M+H]$^+$.

Compound 27

N-[(2-chlorophenyl)methyl]-3-{[4-(methylamino)-6-(4-methyl-1-piperazinyl)-1,3,5-triazin-2-yl]amino}cyclohexanecarboxamide hydrochloride

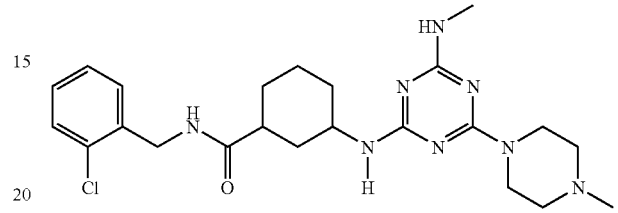

Compound 27 was prepared using the general procedure described above for Compound 13 substituting the appropriate starting materials. MS (ES+): m/e 473.1 [M+H]$^+$.

Compound 28

N-[(2-fluorophenyl)methyl]-3-{[4-(methylamino)-6-(4-methyl-1-piperazinyl)-1,3,5-triazin-2-yl]amino}cyclohexanecarboxamide hydrochloride

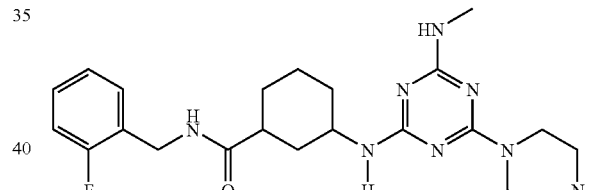

Compound 28 was prepared using the general procedure described above for Compound 13 substituting the appropriate starting materials. MS (ES+): m/e 457.1 [M+H]$^+$.

Compound 29

3-{[4-(methylamino)-6-(4-methyl-1-piperazinyl)-1,3,5-triazin-2-yl]amino}-N-({2-[(trifluoromethyl)oxy]phenyl}methyl)cyclohexanecarboxamide hydrochloride

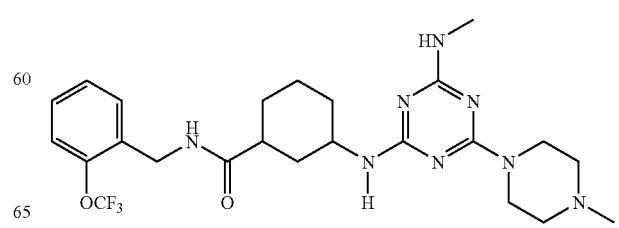

Compound 29 was prepared using the general procedure described above for Compound 13 substituting the appropriate starting materials. MS (ES+): m/e 523.3 [M+H]+.

Compound 30

N-[(2,4-dichlorophenyl)methyl]-3-{[4-(methylamino)-6-(4-methyl-1-piperazinyl)-1,3,5-triazin-2-yl]amino}cyclohexanecarboxamide trifluoroacetate

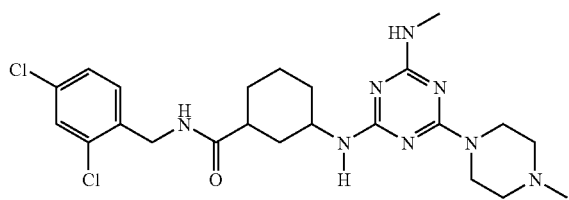

Compound 30 was prepared using the general procedure described above for Compound 13 substituting the appropriate starting materials. MS (ES+): m/e 507.2 [M+H]+.

Compound 31 cis-N-[(2,4-dichlorophenyl)methyl]-4-{methyl[4-(methylamino)-6-(4-methyl-1-piperazinyl)-1,3,5-triazin-2-yl]amino}cyclohexanecarboxamide

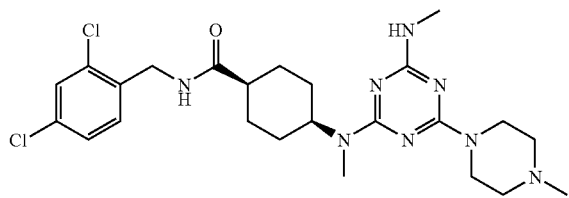

a) Preparation of methyl cis-4-({[(1,1-dimethylethyl)oxy]carbonyl}amino) cyclohexanecarboxylate An aqueous solution of sodium hydroxide (5.6 g, 0.14 mol) and 1,4-dioxane was added to methyl cis-4-aminocyclohexanecarboxylate (5 g, 0.035 mol) followed by addition of Boc-anhydride (15.3 g, 0.07 mol) at 0° C. The resulting mixture was allowed to stir overnight at room temperature. The reaction mixture was washed with water and the pH was adjusted to 4-5 with 1M HCl. The organic layer was washed with additional water and concentrated to afford 9.3 g of crude product as a white solid. MS (ES+): m/e 158.2 [M+H-boc]+.

b) Preparation of methyl cis-4-[{[(1,1-dimethylethyl)oxy]carbonyl}(methyl)amino]cyclohexanecarboxylate A solution of methyl cis-4-({[(1,1-dimethylethyl)oxy]carbonyl}amino) cyclohexanecarboxylate (9 g, crude) in N,N-dimethylacetamide (50 mL) was cooled to 0° C. and treated with 60% NaH (2.45 g, 0.062 mol) over 30 min. The mixture was warmed to room temperature for 1 hour then cooled to 0° C. again and treated with iodomethane (30 g, 0.144 mol). The resulting mixture was allowed to warm to room temperature and stir overnight. The reaction mixture was then cooled to 0° C. and poured into an ice cold solution of ammonium chloride. The mixture was then acidified with 1M sodium sulfate and concentrated to give the 10 g of crude product as an oil which contained N,N-dimethylacetamide. MS (ES+): m/e 172.1 [M+H-boc]+.

c) Preparation of methyl cis-4-(methylamino)cyclohexanecarboxylate

A mixture of methyl cis-4-[{[(1,1-dimethylethyl)oxy]carbonyl}(methyl)amino]cyclohexanecarboxylate (~10 g, crude product from above) and 1M HCl in dioxane (20 mL) was heated to 50° C. and allowed to stir overnight. The mixture was concentrated to give the 3 g of crude product. MS (ES+): m/e 172.1 [M+H]+.

d) Preparation of cis-4-(methylamino)cyclohexanecarboxylic acid

The methyl cis-4-(methylamino)cyclohexanecarboxylate (3 g, 0.0175 mol) from above was dissolved in a THF/H2O (10 mL) mixture and was cooled to 0° C. Next 2 L of a 0.025 M solution of NaOH was added slowly. The mixture was stirred a 0° C. for another 0.5 hour. The mixture was then acidified to pH 7-8 and extracted with ethyl acetate. The water layer was acidified to pH 3-4 and extracted with ethyl acetate. The organic layer was dried over Na2SO4 and concentrated to give 2.49 g (0.016 mol, 90% yield) of product.

e) Preparation of cis-4-{methyl[4-(methylamino)-6-(4-methyl-1-piperazinyl)-1,3,5-triazin-2-yl]amino}cyclohexanecarboxylic acid A mixture of 2,4,6-trichloro-1,3,5-triazine (0.5 g, 2.0 mmol) in a solution of CH3CN:H2O (1:1, 20 mL) was cooled to 0° C. A 2 M solution of methylamine in THF (1 mL, 2.0 mmol) was added. The reaction mixture was adjusted to a pH of about 8-9 using 1 N NaOH. The pH was maintained at about 9-10 for 0.5 hour. LCMS analysis showed the complete consumption of the 2,4,6-trichloro-1,3,5-triazine. To this mixture was added cis-4-(methylamino)cyclohexanecarboxylic acid (0.32 g, 2.0 mmol). The reaction mixture was stirred at room temperature while the pH was maintained between 8 and 9. Next, 1-methylpiperazine (2 g, 20 mmol) was added and the mixture was heated to 50° C. overnight. The solvent was removed and the crude product was purified by HPLC to afford 0.32 g (0.09 mmol, 44% yield) of the desired product. MS (ES+): m/e 364.2 [M+H]+.

f) Preparation of cis-N-[(2,4-dichlorophenyl)methyl]-4-{methyl[4-(methylamino)-6-(4-methyl-1-piperazinyl)-1,3,5-triazin-2-yl]amino}cyclohexanecarboxamide A solution of cis-4-{methyl[4-(methylamino)-6-(4-methyl-1-piperazinyl)-1,3,5-triazin-2-yl]amino}cyclohexanecarboxylic acid (50 mg, 0.138 mmol), [(2,4-dichlorophenyl)methyl]amine (30 mg, 0.17 mmol), and DMAP (3.37 mg, 0.028 mmol) in DMF/DCM was cooled in an ice bath. EDCl (40 mg, 0.21 mmol) was added. The reaction mixture was stirred at 0° C. for 0.5 hour, and then at room temperature for 2 hours. The solution was diluted with DCM and then washed with a saturated NaCl solution. The organic layer was dried over NaSO4 and concentrated to give the crude product which was purified by HPLC. After purification, 29 mg (0.06 mmol, 40% yield) of product was obtained as a white solid. MS (ES+): m/e 521.1 [M+H]+.

Compound 32 cis-4-{methyl[4-(methylamino)-6-(4-methyl-1-piperazinyl)-1,3,5-triazin-2-yl]amino}-N-{[2-(trifluoromethyl)phenyl]methyl}cyclohexanecarboxamide trifluoroacetate

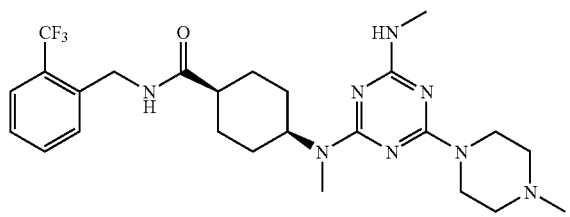

Compound 32 was prepared using the general procedure described above for Compound 31 substituting the appropriate starting materials. MS (ES+): m/e 521.3 [M+H]+.

Compound 33 cis-4-{methyl[4-(methylamino)-6-(4-methyl-1-piperazinyl)-1,3,5-triazin-2-yl]amino}-N-({2-[(trifluoromethyl)oxy]phenyl}methyl)cyclohexanecarboxamide trifluoroacetate

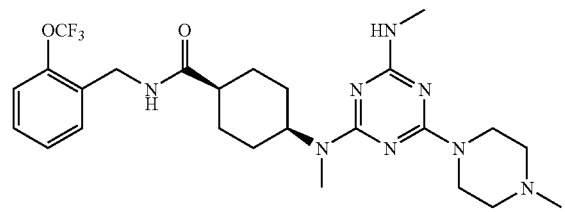

Compound 33 was prepared using the general procedure described above for Compound 31 substituting the appropriate starting materials. MS (ES+): m/e 537.3 [M+H]+.

Compound 34

(1S,4S)-4-(4-(methylamino)-6-((R)-2-phenylpropylamino)-1,3,5-triazin-2-ylamino)-N-(2-(trifluoromethyl)benzyl)cyclohexanecarboxamide

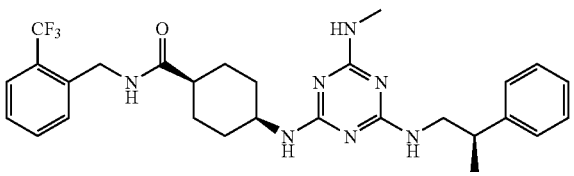

a) Preparation of (R)-4,6-dichloro-N-(2-phenylpropyl)-1,3,5-triazin-2-amine

A mixture of cyanuric chloride (75 mg, 0.407 mmol, 1 equivalent) in CH$_3$CN/H$_2$O (1/1, 5 ml) was cooled to 0° C. (R)-(+)-beta-methylphenethylamine (55 mg, 0.407 mmol, 1 equivalent) was added, followed by 1N NaOH (0.366 ml). LCMS analysis showed the complete consumption of the 2,4,6-trichloro-1,3,5-triazine. The crude product was used in the next step. MS (ES+): m/e 283.06 [M+H]+.

b) Preparation of (1S,4S)-4-(4-chloro-6-((R)-2-phenylpropylamino)-1,3,5-triazin-2-ylamino)cyclohexanecarboxylic acid To the above reaction solution of (R)-4,6-dichloro-N-(2-phenylpropyl)-1,3,5-triazin-2-amine (0.2035 mmol) in CH$_3$CN/H$_2$O (1/1, 2.5 ml) was added cis-4-amino-cyclohexanecarboxylic acid (27.5 mg, 0.2035 mmol, 1 equivalent). 1N NaOH was added to the reaction to adjust the pH to about 9-10. The reaction mixture was stirred at room temperature overnight. To the reaction was added additional cis-4-amino-cyclohexanecarboxylic acid (7.0 mg, 0.049 mmol, 0.25 equivalents). 1N NaOH was added to the reaction to adjust the pH to about 9-10. The reaction mixture was stirred at room temperature for 1 hour. The crude product was used in the next step. MS (ES+): m/e 390.21 [M+H]+.

c) Preparation of (1S,4s)-4-(4-(methylamino)-6-((R)-2-phenylpropylamino)-1,3,5-triazin-2-ylamino)cyclohexanecarboxylic acid To the above reaction solution of (1S,4S)-4-(4-chloro-6-((R)-2-phenylpropylamino)-1,3,5-triazin-2-ylamino)cyclohexanecarboxylic acid (0.2 mmol) in CH$_3$CN/H$_2$O (1/1, 2.5 ml) was added methylamine (40% aq. (w), 0.158 ml, 2.305 mmol, 10 equivalents). The reaction mixture was heated at 80° C. for 3 hours. The reaction solution was acidified and condensed to give the crude which was further purified by RP-HPLC (Luna 5μ; C8(2), 100×21 mm, 30-80% CH$_3$CN/H$_2$O, 0.1% TFA, 20 min) to give the product (46.7 mg). MS (ES+): m/e 385.28 [M+H]+.

d) Preparation of (1S,4S)-4-(4-(methylamino)-6-((R)-2-phenylpropylamino)-1,3,5-triazin-2-ylamino)-N-(2-(trifluoromethylbenzyl)cyclohexanecarboxamide A solution of (1S,4S)-4-(4-(methylamino)-6-((R)-2-phenylpropylamino)-1,3,5-triazin-2-ylamino)cyclohexanecarboxylic acid (10.0 mg, 0.026 mmol, 1 equivalent), 2-trifluoromethyl benzylamine (23.0 mg, 0.130 mmol, 5.0 equivalents) and DMAP (0.6 mg, 0.2 equivalents) in dichloromethane (0.5 ml) was cooled with stirring in an ice bath. EDCl (6.2 mg, 0.0324 mmol, 1.25 equivalents) was added. The reaction mixture was stirred with gradual warming to room temperature for 16 hours. The solution was diluted with dichloromethane, which was further washed with saturated sodium bicarbonate and water. The solvent was removed to give the crude product which was further purified by reverse phase-HPLC (Luna 5μ; C8(2), 100×21 mm, 25-85% CH$_3$CN/

H₂O, 0.1% TFA, 20 min) to give the final product (11.1 mg, 78.8%). MS (ES+): m/e 542.3 [M+H]⁺.

Compound 35

(1S,4S)-4-(4-(methylamino)-6-((R)-2-phenylpropylamino)-1,3,5-triazin-2-ylamino)-N-(2-(trifluoromethylthio)benzyl)cyclohexanecarboxamide

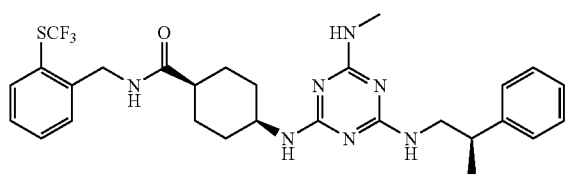

Compound 35 was prepared using the general procedure described above for Compound 34 substituting the appropriate starting materials. MS (ES+): m/e 574.3 [M+H]⁺.

Compound 36

(1S,4S)-4-(4-(methylamino)-6-((R)-2-phenylpropylamino)-1,3,5-triazin-2-ylamino)-N-(2-(trifluoromethoxy)benzyl)cyclohexanecarboxamide

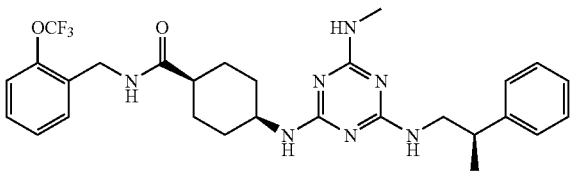

Compound 36 was prepared using the general procedure described above for Compound 34 substituting the appropriate starting materials. MS (ES+): m/e 558.3 [M+H]⁺.

Compound 37

(1S,4S)—N-benzyl-4-(4-(methylamino)-6-((R)-2-phenylpropylamino)-1,3,5-triazin-2-ylamino)cyclohexanecarboxamide

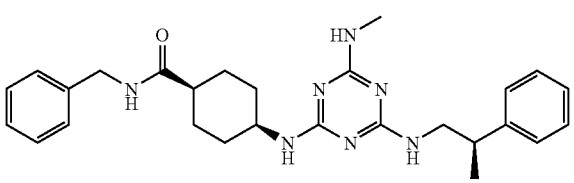

Compound 37 was prepared using the general procedure described above for Compound 34 substituting the appropriate starting materials. MS (ES+): m/e 474.3 [M+H]⁺.

Compound 38

(1S,4S)-4-(4-(methylamino)-6-((R)-2-phenylpropylamino)-1,3,5-triazin-2-ylamino)-N-(4-(trifluoromethyl)benzyl)cyclohexanecarboxamide

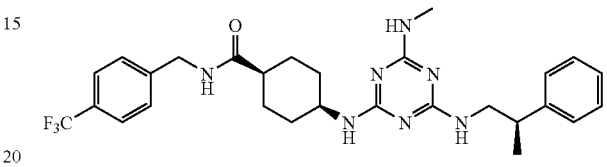

Compound 38 was prepared using the general procedure described above for Compound 34 substituting the appropriate starting materials. MS (ES+): m/e 542.2 [M+H]⁺.

Compound 39

(1S,4S)—N-(4-fluorobenzyl)-4-(4-(methylamino)-6-((R)-2-phenylpropylamino)-1,3,5-triazin-2-ylamino)cyclohexanecarboxamide

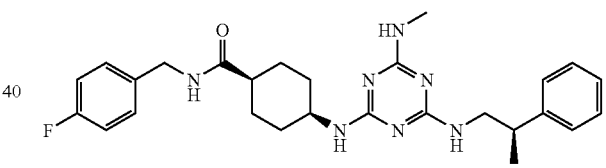

Compound 39 was prepared using the general procedure described above for Compound 34 substituting the appropriate starting materials. MS (ES+): m/e 492.2 [M+H]⁺.

Compound 40

(1S,4S)—N-(2-fluorobenzyl)-4-(4-(methylamino)-6-((R)-2-phenylpropylamino)-1,3,5-triazin-2-ylamino)cyclohexanecarboxamide

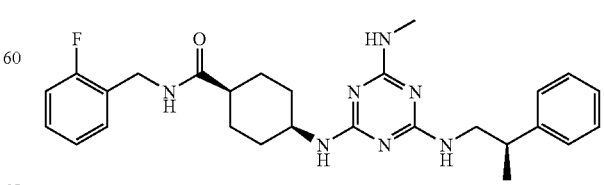

Compound 40 was prepared using the general procedure described above for Compound 34 substituting the appropriate starting materials. MS (ES+): m/e 492.2 [M+H]⁺.

Compound 41

(1S,4S)-4-(4-(methylamino)-6-((R)-2-phenylpropylamino)-1,3,5-triazin-2-ylamino)-N-o-tolylcyclohexanecarboxamide

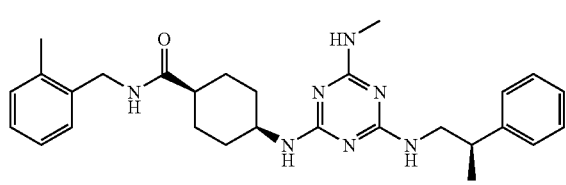

Compound 41 was prepared using the general procedure described above for Compound 34 substituting the appropriate starting materials. MS (ES+): m/e 474.2 [M+H]⁺.

Compound 42

(1R,4R)—N-benzyl-4-(4-(methylamino)-6-((R)-2-phenylpropylamino)-1,3,5-triazin-2-ylamino)cyclohexanecarboxamide

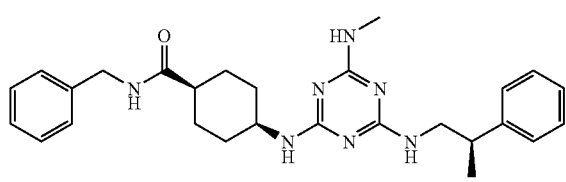

Compound 42 was prepared using the general procedure described above for Compound 34 substituting the appropriate starting materials. MS (ES+): m/e 474.2 [M+H]⁺.

Compound 43 methyl 4-(((1S,4S)-4-(4-(methylamino)-6-((R)-2-phenylpropylamino)-1,3,5-triazin-2-ylamino)cyclohexanecarboxamido)methyl)benzoate

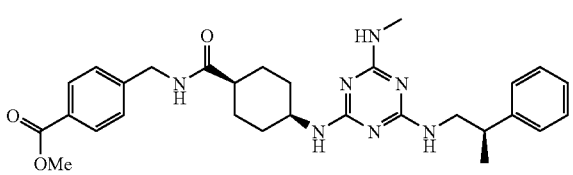

Compound 43 was prepared using the general procedure described above for Compound 34 substituting the appropriate starting materials. MS (ES+): m/e 532.3 [M+H]⁺.

Compound 44 methyl 4-(((1R,4R)-4-(4-(methylamino)-6-((R)-2-phenylpropylamino)-1,3,5-triazin-2-ylamino)cyclohexanecarboxamido)methyl)benzoate

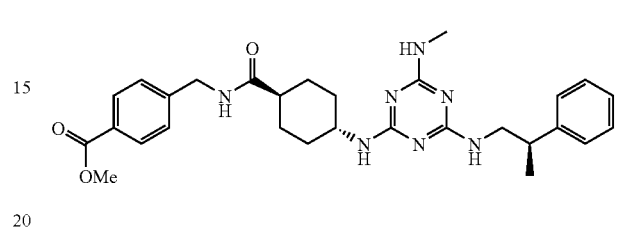

Compound 44 was prepared using the general procedure described above for Compound 34 substituting the appropriate starting materials. MS (ES+): m/e 532.3 [M+H]⁺.

Compound 45

4-(((1S,4S)-4-(4-(methylamino)-6-((R)-2-phenylpropylamino)-1,3,5-triazin-2-ylamino)cyclohexanecarboxamido)methyl)benzoic acid

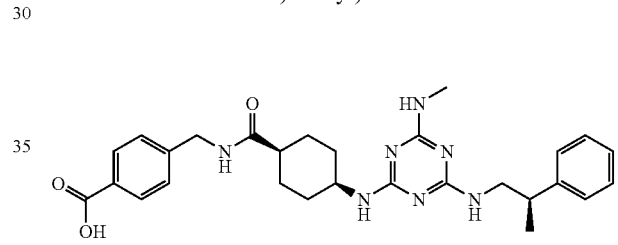

To a solution of crude methyl 4-(((1S,4s)-4-(4-(methylamino)-6-((R)-2-phenylpropylamino)-1,3,5-triazin-2-ylamino)cyclohexanecarboxamido)methyl)benzoate (Compound 43, 0.025 mmol) in CH₃CN/H₂O (1/1, 2 ml) was added 5M NaOH (0.5 ml) and stirred at room temperature for 1 hour. The reaction mixture was acidified and the solvent was evaporated to give the crude product, which was further purified by reverse phase-HPLC (Luna 5µ; C8(2), 100×21 mm, 25-60% CH₃CN/H₂O, 0.1% TFA, 19 min) to give the final product (9.0 mg, 66.9%). MS (ES+): m/e 518.35 [M+H]⁺.

Compound 46

4-(((1R,4R)-4-(4-(methylamino)-6-((R)-2-phenylpropylamino)-1,3,5-triazin-2-ylamino)cyclohexanecarboxamido)methyl)benzoic acid

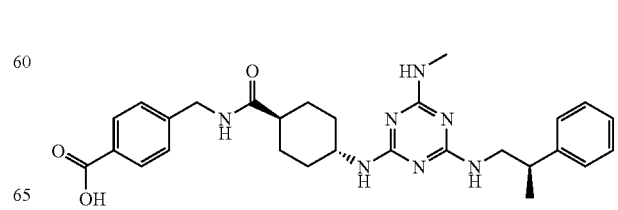

Compound 46 was prepared using the general procedure described above for Compound 45 substituting the appropriate starting materials. MS (ES+): m/e 518.4 [M+H]+.

Compound 47

2-(4-((1S,4S)-4-(4-(methylamino)-6-((R)-2-phenyl-propylamino)-1,3,5-triazin-2-ylamino)cyclohexanecarboxamido)phenyl)acetic acid

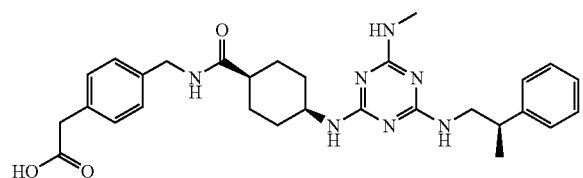

Compound 47 was prepared using the general procedure described above for Compound 45 substituting the appropriate starting materials. MS (ES+): m/e 518.2 [M+H]+.

Compound 48

(1S,4S)-4-(4-(methylamino)-6-(piperidin-1-yl)-1,3,5-triazin-2-ylamino)-N-(2-(trifluoromethyl)benzyl)cyclohexanecarboxamide

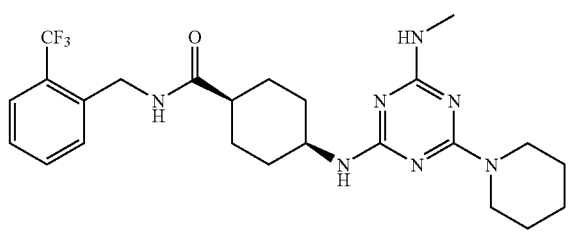

a) Preparation of cis-4-(4,6-dichloro-1,3,5-triazin-2-ylamino)cyclohexanecarboxylic acid A mixture of cyanuric chloride (493.65 mg, 2.7 mmol, 1 equivalent) in CH$_3$CN/H$_2$O (1/1, 20 ml) was cooled to 0° C. cis-4-aminocyclohexylcarboxylic acid (283.26 mg, 2.7 mmol, 1 equivalent) was added, followed by 1N NaOH (10.7 ml, 2 equivalents). The reaction was stirred at 0° C. for 15 min. LCMS analysis showed the complete consumption of the 2,4,6-trichloro-1,3,5-triazine. The crude product was used in the next step.

b) Preparation of cis-4-(4-chloro-6-(methylamino)-1,3,5-triazin-2-ylamino) cyclohexanecarboxylic acid Cold methylamine (40% (w) in water, 234 µL, 1 equivalent) was added to the crude solution of cis-4-(4,6-dichloro-1,3,5-triazin-2-ylamino)cyclohexanecarboxylic acid (2.7 mmol) in CH$_3$CN/H$_2$O (1/1, 20 ml), followed by 1N NaOH (5.34 ml, 1 equivalent). The reaction mixture was stirred at room temperature for 2-3 hrs. The crude product was used in the next step. MS (ES+): m/e 286.09 [M+H]+.

c) Preparation of cis-4-(4-(methylamino)-6-(piperidin-1-yl)-1,3,5-triazin-2-ylamino) cyclohexanecarboxylic acid To the crude solution of cis-4-(4-chloro-6-(methylamino)-1,3,5-triazin-2-ylamino)cyclohexanecarboxylic acid (~0.38 mmol) in CH$_3$CN/H$_2$O (1/1, 5 ml) was added piperidine (188 µL, 5 equivalents). The reaction mixture was heated at 80° C. overnight. The reaction solution was condensed and the crude was acidified and purified by RP-HPLC (Luna 5µ C8(2), 100×21 mm, 15-60% CH$_3$CN/H$_2$O, 0.1% TFA, 17 min) to give the product (34.9 mg). MS (ES+): m/e 335.22 [M+H]+.

d) Preparation of cis-4-(4-(methylamino)-6-(piperidin-1-yl)-1,3,5-triazin-2-ylamino)-N-(2-(trifluoromethyl)benzyl)cyclohexanecarboxamide A solution of cis-4-(4-(methylamino)-6-(piperidin-1-yl)-1,3,5-triazin-2-ylamino)cyclohexanecarboxylic acid (7.6 mg, 0.023 mmol, 1 equivalent), 2-trifluoromethyl benzylamine (4 µL, 0.03 mmol, 1.25 equivalents) and DMAP (0.6 mg, 0.2 equivalents) in dichloromethane (1.5 ml) was cooled with stirring in an ice bath. EDCl (6.6 mg, 0.034 mmol, 1.5 equivalents) was added. The reaction mixture was stirred at 0° C. for 30 min and at room temperature for 2-3 hours. The solution was diluted with dichloromethane (1 ml), which was further washed with saturated sodium bicarbonate and water. The organic layer was dried and purified by HPLC (Luna 5µ C8(2), 100×21 mm, 28-70% CH$_3$CN/H$_2$O, 0.1% TFA, 20 min) to afford the final product (8.0 mg, yield 71%). MS (ES+): m/e 492.30 [M+H]+.

Compound 49 cis-4-{[4-(methylamino)-6-(4-methyl-1-piperazinyl)-1,3,5-triazin-2-yl]amino}-N-{[2-(trifluoromethyl)phenyl]methyl}cyclohexanecarboxamide hydrochloride

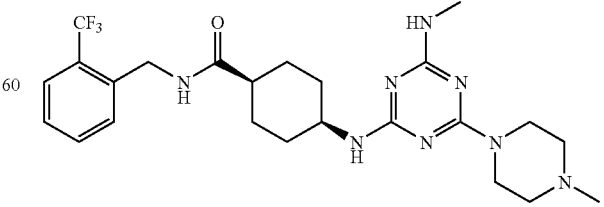

Compound 49 was prepared using the general procedure described above for Compound 48 substituting the appropriate starting materials. MS (ES+): m/e 507.2 [M+H]$^+$.

Compound 50 cis-4-(4-(methylamino)-6-(pyrrolidin-1-yl)-1,3,5-triazin-2-ylamino)-N-(2-(trifluoromethyl)benzyl) cyclohexanecarboxamide

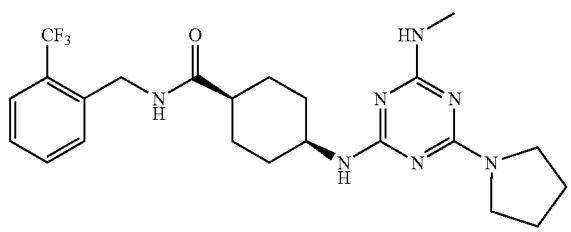

Compound 50 was prepared using the general procedure described above for Compound 48 substituting the appropriate starting materials. MS (ES+): m/e 478.2 [M+H]$^+$.

Compound 51 cis-4-(4-(benzylamino)-6-(methylamino)-1,3,5-triazin-2-ylamino)-N-(2-(trifluoromethyl)benzyl)cyclohexanecarboxamide

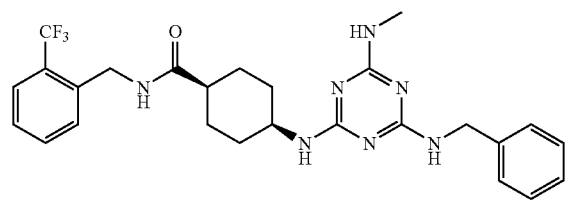

Compound 51 was prepared using the general procedure described above for Compound 48 substituting the appropriate starting materials. MS (ES+): m/e 514.2 [M+H]$^+$.

Compound 52 cis-4-(4-((2-(dimethylamino)ethyl)(methyl)amino)-6-(methylamino)-1,3,5-triazin-2-ylamino)-N-(2-(trifluoromethyl)benzyl)cyclohexanecarboxamide

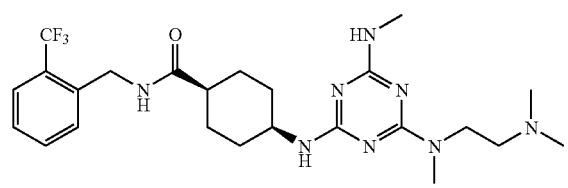

Compound 52 was prepared using the general procedure described above for Compound 48 substituting the appropriate starting materials. MS (ES+): m/e 509.2 [M+H]$^+$.

Compound 53 cis-4-(4-(azepan-1-yl)-6-(methylamino)-1,3,5-triazin-2-ylamino)-N-(2-(trifluoromethoxy)benzyl) cyclohexanecarboxamide

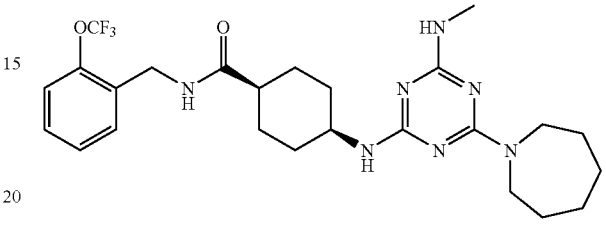

a) Preparation of 1-(4,6-dichloro-1,3,5-triazin-2-yl)azepane

A mixture of cyanuric chloride (142 mg, 0.77 mmol, 1 equivalent) in CH$_3$CN/H$_2$O (1/1, 20 ml) was cooled to 0° C. Hexamethyleneimine (86.7 μL, 0.77 mmol, 1 equivalent) was added, followed by 1N NaOH (0.77 ml). LC-MS showed the reaction had completed. The crude product was used in the next step. MS (ES+): m/e 247.18 [M+H]$^+$.

b) Preparation of cis-4-(4-(azepan-1-yl)-6-chloro-1,3,5-triazin-2-ylamino) cyclohexanecarboxylic acid To the solution of crude 1-(4,6-dichloro-1,3,5-triazin-2-yl) azepane (0.77 mmol) in CH$_3$CN/H$_2$O (1/1, 20 ml) was added cis-4-amino-cyclohexanecarboxylic acid (110 mg, 0.77 mmol, 1 equivalent), followed by 1N NaOH (1.54 ml, 1.54 mmol, 2 equivalents). The reaction mixture was stirred at room temperature 5-6 hrs. The crude product was used in the next step.

c) Preparation of cis-4-(4-(azepan-1-yl)-6-(methylamino)-1,3,5-triazin-2-ylamino) cyclohexanecarboxylic acid To the solution of crude cis-4-(4-(azepan-1-yl)-6-chloro-1,3,5-triazin-2-ylamino)cyclohexanecarboxylic acid (0.77 mmol) in CH$_3$CN/H$_2$O (1/1, 20 ml) was added methylamine (0.4 ml, 6 equivalents). The reaction mixture was heated at 80° C. overnight. The reaction solution was acidified with 6N HCl. The solution was condensed to give the crude product, which was further purified by RP-HPLC (Luna 5μ C8(2), 100×21 mm, 15-60% CH$_3$CN/H$_2$O, 0.1% TFA, 17 min) to give the product (29 mg). MS (ES+): m/e 349.33 [M+H]$^+$.

d) Preparation of cis-4-(4-(azepan-1-yl)-6-(methylamino)-1,3,5-triazin-2-ylamino)-N-(2-(trifluoromethoxy)benzyl)cyclohexanecarboxamide HATU (10.8 mg, 0.028 mmol, 1.1 equivalents) in DMF (0.2 ml) was added to the solution of cis-4-(4-(azepan-1-yl)-6-(methylamino)-1,3,5-triazin-2-ylamino) cyclohexanecarboxylic acid (8.96 mg, 0.026 mmol, 1 equivalent) in DMF (1 ml), followed by adding DIEA (11.2 μL, 0.064 mmol, 2.5 equivalents). 2-(trifluoromethyl)-benzenemethanamine (5.9 mg, 0.031 mmol, 1.2 equivalents) in DMF (0.1 ml) was added. The reaction solution was stirred at room temperature for 2 hours. LC-MS showed the reaction had completed. The reaction was diluted with EtOAc (2 ml), which was further washed with water (2×1.5 ml). The organic layer was dried and purified by RP-HPLC (Luna 5μ C8(2), 100×21 mm, 25-80% $CH_3CN/H_2O$, 0.1% TFA, 20 min) to give the final product (~7.7 mg, 57%). MS (ES+): m/e 522.4 $[M+H]^+$.

Compound 54 cis-4-(4-amino-6-(azepan-1-yl)-1,3,5-triazin-2-ylamino)-N-(2-(trifluoromethoxy)benzyl)cyclohexanecarboxamide

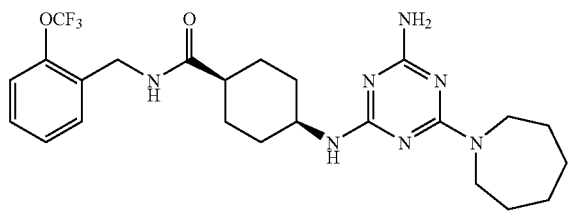

a) Preparation of cis-4-(4-amino-6-chloro-1,3,5-triazin-2-ylamino)cyclohexanecarboxylic acid At 0° C., to the mixture of 2-amino-4,6-dichlorotriazine (307 mg, 1.86 mmol, 1 equivalent) and cis-4-amino-cyclohexylcarboxylic acid (266.5 mg, 1.86 mmol, 1 equivalent) in $CH_3CN$ (20 ml) and $H_2O$ (4 ml) was added 1N NaOH (1.86 ml, 1.86 mmol, 1 equivalent). The undissolved starting material gradually disappeared. LCMS analysis showed the complete consumption of the 2-amino-4,6-dichlorotriazine. The crude product was used in the next step. MS (ES+): m/e 272.14 $[M+H]^+$.

b) Preparation of cis-4-(4-amino-6-(azepan-1-yl)-1,3,5-triazin-2-ylamino) cyclohexanecarboxylic acid To the solution of crude cis-4-(4-amino-6-chloro-1,3,5-triazin-2-ylamino)cyclohexanecarboxylic acid (~0.46 mmol) in $CH_3CN/H_2O$ (5 ml/1 ml) was added hexamethyleneimine (240 μl, ~5 equivalents). The reaction mixture was stirred at room temperature overnight. The reaction solution was condensed and the crude product was purified by RP-HPLC (Luna 5μ C8(2), 100×21 mm, 15-65% $CH_3CN/H_2O$, 0.1% TFA, 18 min) to give the product (65 mg). MS (ES+): m/e 335.3 $[M+H]^+$.

c) Preparation of cis-4-(4-amino-6-(azepan-1-yl)-1,3,5-triazin-2-ylamino)-N-(2-(trifluoromethoxy)benzyl)cyclohexanecarboxamide HATU (17.4 mg, 0.046 mmol, 1.1 equivalents) in DMF (0.2 ml) was added to the solution of cis-4-(4-amino-6-(azepan-1-yl)-1,3,5-triazin-2-ylamino)cyclohexanecarboxylic acid (13.9 mg, 0.042 mmol, 1 equivalent) in DMF (1 ml), followed by adding DIEA (18.1 ul, 0.104 mmol, 2.5 equivalents). 2-(trifluoromethyl)-benzenemethanamine (9.54 mg, 0.05 mmol, 1.2 equivalents) in DMF (0.1 ml) was added. The reaction solution was stirred at room temperature for 2 hrs. LC-MS showed the reaction has completed. The reaction was diluted with EtOAc (2 ml), which was further washed with water (2×1.5 ml). The organic layer was dried and purified by RP-HPLC (Luna 5μ C8(2), 100×21 mm, 25-80% $CH_3CN/H_2O$, 0.1% TFA, 20 min) to give the desired product (12.2 mg, 58%). MS (ES+): m/e 508.4 $[M+H]^+$.

Compound 55

(1S,4S)-4-(4-amino-6-((R)-2-phenylpropylamino)-1,3,5-triazin-2-ylamino)-N-(2-(trifluoromethoxy)benzyl)cyclohexanecarboxamide

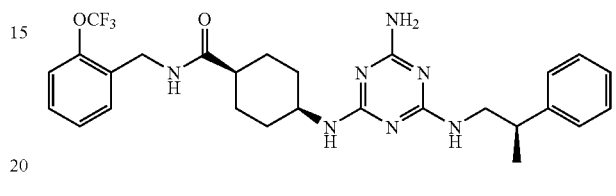

Compound 55 was prepared using the general procedure described above for Compound 53 substituting the appropriate starting materials. MS (ES+): m/e 544.4 $[M+H]^+$.

Compound 56 trans-4-(4-(methylamino)-6-(4-methylpiperazin-1-yl)-1,3,5-triazin-2-ylamino)-N-(2-(trifluoromethyl)benzyl)cyclohexanecarboxamide

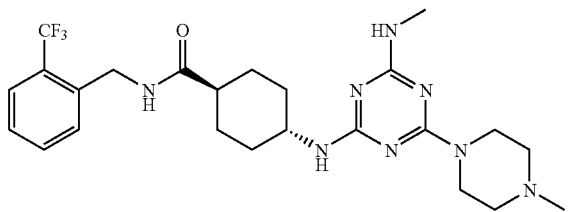

a) Preparation of 4-chloro-N-methyl-6-(4-methylpiperazin-1-yl)-1,3,5-triazin-2-amine A mixture of cyanuric chloride (3.86 g, 20.9 mmol, 1 equivalent) in $CH_3CN/H_2O$ (1/1, 200 ml) was cooled to 0° C. Methylamine solution in water (40% (w), 1.83 ml, 20.9 mmol, 1 equivalent) was added, followed by 1N NaOH (20.9 ml, 20.9 mmol, 1 equivalent). The reaction mixture was stirred at 0° C. for 15 min and LCMS showed the reaction had completed. At 0° C., N-methylpiperazine (2.3 ml, 20.9 mmol, 1 equivalent) was added, followed by 1N NaOH (4.2 ml, 0.2 equivalents). The solution turned to clear. The solvent was evaporated to give the crude product which was further purified with silica gel chromatography (eluant 70% B, solvent B is 10% MeOH in DCM with 1% $Et_3N$) to give the product (1.8 g). $^1H$ NMR ($CDCl_3$, 400 MHz): δ2.33 (s, 3H), 2.44 (br, 4H), 2.95&2.96 (3H), 3.86 (br, 4H), 5.1&5.7 (br, 1H).

b) Preparation of trans-4-(4-(methylamino)-6-(4-methylpiperazin-1-yl)-1,3,5-triazin-2-ylamino) cyclohexanecarboxylic acid trans-4-Aminocyclohexylcarboxylic acid (472 mg, 3.30 mmol, 8 equivalents) and triethylamine (0.46 ml, 3.30 mmol, 8 equivalents) was added to the solution of 4-Chloro-N-methyl-6-(4-methylpiperazin-1-yl)-1,3,5-triazin-2-amine (100 mg, 0.412 mmol, 1 equivalent) in CH₃CN (8 ml). The reaction mixture was heated at 80° C. for 16 hours. The solvent was evaporated and the crude product was purified with RP-HPLC (Luna 5μ, C8(2), 100×21 mm, 2-45% CH₃CN/H₂O, 0.1% TFA, 25 min) to give the product (18.4 mg, 10%). MS (ES+): m/e 350.13 [M+H]⁺.

c) Preparation of trans-4-(4-(methylamino)-6-(4-methylpiperazin-1-yl)-1,3,5-triazin-2-ylamino)-N-(2-(trifluoromethyl)benzyl)cyclohexanecarboxamide A solution of trans-4-(4-(methylamino)-6-(4-methylpiperazin-1-yl)-1,3,5-triazin-2-ylamino)cyclohexanecarboxylic acid as TFA salt (18.4 mg, 0.04 mmol, 1 equivalent), 2-trifluoromethyl benzylamine (10.5 mg, 0.06 mmol, 1.5 equivalents) and DMAP (1.3 mg, 0.26 equivalents) in dichloromethane (1 ml) was cooled with stirring in an ice bath. EDCl (12.7 mg, 0.066 mmol, 1.65 equivalents) was added. The reaction mixture was stirred at room temperature for 16 hours. The solution was diluted with dichloromethane (1 ml), which was further washed with saturated sodium bicarbonate and water. The solvent was removed to give the crude product, which was further purified by RP-HPLC (Luna 5μ, C8(2), 100×21 mm, 5-40% CH₃CN/H₂O, 0.1% TFA, 25 min) to give the final product (5.33 mg, 21.5%). MS (ES+): m/e 507.21 [M+H]⁺.

Compound 57

3-(4-(methylamino)-6-(4-methylpiperazin-1-yl)-1,3,5-triazin-2-ylamino)-N-(2-(trifluoromethyl)benzyl)cyclohexanecarboxamide

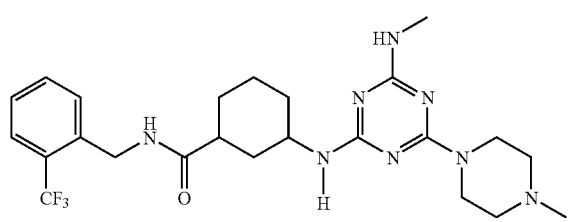

a) Preparation of 3-amino-N-(2-(trifluoromethyl)benzyl)cyclohexanecarboxamide

To a solution of 3-(Boc-amino)cyclohexanecarboxylic acid (500 mg, 2.055 mmol, 1 equivalent) in dimethylformamide (10 ml) was added O-(7-Azabenzotriazol-1-yl)-N,N,N',N'-tetramethyluronium hexafluorophosphate (HATU, 781 mg, 2.055 mmol, 1 equivalent) and diisopropylethylamine (0.716 ml, 4.11 mmol, 2 equivalents). 2-trifluoromethyl benzylamine (360 mg, 2.055 mmol, 1 equivalent) was added and the reaction mixture was stirred at room temperature overnight. The solvent was evaporated to give the crude product, which was purified with RP-HPLC. The purified compound was treated with 50% TFA in DCM (20 ml) at room temperature for 2 hours, and then the solvents were removed in vacuo. The product (103 mg, 12% yield) was carried onto the next step without further purification. MS (ES+): m/e 301.06 [M+H]⁺.

b) Preparation of 3-(4-(methylamino)-6-(4-methylpiperazin-1-yl)-1,3,5-triazin-2-ylamino)-N-(2-(trifluoromethyl)benzyl)cyclohexanecarboxamide The solution of 4-chloro-N-methyl-6-(4-methylpiperazin-1-yl)-1,3,5-triazin-2-amine (30.0 mg, 0.084 mmol, 1 equivalent) and 3-amino-N-(2-(trifluoromethyl)benzyl) cyclohexanecarboxamide as TFA salt (103 mg, 0.248 mmol, 2.95 equivalents) in CH₃CN/H₂O (1/1, 2 ml) was adjusted to pH 9-10 with 1N NaOH. The resulting solution was heated at 80° C. for 16 hours. The solvent was removed under vacuo to give the crude product, which was purified with RP-HPLC (Luna 5μ, C8(2), 100×21 mm, 10-50% CH₃CN/H₂O, 0.1% TFA, 25 min) to give the final compound (0.94 mg, 1.8%). MS (ES+): m/e 507.17 [M+H]⁺.

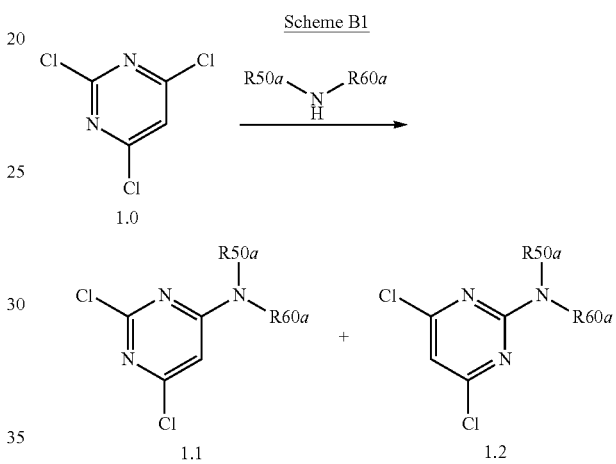

Scheme B1

Scheme B1 represents a general reaction scheme for preparing certain intermediates 1.1 and 1.2. Treatment of 2,4,6-trichloropyrimidine (commercially available) with amine HNR50aR06a (commercially available or made from commercially available starting materials using methods known to those skilled in the art) with solvent such as THF and at temperatures between 0° C. to 50° C. provides intermediates 1.1 and 1.2.

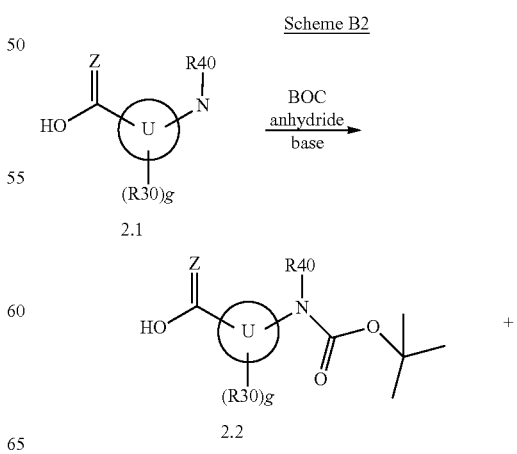

Scheme B2

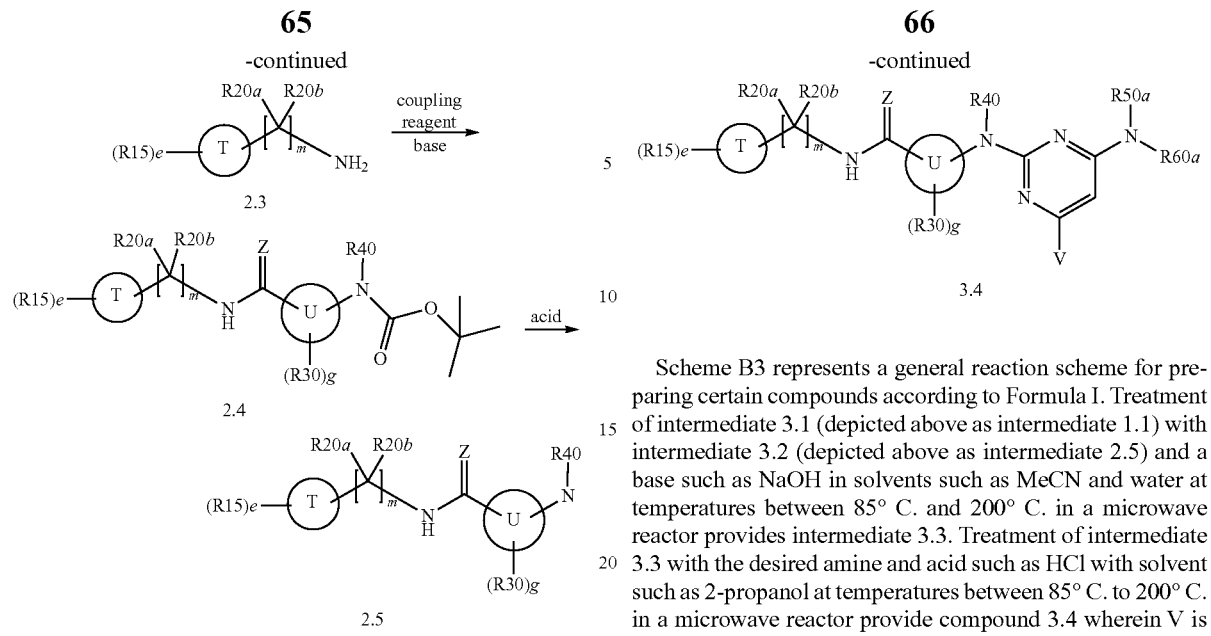

Scheme B2 represents a general reaction scheme for preparing certain intermediates depicted above as 2.5. Treatment of intermediate 2.1 (commercially available or made from commercially available starting materials using methods known to those skilled in the art) with BOC anhydride and a base (such as NaOH) in a solvent (such as isopropanol and water) provides intermediate 2.2. Treatment of intermediate 2.2 with an amine 2.3 and a coupling reagent (such as 1H-1,2,3-benzotriazol-1-yloxy-tris(dimethylamino)-phosphonium hexafluorophosphate (BOP) reagent) and a base (such as triethylamine) in a solvent (such as DMF) provides intermediate 2.4. Treatment of intermediate 2.4 with acid (such as trifluoroacetic acid) in a solvent (such as methylene chloride) provides intermediate 2.5.

Scheme B3

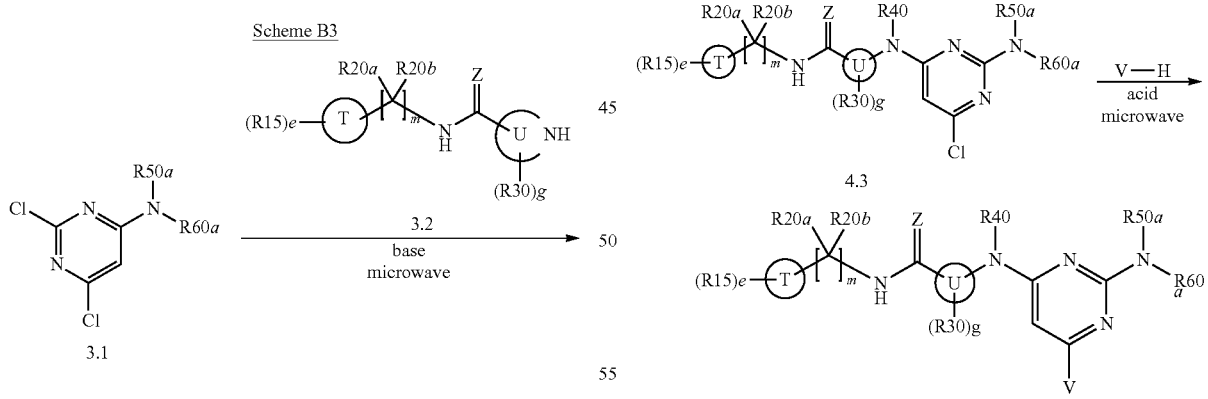

Scheme B3 represents a general reaction scheme for preparing certain compounds according to Formula I. Treatment of intermediate 3.1 (depicted above as intermediate 1.1) with intermediate 3.2 (depicted above as intermediate 2.5) and a base such as NaOH in solvents such as MeCN and water at temperatures between 85° C. and 200° C. in a microwave reactor provides intermediate 3.3. Treatment of intermediate 3.3 with the desired amine and acid such as HCl with solvent such as 2-propanol at temperatures between 85° C. to 200° C. in a microwave reactor provide compound 3.4 wherein V is NR50bR60b.

Scheme B4

Scheme B4 represents a general reaction scheme for preparing certain compounds according to Formula I. Treatment of intermediate 4.1 (depicted above as intermediate 1.2) with intermediate 4.2 (depicted above as intermediate 2.5) and a base such as NaOH in solvents such as MeCN and water at temperatures between 85° C. and 200° C. in a microwave reactor provides intermediate 4.3. Treatment of intermediate 4.3 with the desired amine and acid such as HCl with solvent such as 2-propanol at temperatures between 85° C. to 200° C. in a microwave reactor provide compound 4.4 wherein V is NR50bR60b.

Intermediate 1 cis-4-amino-N-{[2-(trifluoromethyl)phenyl]methyl}cyclohexanecarboxamide

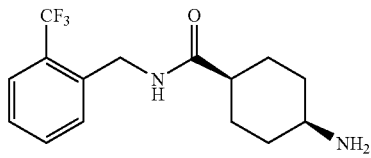

Step 1: Preparation of cis-4-({[(1,1-dimethylethyl)oxy]carbonyl}amino) cyclohexanecarboxylic acid A 250 mL round-bottom flask charged with argon was equipped with a magnetic stir bar and an oil bubbler. Cis-4-aminocyclohexanecarboxylic acid (9.27 g, 64.7 mmol), isopropanol (83 mL) and 1N NaOH (70.6 mL, 70.6 mmol) were delivered to the flask at room temperature. After all of the solid was dissolved, bis(tert-butyl) dicarbonate (15.54 g, 71.2 mmol) was added and the mixture was maintained at that temperature for 21 hours, before it was determined to be complete by $^1$H NMR. The crude mixture was washed with hexanes (3×100 mL). Afterwards, 100 mL of 1N HCl was added to the aqueous layer and the mixture was extracted with ethyl acetate (300 mL). The organic phase was dried over $Na_2SO_4$, filtered and concentrated to give 12.85 g of cis-4-({[(1,1-dimethylethyl)oxy]carbonyl}amino)cyclohexanecarboxylic acid (52.8 mmol, 82%) as an off-white solid.

Step 2: Preparation of 1,1-dimethylethyl{cis-4-[({[2-(trifluoromethyl)phenyl]methyl}amino) carbonyl]cyclohexyl}carbamate A 250 mL round-bottom flask charged with argon was equipped with a magnetic stir bar, prior to the addition of cis-4-({[(1,1-dimethylethyl)oxy]carbonyl}amino) cyclohexanecarboxylic acid (15.54 g, 63.9 mmol), 2-(trifluoromethyl)benzylamine (8.95 mL, 63.9 mmol) and 100 mL of DMF at room temperature. Afterwards, triethylamine (26.7 mL, 192 mmol) was added and the solution was allowed to stir for several minutes before a separate solution of 1H-1,2,3-benzotriazol-1-yloxy-tris(dimethylamino)-phosphonium hexafluorophosphate (BOP reagent, 28.3 g, 63.9 mmol) dissolved in 60 mL of DMF was delivered to the mixture at room temperature. The reaction was maintained at that temperature for 2 hours, before it was determined to be complete by LCMS (Rt=8.34 min and m/e 401 [M+1]$^+$). Pouring the crude mixture into a vigorously stirring 50/50 solution of saturated sodium bicarbonate and water (1.6 L), resulted in the precipitation of the desired product as an off-white solid. The solid was recovered by vacuum filtration and dried for 24 hours under vacuum to give 24.88 g of 1,1-dimethylethyl{cis-4-[({[2-(trifluoromethyl)phenyl]nethyl}amino)carbonyl]cyclohexyl}carbamate (62.1 mmol, 97%). MS (ES) m/e 401 [M+H]$^+$.

Step 3: Preparation of cis-4-amino-N-{[2-(trifluoromethyl)phenyl]methyl}cyclohexane carboxamide A 500 mL round bottom flask equipped with a magnetic stir bar was charged with 1,1-dimethylethyl{cis-4[({[2-(trifluoromethyl)phenyl]methyl}amino)carbonyl]cyclohexyl}carbamate (24.88 g, 62.1 mmol) and DCM (100 mL) at room temperature. Trifluoroacetic acid (100 mL) was added slowly, and the reaction was maintained at room temperature for 1 hour, before it was determined to be complete by LCMS (Retention time=5.71 min and m/e 301 [M+H]$^+$). The volatiles were removed by rotary evaporation and the crude oil was dissolved in ethyl acetate and washed with saturated sodium bicarbonate solution (3×200 mL). The organic phase was dried over $Na_2SO_4$, filtered and concentrated to give 18.3 g of the title compound (60.9 mmol, 98%) as an off-white solid. MS (ES) m/e 301 [M+H]$^+$.

Intermediate 2

2,6-dichloro-N-methyl-4-pyrimidinamine (Intermediate 3

4,6-dichloro-N-methyl-2-pyrimidinamine

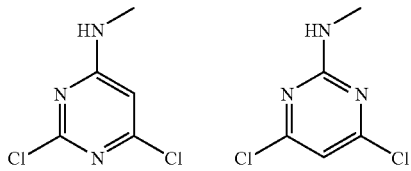

To a 0° C. mixture 2,4,6-trichloropyrimidine (0.50 g, 2.7 mmol) in THF (3 mL) was added methyl amine (2M THF, 3.0 mL, 6.0 mmol) dropwise. The reaction mixture was warmed to room temperature and stirred for 30 minutes, at which time LCMS indicated the formation of the desired product. The reaction mixture was treated with water (10 mL) and extracted with EtOAc (2×10 mL). The organics were washed with brine (10 mL), dried ($Na_2SO_4$), and evacuated. The crude material was purified by column chromatography (Gradient from 0-30% EtOAc in Hexanes) to afford 180 mg (1.01 mmol, 38%) of 2,6-dichloro-N-methyl-4-pyrimidinamine and 150 mg (0.85 mmol 31%) of 4,6-dichloro-N-methyl-2-pyrimidinamine. MS (ES+) m/e 178 [M+H]$^+$ for each.

Compound 58 cis-4-({[4-(methylamino)-6-[(phenylmethyl)amino]-2-pyrimidinyl]amino}-N-{[2-(trifluoromethyl)phenyl]methyl}cyclohexanecarboxamide

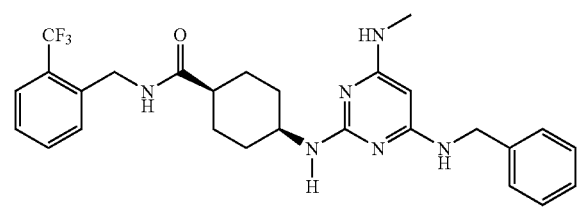

Step 1: Preparation of cis-4-{[4-chloro-6-(methylamino)-2-pyrimidinyl]amino}-N-{[2-(trifluoromethyl)phenyl]methyl}cyclohexanecarboxamide To a solution of 2,6-dichloro-N-methyl-4-pyrimidinamine (360 mg, 2.0 mmol) and cis-4-amino-N-{[2-(trifluoromethyl)phenyl]methyl}cyclohexanecarboxamide (Intermediate 1) trifluoroacetate (829 mg, 2.0 mmol), in MeCN/$H_2O$ (1:1, 5 mL) was added 1N NaOH solution until a pH of 12 was achieved. The mixture was irradiated in the microwave for 4 hours at 170° C., at which time LCMS indicated the formation of the desired product. The reaction mixture was extracted with EtOAc (2×50 mL), washed with water (2×50 mL), dried (Na₂SO₄), and concentrated to afford a waxy solid. The crude material was purified by column chromatography (Gradient from 0-5% MeOH in CH₂Cl₂) to afford 300 mg (0.68 mmol, 34%) of a colorless wax MS (ES+) m/e 442 [M+H]⁺. Regiochemistry was verified by 2D NMR analysis.

Step 2: Preparation of cis-4-({4-(methylamino)-6-[(phenylmethy)amino]-2-pyrimidinyl}amino)-N-{[2-(trifluoromethyl)phenyl]methyl}cyclohexanecarboxamide To a solution of cis-4-{[4-chloro-6-(methylamino)-2-pyrimidinyl]amino}-N-{[2-(trifluoromethyl)phenyl]methyl}cyclohexanecarboxamide (50.0 mg, 0.11 mmol) and benzylamine (59.0 mg, 0.55 mmol) in 2-propanol (3 mL) was added one drop of concentrated HCl. The mixture was irradiated in the microwave for 3 hours at 170° C., at which time LCMS indicated the formation of the desired product. The crude reaction mixture was filtered and purified directly by preparative HPLC (gradient; 30-80% CH₃CN:H₂O (0.1% TFA)), to afford the title compound (30 mg, 0.58 mmol, 52%). MS (ES+) m/e 513 [M+H]⁺.

Compound 59 cis-4-{[4-(methylamino)-6-(4-methyl-1-piperazinyl)-2-pyrimidinyl]amino}-N-{[2-(trifluoromethyl)phenyl]methyl}cyclohexanecarboxamide

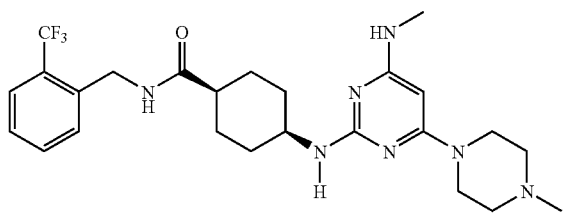

Compound 59 was prepared using the general procedure described above for Compound 58 substituting benzylamine with the appropriate primary or secondary amine. MS (ES+): m/e 506 [M+H]⁺.

Compound 60 cis-4-[(4-(methylamino)-6-{[(2R)-2-phenylpropyl]amino}-2-pyrimidinyl)amino]-N-{[2-(trifluoromethyl)phenyl]methyl}cyclohexanecarboxamide

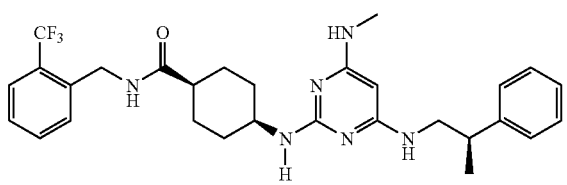

Compound 60 was prepared using the general procedure described above for Compound 58 substituting benzylamine with the appropriate primary or secondary amine. MS (ES+): m/e 541 [M+H]⁺.

Compound 61 cis-4-{[4-[[2-(dimethylamino)ethyl](methyl)amino]-6-(methylamino)-2-pyrimidinyl]amino}-N-{[2-(trifluoromethyl)phenyl]methyl}cyclohexanecarboxamide

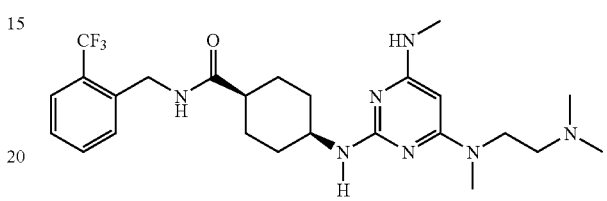

Compound 61 was prepared using the general procedure described above for Compound 58 substituting benzylamine with the appropriate primary or secondary amine. MS (ES+): m/e 508 [M+H]⁺.

Compound 62 cis-4-{[2-(methylamino)-6-(4-methyl-1-piperazinyl)-4-pyrimidinyl]amino}-N-{[2-(trifluoromethyl)phenyl]methyl}cyclohexanecarboxamide

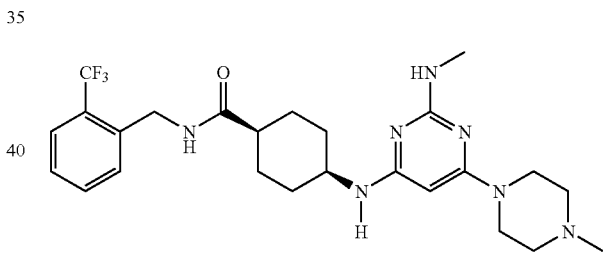

Compound 62 was prepared using the general procedure described above for Compound 58 substituting 2,6-dichloro-N-methyl-4-pyrimidinamine with 4,6-dichloro-N-methyl-2-pyrimidinamine and benzylamine with the appropriate primary or secondary amine. MS (ES+): m/e 506 [M+H]⁺.

As used above, the phrase "using the general procedure described above" indicates that the procedure used employs similar, but not necessarily identical, reaction conditions to those referred to.

Biological Activity

The compounds of the invention are sEH inhibitors. The compounds of the invention, therefore, are useful in the treatment of hypertension and other conditions involving sEH activity. As stated above, mEH provides an important detoxification pathway in mammals. Compounds that exhibit pharmacological selectivity for sEH over mEH therefore are desirable in the methods of treatment described below. Accordingly, in one embodiment the invention is directed to a compound of the invention wherein the compound exhibits a selectivity ratio equal to or greater than 10:1 for sEH over mEH. In another embodiment the invention is directed to a compound of the invention wherein the compound exhibits a selectivity ratio equal to or greater than 100:1 for sEH over mEH. In another embodiment the invention is directed to a compound of the invention wherein the compound exhibits a selectivity ratio equal to or greater than 1000:1 for sEH over mEH.

The biological activity of the compounds of the invention can be determined using any suitable assay for determining the activity of a candidate compound as an sEH and/or mEH inhibitor, as well as suitable tissue and/or in vivo models.

sEH Expression and Purification

The sEH gene is subjected to polymerase chain reaction (PCR) starting with a cDNA clone of human sEH, using PCR primers 5' aatcaqcqatcqccATGACGCTGCGCGCGG and 3' agatatctagactt CTACATC TTTGAGACC. The PCR-amplified sEH DNA is inserted into the AsiSI and Xba I site of pcDNA3.1 mammalian expression vector (Invitrogen, V790-20), containing sequences of two affinity tags 6×His and Streptavidin binding peptide (MDEKTTGWRGGH VVEGLAGELEQLRARLEHHPQGQREP) (Keefe, A. D., et al., Protein Expr. Purif., 23, 440-446 (2001). The sequence of the human sEH expressing vector is confirmed by sequencing. The plasmid is purified using QIAGEN Plasmid Maxi Kit (Cat. No. 12162).

To produce the human sEH protein, pcDNA3.1-sEH plasmid is transfected into FreeStyle 293-F cells using FreeStyle 293 Expression System (Invitrogen, Catalog no. K9000-01). Cells are grown in FreeStyle™ 293 Expression Medium at 37° C. with constant rotation at 120 revolutions/minute for 48 hours and then harvested and lysed in an ice cold lysis buffer (40 mM Tris-HCl pH 7.5, 300 mM NaCl, 1% TRITON TX-100, proteis inhibirots cocktail). The crude cell extract is centrifuged at 13,000 g for 20 minutes to remove cell debris. The supernatant is loaded onto a column packed with UltraLink Immobilazed Streptavidin Plus Sepharose (Pierce, Catalog no. 53117). The protein is purified using the affinity of the SBP tag (Streptavidin Binding Peptide) to the Streptavidin. The column with bound sEH is washed with Wash Buffer (50 mM Tris-HCl 7.5, 150 mM NaCl, 0.03% Brij-35, 5 mM BME and protease inhibitor cocktail).

The purified protein is eluted from the Streptavidin Sepharose column with 2 mM biotin in Wash buffer. Elution fractions are collected and analyzed on 4-12% SDS-PAGE resolving gel (Invitrogen, NPO0322 BOX). Protein concentrations are determined with the Pierce BCA assay (Pierce, Rockford, Ill.) using BSA as a standard.

The purified protein is aliquoted and kept at −80° C.

Assay to Test the Hydrolyse Activity of Human Recombinant Soluble Epoxide Hydrolyse (hsEH)

The biological activity of the compounds of the invention can be measured using the nonfluorescent EnzChek epoxide hydrolase substrate (Molecular Probes, Catalog #E33956). In the presence of epoxide hydrolases, the nonfluorescent EnzChek epoxide hydrolase substrate produces a bright blue-fluorescent product with excitation and emission maxima of approximately 350 nm and 455 nm, respectively.

Assays can be performed in an assay buffer containing 50 mM HEPES (pH 8). The final concentration of soluble epoxide hydrolase enzyme (full length, prepared as indicated above) in the assay is 10 nM.

The compound is re-suspended in 100% DMSO and then diluted in the assay buffer to a 4 times the final concentration (0.8% DMSO). The hsEH enzyme is incubated against a range of compound concentrations, shaking, for 5 minutes at room temperature. The hydrolysis reaction is initiated by adding diluted EnzChek substrate (final concentration 10 uM). The reaction is run at room temperature and readings are taken every 30 seconds for 30 minutes. The fluorescence is measured at an excitation of 350 nM and an emission of 455 nM.

The activity of the compound is calculated as the % of inhibition using the following equation: 100*(1−(slope of enzyme+inhibitor/slope of enzyme alone) and expressed as IC50 values (the concentration of inhibitor that blocks enzyme activity to 50%).

In Vitro Fluorescence Assay

Inhibition of Soluble Expoxide Hydrolase (sEH) activity is measured in a fluorescent assay based upon the format described by Wolf et al. (Analytical Biochemistry Vol. 355 (2006) pp. 71-80). In the presence of sEH, PHOME ((3-Phenyl-oxiranyl)-acetic acid cyano-(6-methoxy-naphthalen-2-yl)-methyl ester), is hydrolyzed to a diol which goes through an intramolecular cyclization and the release and decomposition of cyanohydrin (products=cyanide and 6-methoxy-2-naphthaldehyde). Production of 6-methoxy-2-naphthaldehyde is monitored at excitation of 360 nm and an emission of 465 nm.

The assay is used in a quenched assay format by sequentially adding enzyme (5 uL; 200 μM sEH in 25 mM Hepes at pH 7.0, 0.01% CHAPS (w/v), 0.005% Casein (w/v); 10 minute ambient pre-incubation after addition) then PHOME substrate (5 ul; 10 uM PHOME substrate in 25 mM Hepes at pH 7.0, 0.01% CHAPS (w/v), 0.005% Casein (w/v)) to a 384 well assay plate (Greiner 784076) pre-stamped with 25-100 nL compound at the desired concentration. The reaction is incubated for 30 minutes at room temperature, then quenched by the addition of stop solution (5 uL; 10 mM ZnSO4 in 25 mM Hepes at pH 7.0, 0.01% CHAPS (w/v), 0.005% Casein (w/v)). Microtiter plates are centrifuged after each addition for 30 seconds at 500 rpm. The fluorescence is measured on an EnVision plate reader platform (Perkin Elmer) using a 360 nm excitation filter, 465 nm emission filter, and 400 nm dichroic filter.

Compounds are first prepared in neat DMSO at a concentration of 10 mM, then diluted as required to achieve the desired assay concentration. For inhibition curves, compounds are diluted using a three fold serial dilution and tested at 11 concentrations e.g. 50 μM-0.8 nM or 25 μM-0.42 nM or 2.5 μM to 42 μM). Curves are analysed using ActivityBase and XLfit, and results are expressed as $pIC_{50}$ values.

Cell-Based sEH Inhibitor Assay

Cell based sEH inhibition is measured using the 14,15-DHET immunoassay ELISA kit available from Detroit R&D (Cat. No. DH1), according to the following procedure:

HEK293 cells (BioCat ID 80556) are transduced by sEH BacMam virus to increase sEH expression (other cell lines may be suitable) as follows: One day before the experiment, 1.5 million HEK293 cells (BioCat ID 80556) are seated in 3 ml of DMEM/F12 (with L-Glutamine, with 15 mM HEPES, pH7.30, from Media Prep Lab), with 10% fetal bovine serum (from SAFC Biosciences, Cat. No. 12176-1000M), no antibiotic, in a 25 cm$^2$ flask (from Corning Incorporated, Cat. No. 430639) and 30 μL sEH BacMam virus is added. The cells are gently mixed then incubated at 37° C., 5% $CO_2$, for 24 hours.

The cells are trypsinized to release them from the growth flask, washed once with PBS, then re-suspended in 5 mL DMEM/F12 without phenol red (from Media Prep lab). Cell density should be approximately $3*10^5$ cells/mL (=300 cells/μL), counted using the Cedex AS[20] (from Innovatis).

The cells are then diluted in DMEM/F12 to 5.1 cells/μL, and 984/well (=500 cells/well) of this cell suspension is transferred to an assay plate (96 well, clear polystyrene, flat bottom, from Whatman, Cat. No. 7701-1350).

2 μL of the diluted test compound is then added to the cells in the assay plate. The reaction plate is shaken gently and incubated at room temperature for 30 min, after which 104 of substrate solution is added (substrate solution is prepared by diluting 1.244 of 14,15-EET from Cayman Chemical, Cat. No. 50651 with 8.244 DMEM/F12). The assay plate is then incubated for one hour at room temperature.

After the 1 hour reaction, the reaction mixture is diluted 3 fold with provided sample dilution buffer (ex. Add 220 μL to the 110 μL reaction mixture), mixed well, and spun for 5 min at 500 rpm.

100 μL of the diluted reaction mixture is then transferred from the reaction plates to the ELISA plates, and the ELISA is performed according to the instructions provided in the kit.

IC50s and pIC50s are then calculated. The IC50 can be calculated directly using the 14, 15-DHET concentration or using the % inhibition [% inhibition=100*(1-(sample DHET—0 cell DHET)/(500 cells DHET—0 cell DHET)].

Compounds are first prepared in neat DMSO at a concentration of 0.5 mM, then diluted as required to achieve the desired assay concentration. For inhibition curves, compounds are diluted using a three fold serial dilution and tested at 9 concentrations (e.g. 10 μM-1.5 nM). Curves are analysed using ActivityBase and XLfit, and results are expressed as pIC50 values.

Biological Activity Results

All of the compounds of the invention are believed to have activity as sEH inhibitors. Where the assay for a particular compound had been performed two or more times, the following conclusion regarding their activities is based on the average of individual experiments: Of the exemplified compounds that were tested, all were found to have an IC50 in the range of 0.1 and 25,000 nM.

Methods of Use

The compounds of the invention inhibit the sEH enzyme and can be useful in the treatment of conditions wherein the underlying pathology is (at least in part) attributable to sEH involvement or in conditions wherein sEH inhibition offers some clinical benefit even though the underlying pathology is not (even in part) attributable to sEH involvement. Examples of such conditions include hypertension, organ failure/damage (including heart failure, renal failure, and liver failure), peripheral vascular disease (including ischemic limb disease, intermittent claudication, endothelial dysfunction, erectile dysfunction, Raynaud's disease, and diabetic vasculopathies e.g. retinopathy), atherothrombotic disorders (including coronary artery disease, coronary vasospasm, angina, stroke, myocardial ischemia, myocardial infarction, and hyperlipidemia), metabolic disorders (including diabetes), and inflammatory disorders (including arthritis, inflammatory pain, overactive bladder, asthma, and COPD). Accordingly, in another aspect the invention is directed to methods of treating such conditions.

Essential hypertension is commonly associated with the development of significant end organ damage such as renal, endothelial, myocardial, and erectile dysfunction. Such conditions occur "secondary" to the elevated systemic arterial blood pressure. Secondary conditions may be prevented by treatment of the underlying ("primary") cause. Accordingly, in another aspect the invention is directed to methods of preventing such secondary conditions.

In addition, sEH is indirectly involved in the regulation of platelet function through its effect on EETs. Drugs that inhibit platelet aggregation are believed to decrease the risk of atherthrombotic events, such as myocardial infarction and stroke, in patients with established cardiovascular atherosclerotic disease. Accordingly, in another aspect the invention is directed to methods of preventing atherothrombotic events, such as myocardial infarction and stroke in patients with a history of recent myocardial infarction, stroke, transient ischemic attacks, unstable angina, or atherosclerosis.

The methods of treating and the methods of preventing described above comprise administering a safe and effective amount of a compound of the invention to a patient in need thereof.

As used herein, "treatment" in reference to a condition means: (1) the amelioration or prevention of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to significantly induce a positive modification in the condition to be treated but low enough to avoid serious side effects (at a reasonable benefit/risk ratio) within the scope of sound medical judgment. A safe and effective amount of a compound of the invention will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, but can nevertheless be determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the amount administered and the duration such regimens are administered, for a compound of the invention depend on the condition being treated, the severity of the condition being treated, the age and physical condition of the patient being treated, the medical history of the patient to be treated, the nature of concurrent therapy, the particular route of administration chosen, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. By way of general guidance, the daily oral dosage of each active ingredient, when used for the indicated effects, will range between about 0.001 to 1000 mg/kg of body weight. Typical daily dosages range from 1 mg to 1000 mg.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into a pharmaceutical composition prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein a safe and effective amount of a compound of the invention can be extracted and then given to the patient such as with powders, syrups, and solutions for injection. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds. Conversely, the pharmaceutical compositions of the invention typically contain more than one pharmaceutically-acceptable excipient. However, in certain embodiments, the pharmaceutical compositions of the invention contain one pharmaceutically-acceptable excipient.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when comingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excepients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Rem-* ington's *Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

What is claimed is:

1. A compound of Formula I:

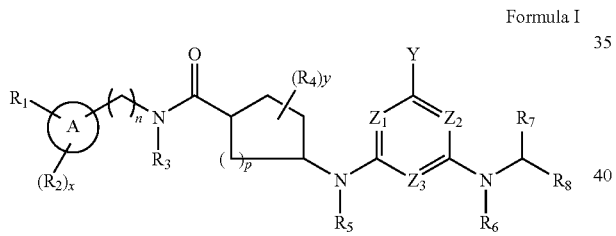

Formula I or a pharmaceutically acceptable salt thereof, wherein:

is a 6-membered aryl or heteroaryl ring;

$R_1$ is hydrogen, $CO_2H$, $CO_2(C_1-C_6)$alkyl, $CONR'R''$ wherein $R'$ and $R''$ are each independently hydrogen or $(C_1-C_6)$alkyl, araalkyl, heteroaralkyl, —$(C_2-C_{10})$alkylene-$NR'R''$, —$(C_2-C_{10})$alkylene-$OR'$, and —O—$(C_1-C_6)$alkyl, —S—$(C_1-C_6)$alkyl, any of which may be optionally substituted on carbon with 1, 2, or 3 halo;

each $R_2$ is if present independently halo, $(C_1-C_6)$alkyl, —O—$(C_1-C_6)$alkyl, —S—$(C_1-C_6)$alkyl, any of which may be optionally substituted on carbon with 1, 2, or 3 halo;

n is 0 or 1;

x is 0, 1, or 2;

$R_3$ is hydrogen or $(C_1-C_6)$alkyl;

p is 0, 1, 2, or 3;

each $R_4$ if present is independently halo, $(C_1-C_6)$alkyl, or —O—$(C_1-C_6)$alkyl, —S—$(C_1-C_6)$alkyl, any of which may be optionally substituted on carbon with 1, 2, or 3 halo, or taken together with the attached carbon forms C=O;

y is 0, 1, or 2;

$R_5$ is hydrogen or $(C_1-C_6)$alkyl;

$R_6$ is hydrogen or $(C_1-C_6)$alkyl;

$R_7$ is hydrogen, halo, or $(C_1-C_6)$alkyl; or $R_6$ and $R_7$ together with the atoms to which they are attached, form a 3-10 membered ring, optionally substituted on carbon with 1, 2, or 3 groups selected from halo, $(C_1-C_6)$alkyl, and —O—$(C_1-C_6)$alkyl, —S—$(C_1-C_6)$alkyl, any of which may be optionally substituted on carbon with 1, 2, or 3 halo, or taken together with the attached carbon forms C=O;

$R_8$ is hydrogen, halo, or $(C_1-C_6)$alkyl, or is

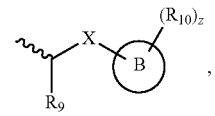

wherein " $\sim$ " indicates the point of attachment and wherein $R_9$ is hydrogen, halo, or $(C_1-C_6)$alkyl;

X is absent or is O, $S(O)_m$ wherein m is 0, 1, or 2, —$CH_2$—S—, —$CH_2$—O—, —$CH_2$—NH—, or —$CH_2$—N($C_1$-$C_6$)alkyl-;

is $(C_3-C_6)$cycloalkyl, $(C_3-C_6)$heterocycloalkyl, aryl, or heteroaryl;

each $R_{10}$ if present is independently halo, $(C_1-C_6)$alkyl, —O—$(C_1-C_6)$alkyl, —S—$(C_1-C_6)$alkyl, any of which may be optionally substituted on carbon with 1, 2, or 3 halo, or taken together with the attached carbon forms C=O;

z is 0, 1, or 2;

$Z_1$, $Z_2$, and $Z_3$ are N;

Y is H, halo, $OR_{11}$, or $NR_{11}R_{12}$;

$R_{11}$ is hydrogen or $(C_1-C_6)$alkyl; and $R_{12}$ is hydrogen, $(C_1-C_6)$alkyl, aryl, aralkyl, $(C_3-C_6)$cycloalkyl, -alkylene-$(C_3-C_6)$cycloalkyl, $(C_3-C_6)$heterocycloalkyl, -alkylene-$(C_3-C_6)$heterocycloalkyl, heteroaryl, heteroaralkyl, any of which may be optionally substituted on carbon with 1 or 2 groups selected from halo, $(C_1-C_6)$alkyl, —O—$(C_1-C_6)$alkyl, —S—$(C_1-C_6)$alkyl.

2. A compound of Formula II:

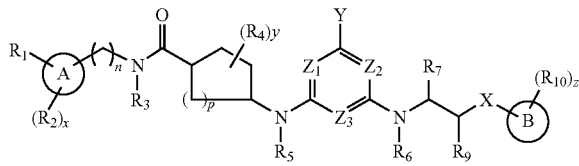

Formula II or a pharmaceutically acceptable salt thereof, wherein:

is a 6-membered aryl or heteroaryl ring;
$R_1$ is hydrogen, $CO_2H$, $CO_2(C_1-C_6)$alkyl, $CONR'R''$ wherein R' and R'' are each independently hydrogen or $(C_1-C_6)$alkyl, araalkyl, heteroaralkyl, —$(C_2-C_{10})$alkylene-NR'R'', —$(C_2-C_{10})$alkylene-OR', and —O—$(C_1-C_6)$alkyl, —S—$(C_1-C_6)$alkyl, any of which may be optionally substituted on carbon with 1, 2, or 3 halo;
each $R_2$ is if present independently halo, $(C_1-C_6)$alkyl, —O—$(C_1-C_6)$alkyl, —S—$(C_1-C_6)$alkyl, any of which may be optionally substituted on carbon with 1, 2, or 3 halo;
n is 0 or 1;
x is 0, 1, or 2;
$R_3$ is hydrogen or $(C_1-C_6)$alkyl;
p is 0, 1, 2, or 3;
each $R_4$ if present is independently halo, $(C_1-C_6)$alkyl, or —O—$(C_1-C_6)$alkyl, —S—$(C_1-C_6)$alkyl, any of which may be optionally substituted on carbon with 1, 2, or 3 halo, or taken together with the attached carbon forms C=O;
y is 0, 1, or 2;
$R_5$ is hydrogen or $(C_1-C_6)$alkyl;
$R_6$ is hydrogen or $(C_1-C_6)$alkyl;
$R_7$ is hydrogen, halo, or $(C_1-C_6)$alkyl;
$R_9$ is hydrogen, halo, or $(C_1-C_6)$alkyl;
X is absent or is O, $S(O)_m$ wherein m is 0, 1, or 2, —$CH_2$—S—, —$CH_2$—O—, —$CH_2$—NH—, or —$CH_2$—N($C_1-C_6$)alkyl-;

is $(C_3-C_6)$cycloalkyl, $(C_3-C_6)$heterocycloalkyl, aryl, or heteroaryl;
each $R_{10}$ if present is independently halo, $(C_1-C_6)$alkyl, —O—$(C_1-C_6)$alkyl, —S—$(C_1-C_6)$alkyl, any of which may be optionally substituted on carbon with 1, 2, or 3 halo, or taken together with the attached carbon forms C=O;
z is 0, 1, or 2;
$Z_1$, $Z_2$, and $Z_3$ are N;
Y is H, halo, $OR_{11}$, or $NR_{11}R_{12}$;
$R_{11}$ is hydrogen or $(C_1-C_6)$alkyl; and
$R_{12}$ is hydrogen, $(C_1-C_6)$alkyl, aryl, aralkyl, $(C_3-C_6)$cycloalkyl, -alkylene-$(C_3-C_6)$cycloalkyl, $(C_3-C_6)$heterocycloalkyl, -alkylene-$(C_3-C_6)$heterocycloalkyl, heteroaryl, heteroaralkyl, any of which may be optionally substituted on carbon with 1 or 2 groups selected from halo, $(C_1-C_6)$alkyl, —O—$(C_1-C_6)$alkyl, —S—$(C_1-C_6)$alkyl.

3. A compound of Formula III:

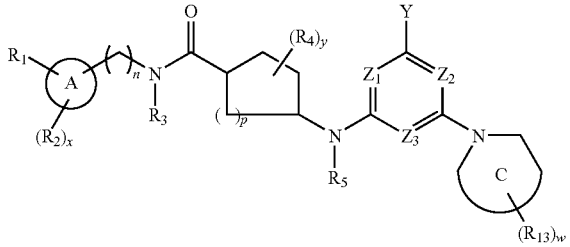

Formula III or a pharmaceutically acceptable salt thereof, wherein:

is a 6-membered aryl or heteroaryl ring;
$R_1$ is hydrogen, $CO_2H$, $CO_2(C_1-C_6)$alkyl, $CONR'R''$ wherein R' and R'' are each independently hydrogen or $(C_1-C_6)$alkyl, araalkyl, heteroaralkyl, —$(C_2-C_{10})$alkylene-NR'R'', —$(C_2-C_{10})$alkylene-OR', and —O—$(C_1-C_6)$alkyl, —S—$(C_1-C_6)$alkyl, any of which may be optionally substituted on carbon with 1, 2, or 3 halo;
each $R_2$ is if present independently halo, $(C_1-C_6)$alkyl, —O—$(C_1-C_6)$alkyl, —S—$(C_1-C_6)$alkyl, any of which may be optionally substituted on carbon with 1, 2, or 3 halo;
n is 0 or 1;
x is 0, 1, or 2;
$R_3$ is hydrogen or $(C_1-C_6)$alkyl;
p is 0, 1, 2, or 3;
each $R_4$ if present is independently halo, $(C_1-C_6)$alkyl, or —O—$(C_1-C_6)$alkyl, —S—$(C_1-C_6)$alkyl, any of which may be optionally substituted on carbon with 1, 2, or 3 halo, or taken together with the attached carbon forms C=O;
y is 0, 1, or 2;
$Z_1$, $Z_2$ and $Z_3$ are N;
$R_5$ is hydrogen or $(C_1-C_6)$alkyl;

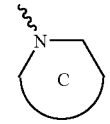

is a 3-10 membered ring, optionally containing 1 additional heteroatom selected from O, $S(O)_m$ wherein m is 0, 1, or 2, or NR''', wherein R''' is hydrogen or $(C_1-C_6)$alkyl, and wherein " ⁓ " indicate points of attachment;
each $R_{13}$ if present is independently halo, $(C_1-C_6)$alkyl, or —O—$(C_1-C_6)$alkyl, —S—$(C_1-C_6)$alkyl, any of which may be optionally substituted on carbon with 1, 2, or 3 halo, or taken together with the attached carbon forms C=O;
w is 0, 1, or 2;
Y is H, halo, $OR_{11}$, or $NR_{11}R_{12}$;
$R_{11}$ is hydrogen or $(C_1-C_6)$alkyl; and
$R_{12}$ is hydrogen, $(C_1-C_6)$alkyl, aryl, aralkyl, $(C_3-C_6)$cycloalkyl, -alkylene-$(C_3-C_6)$cycloalkyl, $(C_3-C_6)$heterocycloalkyl, -alkylene-($C_3$-$C_6$)heterocycloalkyl, heteroaryl, heteroalkyl, any of which may be optionally substituted on carbon with 1 or 2 groups selected from halo, ($C_1$-$C_6$)alkyl, —O—($C_1$-$C_6$)alkyl, —S—($C_1$-$C_6$)alkyl.

4. A compound chosen from:

cis-N-[(2,4-dichlorophenyl)methyl]-4-{[4-(methylamino)-6-(4-methyl-1-piperazinyl)-1,3,5-triazin-2-yl]amino} cyclohexanecarboxamide;

cis-N-[(2-fluorophenyl)methyl]-4-{[4-(methylamino)-6-(4-methyl-1-piperazinyl)-1,3,5-triazin-2-yl]amino} cyclohexanecarboxamide hydrochloride;

cis-N-[(3,4-difluorophenyl)methyl]-4-{[4-(methylamino)-6-(4-methyl-1-piperazinyl)-1,3,5-triazin-2-yl]amino}cyclohexanecarboxamide hydrochloride;

cis-N-cyclohexyl-4-{[4-(methylamino)-6-(4-methyl-1-piperazinyl)-1,3,5-triazin-2-yl]amino}cyclohexanecarboxamide hydrochloride;

cis-N-(cyclohexylmethyl)-4-{[4-(methylamino)-6-(4-methyl-1-piperazinyl)-1,3,5-triazin-2-yl]amino}cyclohexanecarboxamide hydrochloride;

cis-4-{[4-(methylamino)-6-(4-methyl-1-piperazinyl)-1,3,5-triazin-2-yl]amino}-N-{[2-(trifluoromethyl)phenyl]methyl}cyclohexanecarboxamide hydrochloride;

cis-N-[(2-chlorophenyl)methyl]-4-{[4-(methylamino)-6-(4-methyl-1-piperazinyl)-1,3,5-triazin-2-yl]amino}cyclohexanecarboxamide hydrochloride;

cis-4-{[4-(methylamino)-6-(4-methyl-1-piperazinyl)-1,3,5-triazin-2-yl]amino}-N-({2-[(trifluoromethyl)oxy]phenyl}methyl)cyclohexanecarboxamide hydrochloride;

trans-4-{[4-(methylamino)-6-(4-methyl-1-piperazinyl)-1,3,5-triazin-2-yl]amino}-N-{[2-(trifluoromethyl)phenyl]methyl}cyclohexanecarboxamide trifluoroacetate;

trans-4-{[4-(methylamino)-6-(4-methyl-1-piperazinyl)-1,3,5-triazin-2-yl]amino}-N-({2-[(trifluoromethyl)oxy]phenyl}methyl)cyclohexanecarboxamide trifluoroacetate;

trans-N-[(2,4-dichlorophenyl)methyl]-4-{[4-(methylamino)-6-(4-methyl-1-piperazinyl)-1,3,5-triazin-2-yl]amino}cyclohexanecarboxamide trifluoroacetate;

N-[(3,4-difluorophenyl)methyl]-3-{[4-(methylamino)-6-(4-methyl-1-piperazinyl)-1,3,5-triazin-2-yl]amino}cyclohexanecarboxamide hydrochloride;

N-(cyclohexylmethyl)-3-{[4-(methylamino)-6-(4-methyl-1-piperazinyl)-1,3,5-triazin-2-yl]amino}cyclohexanecarboxamide hydrochloride;

3-{[4-(methylamino)-6-(4-methyl-1-piperazinyl)-1,3,5-triazin-2-yl]amino}-N-{[2-(trifluoromethyl)phenyl]methyl}cyclohexanecarboxamide hydrochloride;

N-[(2-chlorophenyl)methyl]-3-{[4-(methylamino)-6-(4-methyl-1-piperazinyl)-1,3,5-triazin-2-yl]amino}cyclohexanecarboxamide hydrochloride;

N-[(2-fluorophenyl)methyl]-3-{[4-(methylamino)-6-(4-methyl-1-piperazinyl)-1,3,5-triazin-2-yl]amino}cyclohexanecarboxamide hydrochloride;

3-{[4-(methylamino)-6-(4-methyl-1-piperazinyl)-1,3,5-triazin-2-yl]amino}-N-({2-[(trifluoromethyl)oxy]phenyl}methyl)cyclohexanecarboxamide hydrochloride;

N-[(2,4-dichlorophenyl)methyl]-3-{[4-(methylamino)-6-(4-methyl-1-piperazinyl)-1,3,5-triazin-2-yl]amino}cyclohexanecarboxamide trifluoroacetate;

cis-N-[(2,4-dichlorophenyl)methyl]-4-{methyl[4-(methylamino)-6-(4-methyl-1-piperazinyl)-1,3,5-triazin-2-yl]amino}cyclohexanecarboxamide;

cis-4-{methyl[4-(methylamino)-6-(4-methyl-1-piperazinyl)-1,3,5-triazin-2-yl]amino}-N-{[2-(trifluoromethyl)phenyl]methyl}cyclohexanecarboxamide trifluoroacetate;

cis-4-{methyl[4-(methylamino)-6-(4-methyl-1-piperazinyl)-1,3,5-triazin-2-yl]amino}-N-({2-[(trifluoromethyl)oxy]phenyl}methyl)cyclohexanecarboxamide trifluoroacetate;

(1S,4S)-4-(4-(methylamino)-6-((R)-2-phenylpropylamino)-1,3,5-triazin-2-ylamino)-N-(2-(trifluoromethyl)benzyl)cyclohexanecarboxamide;

(1S,4S)-4-(4-(methylamino)-6-((R)-2-phenylpropylamino)-1,3,5-triazin-2-ylamino)-N-(2-(trifluoromethylthio)benzyl)cyclohexanecarboxamide;

(1S,4S)-4-(4-(methylamino)-6-((R)-2-phenylpropylamino)-1,3,5-triazin-2-ylamino)-N-(2-(trifluoromethoxy)benzyl)cyclohexanecarboxamide;

(1S,4S)-N-benzyl-4-(4-(methylamino)-6-((R)-2-phenylpropylamino)-1,3,5-triazin-2-ylamino)cyclohexanecarboxamide;

(1S,4S)-4-(4-(methylamino)-6-((R)-2-phenylpropylamino)-1,3,5-triazin-2-ylamino)-N-(4-(trifluoromethyl)benzyl)cyclohexanecarboxamide;

(1S,4S)-N-(4-fluorobenzyl)-4-(4-(methylamino)-6-((R)-2-phenylpropylamino)-1,3,5-triazin-2-ylamino)cyclohexanecarboxamide;

(1S,4S)-N-(2-fluorobenzyl)-4-(4-(methylamino)-6-((R)-2-phenylpropylamino)-1,3,5-triazin-2-ylamino)cyclohexanecarboxamide;

(1S,4S)-4-(4-(methylamino)-6-((R)-2-phenylpropylamino)-1,3,5-triazin-2-ylamino)-N-o-tolylcyclohexanecarboxamide;

(1R,4R)-N-benzyl-4-(4-(methylamino)-6-((R)-2-phenylpropylamino)-1,3,5-triazin-2-ylamino)cyclohexanecarboxamide;

methyl-4-4-(((1S,4S)-4-(4-(methylamino)-6-((R)-2-phenylpropylamino)-1,3,5-triazin-2-ylamino)cyclohexanecarboxamido)methyl)benzoate;

methyl-4-(((1R,4R)-4-(4-(methylamino)-6-((R)-2-phenylpropylamino)-1,3,5-triazin-2-ylamino)cyclohexanecarboxamido)methyl)benzoate;

4-(((1S,4S)-4-(4-(methylamino)-6-((R)-2-phenylpropylamino)-1,3,5-triazin-2-ylamino)cyclohexanecarboxamido)methyl)benzoic acid;

4-(((1R,4R)-4-(4-(methylamino)-6-((R)-2-phenylpropylamino)-1,3,5-triazin-2-ylamino)cyclohexanecarboxamido)methyl)benzoic acid;

2-(4-((1S,4S)-4-(4-(methylamino)-6-((R)-2-phenylpropylamino)-1,3,5-triazin-2-ylamino)cyclohexanecarboxamido)phenyl)acetic acid;

(1S,4S)-4-(4-(methylamino)-6-(piperidin-1-yl)-1,3,5-triazin-2-ylamino)-N-(2-(trifluoromethyl)benzyl)cyclohexanecarboxamide;

cis-4-{[4-(methylamino)-6-(4-methyl-l-piperazinyl)-1,3,5-triazin-2-yl]amino}-N-{[2-(trifluoromethyl)phenyl]methyl}cyclohexanecarboxamide hydrochloride;

cis-4-(4-(methylamino)-6-(pyrrolidin-1-yl)-1,3,5-triazin-2-ylamino)-N-(2-(trifluoromethyl)benzyl)cyclohexanecarboxamide;

cis-4-(4-(benzylamino)-6-(methylamino)-1,3,5-triazin-2-ylamino)-N-(2-(trifluoromethyl)benzyl)cyclohexanecarboxamide;

cis-4-(4-((2-(dimethylamino)ethyl)(methyl)amino)-6-(methylamino)-1,3,5-triazin-2-ylamino)-N-(2-(trifluoromethyl)benzyl)cyclohexanecarboxamide;

cis-4-(4-(azepan-1-yl)-6-(methylamino)-1,3,5-triazin-2-ylamino)-N-(2-(trifluoromethoxy) benzyl)cyclohexanecarboxamide;

cis-4-(4-amino-6-(azepan-1-yl)-1,3,5-triazin-2-ylamino)-N-(2-(trifluoromethoxy) benzyl)cyclohexanecarboxamide;

(1S,4S)-4-(4-amino-6((R)-2-phenylpropylamino)-1,3,5-triazin-2-ylamino)-N-(2-(trifluoromethoxy)benzyl)cyclohexanecarboxamide;

trans-4-(4-(methylamino)-6-(4-methylpiperazin-1-yl)-1,3,5-triazin-2-ylamino)-N-(2-(trifluoromethyl)benzyl)cyclohexanecarboxamide;

3-(4-(methylamino)-6-(4-methylpiperazin-1-yl)-1,3,5-triazin-2-ylamino)-N-(2-(trifluoromethyl)benzyl)cyclohexanecarboxamide.

5. A pharmaceutical composition comprising a compound or salt according to claim 1 and one or more pharmaceutically-acceptable excipients.

6. A pharmaceutical composition comprising a compound or salt according to claim 2 and one or more pharmaceutically-acceptable excipients.

7. A pharmaceutical composition comprising a compound or salt according to claim 3 and one or more pharmaceutically-acceptable excipients.

8. A method for treating asthma or COPD comprising administering a safe and effective amount of a compound or salt according to claim 1 to a patient in need thereof.

9. A method for treating asthma or COPD comprising administering a safe and effective amount of a compound or salt according to claim 2 to a patient in need thereof.

10. A method for treating asthma or COPD comprising administering a safe and effective amount of a compound or salt according to claim 3 to a patient in need thereof.

11. A method for treating asthma or COPD comprising administering a safe and effective amount of a compound or salt according to claim 4 to a patient in need thereof.

* * * * *